US010650912B2

(12) United States Patent
Schnall-Levin et al.

(10) Patent No.: US 10,650,912 B2
(45) Date of Patent: May 12, 2020

(54) SYSTEMS AND METHODS FOR VISUALIZING STRUCTURAL VARIATION AND PHASING INFORMATION

(71) Applicant: 10X Genomics, Inc., Pleasanton, CA (US)

(72) Inventors: Michael Schnall-Levin, San Francisco, CA (US); Alexander Wong, San Francisco, CA (US); David Luther Alan Stafford, San Francisco, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 1157 days.

(21) Appl. No.: 14/995,090

(22) Filed: Jan. 13, 2016

(65) Prior Publication Data

US 2016/0203196 A1 Jul. 14, 2016

Related U.S. Application Data

(60) Provisional application No. 62/120,873, filed on Feb. 25, 2015, provisional application No. 62/102,926, filed on Jan. 13, 2015.

(51) Int. Cl.
*G16B 50/00* (2019.01)
*G16C 99/00* (2019.01)
*G16B 45/00* (2019.01)
*G16B 30/00* (2019.01)

(52) U.S. Cl.
CPC ............ *G16B 50/00* (2019.02); *G16B 30/00* (2019.02); *G16B 45/00* (2019.02); *G16C 99/00* (2019.02)

(58) Field of Classification Search
CPC ............ C12Q 1/6869; C12Q 2537/165; G16B 30/00; G16B 40/00; G16B 20/00; G16B 50/00; G16B 20/20; G16B 15/00; G16B 25/00; G16B 30/10; G16B 40/20; G16B 5/00; G16B 10/00; G16B 20/10; G16B 15/10; G16B 20/40; G16B 25/10; G16B 30/20; G16B 35/00; G16B 40/10; G16B 40/30; G16B 50/10; G16B 50/50; G16B 5/20; G16B 99/00; G16H 50/20; G16H 10/40; G16H 20/00; G16H 50/30; G16H 10/60; G16H 50/50; G16H 50/70; G16H 70/60; G06N 7/005; G06N 20/00; G06N 10/00; G06N 20/20; G06N 3/002; G06N 3/04; G06N 3/0454; G06N 3/084; G06F 19/00; G06F 13/16; G06F 13/4265; G06F 19/18; G06F 19/22; G06F 5/08; G06F 7/00; G06F 9/3877; C40B 40/06; C40B 20/04; G16C 20/90; H01L 2027/11838; G06K 19/00; G06K 19/022; G06K 9/00986; G06K 9/628; G06K 9/6297; G06T 11/206; G11C 7/00
See application file for complete search history.

(56) References Cited

U.S. PATENT DOCUMENTS

| | | |
|---|---|---|
| 5,149,625 A | 9/1992 | Church et al. |
| 5,202,231 A | 4/1993 | Drmanac et al. |
| 5,413,924 A | 5/1995 | Kosak et al. |
| 5,436,130 A | 7/1995 | Mathies et al. |
| 5,512,131 A | 4/1996 | Kumar et al. |
| 5,587,128 A | 12/1996 | Wilding et al. |
| 5,605,793 A | 2/1997 | Stemmer |
| 5,618,711 A | 4/1997 | Gelfand et al. |
| 5,695,940 A | 12/1997 | Drmanac et al. |
| 5,736,330 A | 4/1998 | Fulton |
| 5,834,197 A | 11/1998 | Parton |
| 5,851,769 A | 12/1998 | Gray et al. |
| 5,856,174 A | 1/1999 | Lipshutz et al. |
| 5,958,703 A | 9/1999 | Dower et al. |
| 5,994,056 A | 11/1999 | Higuchi |

(Continued)

FOREIGN PATENT DOCUMENTS

| | | |
|---|---|---|
| EP | 0249007 A2 | 12/1987 |
| EP | 0637996 B1 | 7/1997 |

(Continued)

OTHER PUBLICATIONS

Zheng, X., SeqArray: an R/Bioconductor Package for Big Data Management of Genome-Wide Sequencing Variants, Department of Biostatistics, University of Washington-Seattle, Dec. 28, 2014.*
Ekblom, R. et al. "A field guide to whole-genome sequencing, assembly and annotation" Evolutionary Apps (Jun. 24, 2014) 7(9):1026-1042.
Jarosz, M. et al. "Using 1ng of DNA to detect haplotype phasing and gene fusions from whole exome sequencing of cancer cell lines" Cancer Res (2015) 75(suppl5):4742.
Lo, et al. On the design of clone-based haplotyping. Genome Biol. 2013;14(9):R100.
McCoy, R. et al. "Illumina TruSeq Synthetic Long-Reads Empower De Novo Assembly and Resolve Complex, Highly-Repetitive Transposable Elements" PLOS (2014) 9(9):e1016689.

(Continued)

*Primary Examiner* — Mary K Zeman
(74) *Attorney, Agent, or Firm* — Morgan, Lewis & Bockius LLP

(57) ABSTRACT

A system for providing structural variation or phasing information is provided. The system accesses a nucleic acid sequence dataset corresponding to a target nucleic acid in a sample. The dataset comprises a header, synopsis, and data section. The data section comprises a plurality of sequencing reads. Each sequencing read comprises a first portion corresponding to a subset of the target nucleic acid and a second portion that encodes an identifier for the sequencing read from a plurality of identifiers. One or more programs in the memory of the system use a microprocessor of the system to provide a haplotype visualization tool that receives a request for structural variation or phasing information from the dataset. The request is evaluated against the synopsis thereby identifying portions of the data section. Structural variation or phasing information is formatted for display in the haplotype visualization tool using the identified portions of the data section.

22 Claims, 37 Drawing Sheets

(56) References Cited

U.S. PATENT DOCUMENTS

| | | |
|---|---|---|
| 6,046,003 A | 4/2000 | Mandecki |
| 6,051,377 A | 4/2000 | Mandecki |
| 6,057,107 A | 5/2000 | Fulton |
| 6,103,537 A | 8/2000 | Ullman et al. |
| 6,143,496 A | 11/2000 | Brown et al. |
| 6,172,218 B1 | 1/2001 | Brenner |
| 6,297,006 B1 | 10/2001 | Drmanac et al. |
| 6,297,017 B1 | 10/2001 | Thompson |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,406,848 B1 | 6/2002 | Bridgham et al. |
| 6,432,360 B1 | 8/2002 | Church |
| 6,485,944 B1 | 11/2002 | Church et al. |
| 6,511,803 B1 | 1/2003 | Church et al. |
| 6,524,456 B1 | 2/2003 | Ramsey et al. |
| 6,586,176 B1 | 7/2003 | Trnovsky et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,323,305 B2 | 1/2008 | Leamon et al. |
| 7,425,431 B2 | 9/2008 | Church et al. |
| 7,536,928 B2 | 5/2009 | Kazuno |
| 7,604,938 B2 | 10/2009 | Takahashi et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,708,949 B2 | 5/2010 | Stone et al. |
| 7,709,197 B2 | 5/2010 | Drmanac |
| 7,745,178 B2 | 6/2010 | Dong |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,067,159 B2 | 11/2011 | Brown et al. |
| 8,133,719 B2 | 3/2012 | Drmanac et al. |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,304,193 B2 | 11/2012 | Ismagilov et al. |
| 8,329,407 B2 | 12/2012 | Ismagilov et al. |
| 8,337,778 B2 | 12/2012 | Stone et al. |
| 8,592,150 B2 | 11/2013 | Drmanac et al. |
| 8,603,749 B2 | 12/2013 | Gillevet |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,871,444 B2 | 10/2014 | Griffiths et al. |
| 8,889,083 B2 | 11/2014 | Ismagilov et al. |
| 9,012,370 B2 | 4/2015 | Hong |
| 9,017,948 B2 | 4/2015 | Agresti et al. |
| 9,029,083 B2 | 5/2015 | Griffiths et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,694,361 B2 | 7/2017 | Bharadwaj |
| 9,695,468 B2 | 7/2017 | Hindson et al. |
| 9,824,068 B2 | 11/2017 | Wong et al. |
| 10,119,167 B2 | 11/2018 | Srinivasan et al. |
| 10,221,442 B2 | 3/2019 | Hindson et al. |
| 2001/0020588 A1 | 9/2001 | Adourian et al. |
| 2001/0044109 A1 | 11/2001 | Mandecki |
| 2002/0034737 A1 | 3/2002 | Drmanac |
| 2002/0051992 A1 | 5/2002 | Bridgham et al. |
| 2002/0089100 A1 | 7/2002 | Kawasaki |
| 2002/0092767 A1 | 7/2002 | Bjornson et al. |
| 2002/0179849 A1 | 12/2002 | Maher et al. |
| 2003/0008285 A1 | 1/2003 | Fischer |
| 2003/0008323 A1 | 1/2003 | Ravkin et al. |
| 2003/0027221 A1 | 2/2003 | Scott et al. |
| 2003/0028981 A1 | 2/2003 | Chandler et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0104466 A1 | 6/2003 | Knapp et al. |
| 2003/0108897 A1 | 6/2003 | Drmanac |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0132122 A1 | 7/2004 | Banerjee et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0287572 A1 | 12/2005 | Mathies et al. |
| 2006/0020371 A1 | 1/2006 | Ham et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0054119 A1 | 3/2007 | Garstecki et al. |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0111241 A1 | 5/2007 | Cereb et al. |
| 2007/0154903 A1 | 7/2007 | Marla et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0213766 A1 | 9/2008 | Brown et al. |
| 2008/0241820 A1 | 10/2008 | Krutzik et al. |
| 2008/0268431 A1 | 10/2008 | Choy et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |

(56) References Cited

U.S. PATENT DOCUMENTS

| | | |
|---|---|---|
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0118488 A1 | 5/2009 | Drmanac et al. |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0069263 A1 | 3/2010 | Shendure et al. |
| 2010/0105112 A1 | 4/2010 | Holtze et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston et al. |
| 2010/0210479 A1 | 8/2010 | Griffiths et al. |
| 2010/0216153 A1 | 8/2010 | Lapidus et al. |
| 2011/0033854 A1 | 2/2011 | Drmanac et al. |
| 2011/0053798 A1 | 3/2011 | Hindson et al. |
| 2011/0071053 A1 | 3/2011 | Drmanac et al. |
| 2011/0086780 A1 | 4/2011 | Colston et al. |
| 2011/0092376 A1 | 4/2011 | Colston et al. |
| 2011/0092392 A1 | 4/2011 | Colston et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0257889 A1 | 10/2011 | Klammer et al. |
| 2011/0263457 A1 | 10/2011 | Krutzik et al. |
| 2011/0267457 A1 | 11/2011 | Weitz et al. |
| 2011/0281738 A1 | 11/2011 | Drmanac et al. |
| 2011/0305761 A1 | 12/2011 | Shum et al. |
| 2011/0319281 A1 | 12/2011 | Drmanac |
| 2012/0000777 A1 | 1/2012 | Garrell et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0041727 A1 | 2/2012 | Mishra et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0172259 A1 | 7/2012 | Rigatti et al. |
| 2012/0184449 A1 | 7/2012 | Hixson et al. |
| 2012/0190032 A1 | 7/2012 | Ness et al. |
| 2012/0196288 A1 | 8/2012 | Beer |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0230338 A1 | 9/2012 | Ganeshalingam et al. |
| 2012/0309002 A1 | 12/2012 | Link |
| 2012/0316074 A1 | 12/2012 | Saxonov |
| 2013/0028812 A1 | 1/2013 | Prieto et al. |
| 2013/0046030 A1 | 2/2013 | Rotem et al. |
| 2013/0078638 A1 | 3/2013 | Berka et al. |
| 2013/0079231 A1 | 3/2013 | Pushkarev et al. |
| 2013/0109575 A1 | 5/2013 | Kleinschmidt et al. |
| 2013/0130919 A1 | 5/2013 | Chen et al. |
| 2013/0157870 A1 | 6/2013 | Pushkarev et al. |
| 2013/0157899 A1 | 6/2013 | Adler et al. |
| 2013/0178368 A1 | 7/2013 | Griffiths et al. |
| 2013/0185096 A1* | 7/2013 | Giusti .......... G06Q 50/24 705/3 |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0225418 A1 | 8/2013 | Watson |
| 2013/0268206 A1 | 10/2013 | Porreca et al. |
| 2013/0274117 A1 | 10/2013 | Church et al. |
| 2013/0311106 A1 | 11/2013 | White et al. |
| 2013/0317755 A1 | 11/2013 | Mishra et al. |
| 2014/0037514 A1 | 2/2014 | Stone et al. |
| 2014/0057799 A1 | 2/2014 | Johnson et al. |
| 2014/0065234 A1 | 3/2014 | Shum et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0200166 A1 | 7/2014 | Van Rooyen et al. |
| 2014/0206554 A1 | 7/2014 | Hindson et al. |
| 2014/0214334 A1 | 7/2014 | Plattner et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0287963 A1 | 9/2014 | Hindson et al. |
| 2014/0302503 A1 | 10/2014 | Lowe et al. |
| 2014/0323316 A1 | 10/2014 | Drmanac et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0066385 A1 | 3/2015 | Schnall-Levin et al. |
| 2015/0111256 A1 | 4/2015 | Church et al. |
| 2015/0133344 A1 | 5/2015 | Shendure et al. |
| 2015/0218633 A1 | 8/2015 | Hindson et al. |
| 2015/0220532 A1 | 8/2015 | Wong |
| 2015/0224466 A1 | 8/2015 | Hindson et al. |
| 2015/0225777 A1 | 8/2015 | Hindson et al. |
| 2015/0225778 A1 | 8/2015 | Hindson et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0376605 A1 | 12/2015 | Jarosz et al. |
| 2015/0376609 A1 | 12/2015 | Hindson et al. |
| 2015/0376700 A1* | 12/2015 | Schnall-Levin ..... C12Q 1/6883 506/4 |
| 2015/0379196 A1 | 12/2015 | Schnall-Levin et al. |
| 2016/0232291 A1 | 8/2016 | Kyriazopoulou-Panagiotopoulou et al. |
| 2016/0304860 A1 | 10/2016 | Hindson et al. |
| 2016/0350478 A1 | 12/2016 | Chin et al. |
| 2017/0235876 A1 | 8/2017 | Jaffe et al. |
| 2018/0196781 A1 | 7/2018 | Wong |
| 2018/0265928 A1 | 9/2018 | Schnall-Levin et al. |

FOREIGN PATENT DOCUMENTS

| | | |
|---|---|---|
| EP | 1019496 B1 | 9/2004 |
| EP | 1482036 B1 | 10/2007 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| GB | 2485850 A | 5/2012 |
| JP | 5949832 A | 3/1984 |
| JP | 2006-507921 A | 3/2006 |
| JP | 2006-289250 A | 10/2006 |
| JP | 2007-268350 A | 10/2007 |
| JP | 2009-208074 | 9/2009 |
| RU | 2321638 C2 | 4/2008 |
| WO | WO-1996029629 A2 | 9/1996 |
| WO | WO-1996041011 A1 | 12/1996 |
| WO | WO-1999009217 A1 | 2/1999 |

(56) References Cited

FOREIGN PATENT DOCUMENTS

| | | |
|---|---|---|
| WO | WO-1999052708 A1 | 10/1999 |
| WO | WO-2000008212 A1 | 2/2000 |
| WO | WO-2000026412 A1 | 5/2000 |
| WO | WO-2001014589 A2 | 3/2001 |
| WO | WO-2001089787 A2 | 11/2001 |
| WO | WO-2002031203 A2 | 4/2002 |
| WO | WO-2002086148 A1 | 10/2002 |
| WO | WO-2004002627 A2 | 1/2004 |
| WO | WO-2004010106 A2 | 1/2004 |
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A1 | 3/2005 |
| WO | WO-2005040406 A1 | 5/2005 |
| WO | WO-2005049787 A9 | 6/2005 |
| WO | WO-2005082098 A2 | 9/2005 |
| WO | WO-2006030993 A1 | 3/2006 |
| WO | WO-2006078841 A1 | 7/2006 |
| WO | WO-2006096571 A2 | 9/2006 |
| WO | WO-2007001448 A2 | 1/2007 |
| WO | WO-2007002490 A2 | 1/2007 |
| WO | WO-2007024840 A2 | 3/2007 |
| WO | WO-2007081385 A2 | 7/2007 |
| WO | WO-2007081387 A1 | 7/2007 |
| WO | WO-2007089541 A2 | 8/2007 |
| WO | WO-2007114794 A1 | 10/2007 |
| WO | WO-2007121489 A2 | 10/2007 |
| WO | WO-2007133710 A2 | 11/2007 |
| WO | WO-2007138178 A2 | 12/2007 |
| WO | WO-2007139766 A2 | 12/2007 |
| WO | WO-2007140015 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | WO-2008134153 A1 | 11/2008 |
| WO | WO-2009005680 A1 | 1/2009 |
| WO | WO-2009011808 A1 | 1/2009 |
| WO | WO 2009/023821 A1 | 2/2009 |
| WO | WO-2009061372 A1 | 5/2009 |
| WO | WO-2009085215 A1 | 7/2009 |
| WO | WO-2010004018 A2 | 1/2010 |
| WO | WO-2010033200 A2 | 3/2010 |
| WO | WO-2010115154 A1 | 10/2010 |
| WO | 2010126614 A2 | 11/2010 |
| WO | WO-2010127304 A2 | 11/2010 |
| WO | WO-2010148039 A2 | 12/2010 |
| WO | WO-2010151776 A2 | 12/2010 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | WO-2012012037 A1 | 1/2012 |
| WO | WO-2012048341 A1 | 4/2012 |
| WO | WO 2012/061832 A1 | 5/2012 |
| WO | WO-2012055929 A1 | 5/2012 |
| WO | WO 2012/100216 A2 | 7/2012 |
| WO | 2012112804 A1 | 8/2012 |
| WO | WO-2012106546 A2 | 8/2012 |
| WO | WO-2012116331 A2 | 8/2012 |
| WO | WO-2012083225 A2 | 9/2012 |
| WO | WO 2012/142531 A2 | 10/2012 |
| WO | WO 2012/142611 A2 | 10/2012 |
| WO | WO-2012149042 A2 | 11/2012 |
| WO | WO-2012166425 A2 | 12/2012 |
| WO | WO-2013035114 A1 | 3/2013 |
| WO | 2013055955 A1 | 4/2013 |
| WO | WO-2013123125 A1 | 8/2013 |
| WO | WO-2013177220 A1 | 11/2013 |
| WO | WO-2014028537 A1 | 2/2014 |
| WO | WO 2014/093676 A1 | 6/2014 |
| WO | WO 2015/157567 A1 | 10/2015 |
| WO | WO 2015/200891 A1 | 12/2015 |
| WO | WO-2016130578 A1 | 8/2016 |

OTHER PUBLICATIONS

Ritz, A. et al. "Characterization of structural variants with single molecule and hybrid sequencing approaches" Bioinformatics (2014) 30(24):3458-3466.

Voskoboynik, A. et al. "The genome sequence of the colonial chordate, Botryllus schlosseri." eLife Jul. 2, 2013, 2: e00569.

Zerbino, D.R. "Using the Velvet de novo assembler for short-read sequencing technologies" Curr Protoc Bioinformatics (Sep. 1, 2010) 31:11.5:11.5.1"11.5.12.

Zheng, X.Y. et al. "Haplotyping germline and cancer genomes with high-throughput linked-read sequencing" Nature Biotech (Feb. 1, 2016) 34(3):303-311 and Supplemental Material.

Extended European Search Report for EP Application No. 16737834.8, dated Jul. 27, 2018, 10 pages.

U.S. Appl. No. 15/019,928, filed Feb. 9, 2016, 10X Genomics, Inc.

International Search Report for International Patent Application No. PCT/US2016/013290, dated May 19, 2016, 11 pages.

International Search Report for International Patent Application No. PCT/US2016/017196, dated May 29, 2016, 14 pages.

Bansal et al., "HapCUT: an efficient and accurate algorithm for the haplotype assembly problem," Bioinformatics, vol. 24, 2008, pp. i153-i159.

Bansal et al., 2008, "An MCMC algorithm for haplotype assembly from whole-genome sequence data," Genome Res, 18:1336-1346.

Bentley et al., 2008, Accurate whole human genome sequencing using reversible terminator chemistry, Nature 456:53-59.

Bray, "The JavaScript Object Notation (JSON) Data Interchange Format," Mar. 2014, retrieved from the Internet Feb. 15, 2015; https://tools.ietf.org/html/rfc7159.

Browning et al., "Haplotype phasing: Existing methods and new developments," Nat Rev Genet., 12(10), Apr. 1, 2012, pp. 703-714.

Chen et al., 2009, "BreakDancer: an algorithm for high-resolution mapping of genomic structural variation," Nature Methods 6(9), pp. 677-681.

Choi et al., 2008, "Identification of novel isoforms of the EML4-ALK transforming gene in non-small cell lung cancer," Cancer Res, 68:4971-4976.

Cleary et al., 2014, "Joint variant and de novo mutation identification on pedigrees from high-throughput sequencing data," J Comput Biol, 21:405-419.

Eid et al., "Real-time sequencing form single polymerase molecules," Science 323:133-138.

Gordon et al., 1998, "Consed: A Graphical Tool for Sequence Finishing," Genome Research 8:198-202.

Heng and Durbin, 2010, "Fast and accurate long-read alignment with Burrows-Wheeler transform," Bioinformatics, 25(14): 1754-1760.

Huang and Marth, 2008, "EagleView: A genome assembly viewer for next-generation sequencing technologies," Genome Research 18:1538-1543.

Kanehisa and Goto, 2000, "KEGG: Kyoto Encyclopedia of Genes and Genomes," Nucleic Acids Research 28, 27-30.

Kim et al., "HapEdit: an accuracy assessment viewer for haplotype assembly using massively parallel DNA-sequencing technologies," Nucleic Acids Research, 2011, pp. 1-5.

Kirkness et al., 2013, "Sequencing of isolated sperm cells for direct haplotyping of a human genome," Genome Res, 23:826-832.

Kitzman et al., 2011, "Haplotype-resolved genome sequencing of a Gujarati Indian individual." Nat Biotechnol, 29:59-63.

Layer et al., 2014, "LUMPY: A probabilistic framework for structural variant discovery," Genome Biology 15(6):R84.

Lippert et al., 2002, "Algorithmic strategies for the single nucleotide polymorphism haplotype assembly problem," Brief. Bionform 3:23-31.

(56) References Cited

OTHER PUBLICATIONS

Margulies et al., 2005, "Genome sequencing in microfabricated high-density picoliter reactors," Nature 437:376-380.
McKenna et al., "The Genome Analysis Toolkit: A MapReduce framework for anaylzing next-generation DNA sequencing data," Genome Research, 2010, pp. 1297-1303.
Miller et al., "Assembly Algorithms for next-generation sequencing data," Genomics, 95 (2010), pp. 315-327.
Myllykangas et al., 2011, "Efficient targeted resequencing of human germline and cancer genomes by oligonucleotide-selective sequencing," Nat Biotechnol, 29:1024-1027.
Pushkarev et al., 2009, "Single-molecule sequencing of an individual human genome," Nature Biotech 17:847-850.
Shendure et al., 2005, "Accurate Multiplex Polony Sequencing of an Evolved bacterial Genome" Science 309:1728-1732.
Tewhey et al., 2011, "The importance of phase information for human genomics," Nat Rev Genet, 12:215-223.
The SAM/BAM Format Specificatio Working Group, "Sequence Allignment/ Map Format Specification," Dec. 28, 2014.
Wheeler et al.,2007, "Database resources of the National Center for Biotechnology Information," Nucleic Acids Res. 35 (Database issue): D5-12.
Zerbino et al., "Velvet: Algorithms for de novo short read assembly using de Bruijn graphs," Genome Research 18, 2008, pp. 821-829.
Zerbino, Daniel, "Velvet Manual—version 1.1," Aug. 15, 2008, pp. 1-22.
"SSH Tunnel—Local and Remote Port Forwarding Explained With Examples," Trackets Blog, http://blog.trackets.com/2014/05/17/ssh-tunnel-local-and-remote-port-forwarding-explained-with-examples.html; Retrieved from the Internet Jul. 7, 2016.
"Bedtools: General Usage," http://bedtools.readthedocs.io/en/latest/content/general-usage.html; Retrieved from the Internet Jul. 8, 2016.
Co-pending U.S. Appl. No. 15/242,256, filed Aug. 19, 2016.
Margulies 2005 Supplementary methods (Year: 2005).
Abate et al., Valve-based flow focusing for drop formation. Appl Phys Lett. 2009;94. 3 pages.
Abate, A.R. et al. "Beating Poisson encapsulation statistics using close-packed ordering" Lab on a Chip (Sep. 21, 2009) 9(18):2628-2631.
Abate, et al. High-throughput injection with microfluidics using picoinjectors. Proc Natl Acad Sci U S A. Nov. 9, 2010;107(45):19163-6. doi: 10.1073-pNas.1006888107. Epub Oct. 20, 2010.
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Aitman, et al. Copy number polymorphism in Fcgr3 predisposes to glomerulonephritis in rats and humans. Nature. Feb. 16, 2006;439(7078):851-5.
Akselband, "Enrichment of slow-growing marine microorganisms from mixed cultures using gel microdrop (GMD) growth assay and fluorescence-activated cell sorting", J. Exp. Marine Biol., 329: 196-205 (2006).
Akselband, "Rapid mycobacteria drug susceptibility testing using gel microdrop (GMD) growth assay and flow cytometry", J. Microbiol. Methods, 62:181-197 (2005).
Anna et al., "Formation of dispersions using 'flow focusing' in microchannels", Appln. Phys. Letts. 82:3 364 (2003).
Attia, U.M et al., "Micro-injection moulding of polymer microfluidic devices" Microfluidics and nanofluidics (2009) 7(1):1-28.
Balikova, et al. Autosomal-dominant microtia linked to five tandem copies of a copy-number-variable region at chromosome 4p16. Am J Hum Genet. Jan. 2008;82(1):181-7. doi: 10.1016-j.ajhg.2007.08.001.
Baret et al. "Fluorescence-activated droplet sorting (FADS): efficient microfluidic cell sorting based on enzymatic activity" Lab on a Chip (2009) 9(13):1850-1858.

Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039-b814810d. Epub Nov. 20, 2008.
Brouzes, E et al., "Droplet microfluidic technology for single-cell high-throughput screening" PNAS (2009) 106(34):14195-14200.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Chaudhary "A rapid method of cloning functional variable-region antibody genes in Escherichia coli as single-chain immunotoxins" Proc. Nat!. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;I8(1):83-101.
Chen, F et al., "Chemical transfection of cells in picoliter aqueous droplets in fluorocarbon oil" Anal. Chem. (2011) 83:8816-8820.
Chokkalingam, V et al., "Probing cellular heterogeneity in cytokine-secreting immune cells using droplet-based microfluidics" Lab Chip (2013) 13:4740-4744.
Chou, H-P. et al. "Disposable Microdevices for DNA Analysis and Cell Sorting Proc. Solid-State Sensor and Actuator Workshop" Hilton Head, SC Jun. 8-11, 1998, pp. 11-14.
Chu, L-Y. et al., "Controllable monodisperse multiple emulsions" Angew. Chem. Int. Ed. (2007) 46:8970-8974.
Clausell-Tormos et al., "Droplet-based microfluidic platforms for the encapsulation and screening of mammalian cells and multicellular organisms", Chem. Biol. 15:427-437 (2008).
Cook, et al. Copy-number variations associated with neuropsychiatric conditions. Nature. Oct. 16, 2008;455(7215):919-23. doi: 10.1038-nature07458.
De Bruin et al., UBS Investment Research. Q-Seriesï¿½: DNa Sequencing. UBS Securities LLC. Jul. 12, 2007. 15 pages.
Demirci, et al. "Single cell epitaxy by acoustic picolitre droplets" Lab Chip. Sep. 2007;7(9):1139-45. Epub Jul. 10, 2007.
Doerr, "The smallest bioreactor", Nature Methods, 2:5 326 (2005).
Dowding, et al. "Oil core-polymer shell microcapsules by interNal phase separation from emulsion droplets. II: controlling the release profile of active molecules" Langmuir. Jun. 7, 2005;21(12):5278-84.
Draper, M.C. et al., "Compartmentalization of electrophoretically separated analytes in a multiphase microfluidic platform" Anal. Chem. (2012) 84:5801-5808.
Dressler, O.J. et al., "Droplet-based microfluidics enabling impact on drug discovery" J. Biomol. Screen (2014) 19(4):483-496.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Eastburn, D.J. et al., "Ultrahigh-throughput mammalian single-cell reverse-transcriptase polymerase chain reaction in microfluidic droplets" Anal. Chem. (2013) 85:8016-8021.
Esser-Kahn, et al. Triggered release from polymer capsules. Macromolecules. 2011; 44:5539-5553.
Fabi, et al. Correlation of efficacy between EGFR gene copy number and lapatinib-capecitabine therapy in HER2-positive metastatic breast cancer. J. Clin. Oncol. 2010; 28:15S. 2010 ASCO Meeting abstract Jun. 14, 2010:1059.
Fisher, S. et al. "A Scalable, fully automated process for construction of sequence-ready human exome targeted capture libraries" Genome Biology (2011) 2:R1-R15. doi: 10.1186-gb-2011-12-1-r1. Epub Jan. 4, 2011.
Fredrickson, C.K. et al., "Macro-to-micro interfaces for microfluidic devices" Lab Chip (2004) 4:526-533.

(56) References Cited

OTHER PUBLICATIONS

Freiberg, et al. "Polymer microspheres for controlled drug release" Int J Pharm. Sep. 10, 2004;282(1-2):1-18.

Fu. A.Y. et al. "A microfabricated fluorescence-activated cell sorter" Nature Biotech (Nov. 1999) 17:1109-1111.

Fulton et al., "Advanced multiplexed analysis with the FlowMetrix system" Clin Chem. Sep. 1997;43(9): 1749-56.

Garstecki, P. et al. "Formation of monodisperse bubbles in a microfluidic flow-focusing device" Appl. Phys. Lett (2004) 85(13):2659-2651. DOI: 10.1063-1.1796526.

Gartner, et al. The Microfluidic Toolbox ï¿½examples for fluidic interfaces and standardization concepts. Proc. SPIE 4982, Microfluidics, BioMEMS, and Medical Microsystems, (Jan. 17, 2003); doi: 10.1117-12.479566.

Ghadessy, et al. Directed evolution of polymerase function by compartmentalized self-replication. Proc Natl Acad Sci U S A. Apr. 10, 2001;98(8):4552-7. Epub Mar. 27, 2001.

Gonzalez, et al. The influence of CCL3L1 gene-containing segmental duplications on HIV-1-AIDS susceptibility. Science. Mar. 4, 2005;307(5714):1434-40. Epub Jan. 6, 2005.

Granieri, Lucia "Droplet-based microfluidics and engineering of tissue plasminogen activator for biomedical applications" Ph.D. Thesis, Nov. 13, 2009 (131 pages).

Grasland-Mongrain, E. et al. "Droplet coalescence in microlfuidic devices" Internet Citation, 2003, XP002436104, Retrieved from the Internet: URL:http:--www.eleves.ens.fr.home-grasland-rapports-stage4.pdf [retrieved on Jun. 4, 2007].

Guo, M.T. et al., "Droplet microfluidics for high-throughput biological assays" Lab Chip (2012) 12:2146-2155.

Gyarmati et al., "Reversible Disulphide Formation in Polymer Networks: A Versitile Functional Group from Synthesis to Application," European Polymer Journal, 2013, 49, 1268-1286.

Hashimshony, T et al. "CEL-Seq: Single-Cell RNa-Seq by Multiplexed Linear Amplification" Cell Rep. Sep. 27, 2012;2(3):666-73. doi: 10.1016-j.celrep.2012.08.003. Epub Aug. 30, 2012.

He "Selective Encapsulation of Single Cells and Subcellular Organelles into Picoliter- and Femtoliter-Volume Droplets" Anal. Chern 77: 1539-1544 (2005).

Holtze, C. et al. Biocompatible surfactants for water-in-fluorocarbon emulsions. Lab Chip. Oct. 2008;8(10):1632-9. doi: 10.1039-b806706f. Epub Sep. 2, 2008.

Huebner, "Quantitative detection of protein expression in single cells using droplet microfluidics", Chern. Commun. 1218-1220 (2007).

Hug, H. et al. "Measurement of the number of molecules of a single mRNA species in a complex mRNA preparation" J Theor Biol. Apr. 21, 2003;221(4):615-24.

Illumina, Inc. An Introduction to Next-Generation Sequencing Technology. Feb. 28, 2012.

Jena et al., "Cyclic olefin copolymer based microfluidic devices for biochip applications: Ultraviolet surface grafting using 2-methacryloyloxyethyl phosphorylchloline" Biomicrofluidics (Mar. 15, 2012) 6:012822 (12 pages).

Jung, W-C et al., "Micromachining of injection mold inserts for fluidic channel of polymeric biochips" Sensors (2007) 7:1643-1654.

Khomiakov A et al., "Analysis of perfect and mismatched DNA duplexes by a generic hexanucleotide microchip". Mol Bioi (Mosk). Jul.-Aug. 2003;37(4):726-41. Russian. Abstract only.

Kim, et al. Albumin loaded microsphere of amphiphilic poly(ethylene glycol)-poly(alpha-ester) multiblock copolymer. Eur J Pharm Sci. Nov. 2004;23(3):245-51.

Kim, et al. Fabrication of monodisperse gel shells and functioNal microgels in microfluidic devices. Angew Chem Int Ed Engl. 2007;46(11):1819-22.

Kim, J et al., "Rapid prototyping of microfluidic systems using a PDMS-polymer tape composite" Lab Chip (2009) 9:1290-1293.

Kitzman, et al. Noninvasive whole-genome sequencing of a human fetus. Sci Transl Med. Jun. 6, 2012;4(137):137ra76. doi: 10.1126-scitranslmed.3004323.

Klein, et al. Droplet barcoding for single-cell transcriptomics applied to embryonic stem cells. Cell. May 21, 2015; 161:1187-1201.

Knight, et al. Subtle chromosomal rearrangements in children with unexplained mental retardation. Lancet. Nov. 13, 1999;354(9191):1676-81.

Koster et al., "Drop-based microfluidic devices for encapsulation of single cells", Lab on a Chip The Royal Soc. of Chern. 8: 1110-1115 (2008).

Kutyavin, et al. Oligonucleotides containing 2-aminoadenine and 2-thiothymine act as selectively binding complementary agents. Biochemistry. Aug. 27, 1996;35(34):11170-6.

Lagus, T.P. et al., "A review of the theory, methods and recent applications of high-throughput single-cell droplet microfluidics" J. Phys. D: Appl. Phys. (2013) 46:114005 (21 pages).

Li, Y., et al., "PEGylated PLGA Nanoparticles as protein carriers: synthesis, preparation and biodistribution in rats," Journal of Controlled Release, vol. 71, pp. 203-211 (2001).

Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.

Liu, et al. Smart thermo-triggered squirting capsules for Nanoparticle delivery. Soft Matter. 2010; 6(16):3759-3763.

Loscertales, I.G., et al., "Micro-Nano Encapsulation via Electrified Coaxial Liquid Jets," Science, vol. 295, pp. 1695-1698 (2002).

Love, "A microengraving method for rapid selection of single cells producing antigen-specific antibodies", Nature Biotech, 24(6):703-707 (Jun. 2006).

Lowe, Adam J. "Norbornenes and [n]polynorbornanes as molecular scaffolds for anion recognition" Ph.D. Thesis (May 2010). (361 pages).

Lupski. Genomic rearrangements and sporadic disease. Nat Genet. Jul. 2007;39(7 Suppl):S43-7.

Macosko, et al. Highly Parallel Genome-wide Expression Profiling of Individual Cells Using Nanoliter Droplets. Cell. May 21, 2015;161(5):1202-14. doi: 10.1016-j.cell.2015.05.002.

Mair, D.A. et al., "Injection molded microfluidic chips featuring integrated interconnects" Lab Chip (2006) 6:1346-1354.

Makino, K. et al. "Preparation of hydrogel microcapsules Effects of preparation conditions upon membrane properties" Colloids and Surfaces: B Biointerfaces (1998) 12:97-104.

Marcus. Gene method offers diagnostic hope. The Wall Street Journal. Jul. 11, 2012.

Matochko, W.L. et al., "Uniform amplification of phage display libraries in monodisperse emulsions," Methods (2012) 58:18-27.

Mazutis, et al. Selective droplet coalescence using microfluidic systems. Lab Chip. Apr. 24, 2012;12(10):1800-6. doi: 10.1039-c2lc40121e. Epub Mar. 27, 2012.

Merriman, et al. Progress in ion torrent semiconductor chip based sequencing. Electrophoresis. Dec. 2012;33(23):3397-3417. doi: 10.1002-elps.201200424.

Microfluidic ChipShop. Microfluidic product catalogue. Mar. 2005.

Microfluidic ChipShop. Microfluidic product catalogue. Oct. 2009.

Mirzabekov, "DNA Sequencing by Hybridization—a Megasequencing Method and a Diagnostic Tool?" Trends in Biotechnology 12(1): 27-32 (1994).

Moore, J.L. et al., "Behavior of capillary valves in centrifugal microfluidic devices prepared by three-dimensional printing" Microfluid Nanofluid (2011) 10:877-888.

Mouritzen et al., Single nucleotide polymorphism genotyping using locked nucleic acid (LNa). Expert Rev Mol Diagn. Jan. 2003;3(1):27-38.

Nagashima, S. et al. "Preparation of monodisperse poly(acrylamide-co-acrylic acid) hydrogel microspheres by a membrane emulsification technique and their size dependent surface properties" Colloids and Surfaces: B Biointerfaces (1998) 11:47-56.

Navin, N. E. "The first five years of single-cell cancer genomics and beyond" Genome Res. (2015) 25:1499-1507.

Nguyen, et al. In situ hybridization to chromosomes stabilized in gel microdrops. Cytometry. 1995; 21:111-119.

Novak, R. et al., "Single cell multiplex gene detection and sequencing using microfluidicallygenerated agarose emulsions" Angew. Chem. Int. Ed. Engl. (2011) 50(2):390-395.

(56) References Cited

OTHER PUBLICATIONS

Oberholzer, et al. Polymerase chain reaction in liposomes. Chem Biol. Oct. 1995;2(10):677-82.
Ogawa, et al. Production and characterization of O-W emulsions containing cationic droplets stabilized by lecithin-chitosan membranes. J Agric Food Chem. Apr. 23, 2003;51(9):2806-12.
Okushima, "Controlled production of monodisperse double emulsions by two-step droplet breakup in microfluidic devices", Langmuir, 20:9905-9908 (2004).
Perez, C., et al., "Poly(lactic acid)-poly(ethylene glycol) Nanoparticles as new carriers for the delivery ofplasmid DNa," Journal of Controlled Release, vol. 75, pp. 211-224 (2001).
Peters et al., "Accurate whole-genome sequencing and haplotyping from 10 to 20 human cells," Nature, Jul. 12, 2012, vol. 487, pp. 190-195.
Pinto, et al. Functional impact of global rare copy number variation in autism spectrum disorders. Nature. Jul. 15, 2010;466(7304):368-72. doi: 10.1038-nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Ropers. New perspectives for the elucidation of genetic disorders. Am J Hum Genet. Aug. 2007;81(2):199-207. Epub Jun. 29, 2007.
Rotem, A. et al. "Single Cell Chip-Seq Using Drop-Based Microfluidics" Abstract #50. Frontiers of Single Cell Analysis, Stanford University Sep. 5-7, 2013.
Rotem, A. et al., "High-throughput single-cell labeling (Hi-SCL) for RNA-Seq using drop-based microfluidics" PLOS One (May 22, 2015) 0116328 (14 pages).
Ryan, et al. Rapid assay for mycobacterial growth and antibiotic susceptibility using gel microdrop encapsulation. J Clin Microbiol. Jul. 1995;33(7):1720-6.
Schirinzi et al., Combinatorial sequencing-by-hybridization: analysis of the NFI gene. Genet Test. 2006 Spring;10(1):8-17.
Schmitt, "Bead-based multiplex genotyping of human papillomaviruses", J. Clinical Microbiol., 44:2 504-512 (2006).
Sebat, et al. Strong association of de novo copy number mutations with autism. Science. Apr. 20, 2007;316(5823):445-9. Epub Mar. 15, 2007.
Seiffert, S. et al., "Smart microgel capsules from macromolecular precursors" J. Am. Chem. Soc. (2010) 132:6606-6609.
Shah, "Fabrication of mono disperse thermosensitive microgels and gel capsules in micro fluidic devices", Soft Matter, 4:2303-2309 (2008).
Shimkus et al. "A chemically cleavable biotinylated nucleotide: Usefulness in the recovery of protein-DNA complexes from avidin affinity columns" PNAS (1985) 82:2593-2597.
Shlien, et al. Copy number variations and cancer. Genome Med. Jun. 16, 2009;1(6):62. doi: 10.1186-gm62.
Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073-pnas.0802970105. Epub Aug. 6, 2008.
Simeonov et al., Single nucleotide polymorphism genotyping using short, fluorescently labeled locked nucleic acid (LNa) probes and fluorescence polarization detection. Nucleic Acids Res. Sep. 1, 2002;30(17):e91.
Sorokin et al., Discrimination between perfect and mismatched duplexes with oligonucleotide gel microchips: role of thermodyNamic and kinetic effects during hybridization. J Biomol Struct Dyn. Jun. 2005;22(6):725-34.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Tawfik, D.S. et al. "Man-made cell-like compartments for molecular evolution" Nature Biotech (Jul. 1998) 16:652-656.
Tewhey, R. et al., "Microdroplet-based PCR enrichment for large-scale targeted sequencing" Nature Biotech. (2009) 27(11):1025-1031 and Online Methods (11 pages).
Theberge, A.B, et al. Microdropelts in microfluidics: an evolving platform for discoveries in chemsitry and biology. Angew Chem Int Ed Engl. Aug. 9, 2010;49(34):5846-68. doi: 10.1002-anie.200906653.
Tonelli, C. et al., "Perfluoropolyether functional oligomers: unusual reactivity in organic chemistry" J. Fluorine Chem. (2002) 118:107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093-protein-gzq032. Epub May 31, 2010.
Turner, et al. "Methods for genomic partitioning" Annu Rev Genomics Human Genet. (2009) 10:263-284. doi: 10.1146-annurev-genom-082908-150112. Review.
Wagner, O et al., "Biocompatible fluorinated polyglycerols for droplet microfluidics as an alternative to PEG-based copolymer surfactants" Lab Chip DOI:10.1039-C5LC00823A. 2015.
Wang et al., Single nucleotide polymorphism discrimination assisted by improved base stacking hybridization using oligonucleotide microarrays. Biotechniques. 2003;35:300-08.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Weaver, J.C. et al. "Rapid clonal growth measurements at the single-cell level: gel microdroplets and flow cytometry", Biotechnology, 9:873-877 (1991).
Whitesides, "Soft lithography in biology and biochemistry", Annual Review of Biomedical Engineering, 3:335-373 (2001).
Williams, R. et al. "Amplification of complex gene libraries by emulsion PCR" Nature Methods (Jul. 2006) 3(7):545-550.
Woo, et al. G-C-modified oligodeoxynucleotides with selective complementarity: synthesis and hybridization properties. Nucleic Acids Res. Jul. 1, 1996;24(13):2470-5.
Xia, "Soft lithography", Annual Review of Material Science, 28: 153-184 (1998).
Yamamoto, et al. Chemical modification of Ce(IV)-EDTA-base artificial restriction DNa cutter for versatile manipulation of doulbestranded DNa. Nucleic Acids Research. 2007; 35(7):e53.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functioNalized nucleosides via the RAFT process. Biomacromolecules. Nov. 2008;9(11):3321-31. doi: 10.1021-bm800867n. Epub Oct. 9, 2008.
Zhao, J., et al., "Preparation of hemoglobin-loaded Nano-sized particles with porous structure as oxygen carriers," Biomaterials, vol. 28, pp. 1414-1422 (2007).
Zhu, S. et al., "Synthesis and self-assembly of highly incompatible polybutadienepoly(hexafluoropropylene oxide) diblock copolymers" J. Polym. Sci. (2005) 43:3685-3694.
Zimmermann et at., Microscale production of hybridomas by hypo-osmolar electrofusion. Human Antibodies Hybridomas. Jan. 1992;3(1):14-8.
Zong, C. et al. "Genome-wide detection of single-nucleotide and copy-number variations of a single human cell" Science. Dec. 21, 2012;338(6114):1622-6. doi: 10.1126-science.1229164.

* cited by examiner

| | |
|---|---|
| Nucleic acid sequencing dataset 1 | 126-1 |
|   Header | 302 |
|     Component list | 304 |
|     Version | 306 |
|     ⋮ | |
|   Synopsis | 308 |
|     Summary | 310 |
|     Index to variant call data | 312 |

| Genome range 314-1 | Offset 316-1 |
|---|---|
| ⋮ | |
| Genome range 314-L | Offset 316-L |

| | |
|---|---|
|     Phase block track | 318 |
|     Refseq index | 319 |
|     Gene track | 320 |
|     Exon track | 322 |
|     Index to read (e.g. BAM) data | 324 |
|       Chromosome 1 | 326-1 |

| Length 1 | Chromosome offset 1 | File Offset 1 | 328-1 |
|---|---|---|---|
| ⋮ | ⋮ | ⋮ | |
| Length Q | Chromosome offset Q | File Offset Q | 328-Q |

| | |
|---|---|
|       ⋮ | |
|       Chromosome N | 326-N |
|     Structural variant dataset track | 330 |
|     Index to target dataset | 332 |

| Chromosome No. | Start 1 | End 1 | Offset 1 | 334-1 |
|---|---|---|---|---|
| ⋮ | ⋮ | ⋮ | ⋮ | |
| Chromosome No. | Start K | End K | Offset K | 334-K |

| | |
|---|---|
|     Index to fragments dataset | 336 |

| Chromosome No. | Start 1 | End 1 | Offset 1 | 338-1 |
|---|---|---|---|---|
| ⋮ | ⋮ | ⋮ | ⋮ | |
| Chromosome No. | Start M | End M | Offset M | 338-M |

| | |
|---|---|
|   Data | 340 |
|     Target dataset | 342 |
|     Fragment dataset | 344 |
|     … | |
| ⋮ | |
| Nucleic acid sequencing dataset N | 126-N |

*FIG. 3*

```
{
    "Name" : "phase_data",                  (402)
    "TrackData" : [                         (408)
        {                                   (410-1)
            "Info" : {
                "PhaseASNP" : 0,
                "UnPhasedSNP" : 0,
                "PhaseBSNP" : 5
            },
            "Name" : "3",
            "Stop" : 35,
            "Chromosome" : "chr1",
            "Start" : 30
        },
        {                                   (410-2)
            "Start" : 37,
            "Info" : {
                "UnPhasedSNP" : 0,
                "PhaseBSNP" : 3,
                "PhaseASNP" : 0
            },
            "Stop" : 40,
            "Chromosome" : "chr1",
            "Name" : "6"
        }
    ],
    "Itree" : {
        "chrl" : {                          422-1
            "RightTree" : null,
            "MidPoint" : 38,
            "LeftTree" : {
                "RightTree" : null,
                "MidPoint" : 32 ,
                "LeftTree" : null,
                "Data Here" : [
                    {
                        "Left" : 30,
                        "Right" : 35,
                        "Name" : "0"
                    },
                ]
            },
            "DataHere" : [
                {
                    "Right" : 40,
                    "Left": 37,
                    "Name" : "1"
                }
            ]
        },
    "Dictionary" {
        "3" : 0,
        "6" : 1
    }
}
```

```
{
    "Dictionary" : { 602
        "CHR4: : 4,
        "CHR1-SILLY" : 1,
        "CHR1: : 0,    604 : 606
        "CHR5" : 5,
        "CHR3-SILLY" : 3,
        "CHR2" : 2
    },
    "Name" : "gene-track",
    "TrackData" : [ 608
        {
            "Chromosome" : "chr1",
610-1       "Info" : "
                "AlternateName" : "x",
                "SNPCount" : 11,
                "Direction" : "-"
            },
            "Name" : "CHR1",
            "Stop" : 400,
        },
        {
610-2       "Chromosome" : "chr1",
            "Start" : 1000,
            "Stop" : 4000,
            "Name" : "CHR1-SILLY",
            "Info" : {
                "Direction" : "-",
                "AlternateName" : "x",
                "SNPCount" : 0
            }
        },
        {
            "Chromosome" : "chr2",
610-3       "Name" : "CHR2",
            "Info" : {
                "SNPCount" : 1,
                "AlternateName" : "x",
                "Direction" : "-"
            },
            "Start" : 10,
            "Stop" : 400
        },
        {
            "Start" : 10,
610-4       "Stop" : 4000,
            "Name" : "CHR3-SILLY",
            "Info" : {
                "Direction" : "-"
                "SNPCount" : 0,
                "AlternateName" : "x",
            },
            "Chromosome" : "chr3"
        },
        {
            "Chromosome" : "chr11",
610-5       "Name" : "CHR4",
            "Info" : {
                "SNPCount" : 1,
                "AlternateName" : "x",
                "Direction" : "-"
            },
            "Start" : 10,
            "Stop" : 400
        },
        {
610-6       "Name" : "CHR5",
            "Info" : {
                "SNPCount" : 1,
                "AlternateName" : "x",
                "Direction" : "-"
            },
            "Start" : 10,
            "Stop" : 400
            "Chromosome" : "chr21"
        }
    ],
    "Itree" : { 628
        "chr3" : {
            "RightTree" : null,
630-1       "DataHere" : [
                {
                    "Name" : "3"
                    "Left" : 1000,
                    "Right" : 4000
                }
            "LeftTree" : null,
            "MidPoint" : 2500
```

FROM FIG. 7

```
        },
        "chr11" : {
            "LeftTree" : null,
630-2       "MidPoint" : 205,
            "RightTree" : null,
            "DataHere" : [
                {
                    "Right" : 400,
                    "Left" : 10,
                    "Name" : "4"
                }
            ]
        },
        "chr1" : {
            "DataHere" : [
630-3           {
                    "Name" : "1",
                    "Right" : 4000,
                    "Left" : 1000
                }
            ]
            "RightTree" : null,
            "MidPoint" : 2500,
            "LeftTree" : {
                "DataHere" : [
                    {
                        "Left" : 10,
                        "Right" : 400,
                        "Name" : "0"
                    }
                ],
                "RightTree" : null,
                "MidPoint" : 205,
                "LeftTree" : null
            }
        },
        },
        "chr21" : {
630-4       "DataHere" : [
                {
                    "Left" : 10,
                    "Right" : 400,
                    "Name" : "5"
                }
```

```
            ]
            "RightTree" : null,
            "MidPoint" : 205,
            "LeftTree" : null
        },
        "chr2" : {
            "LeftTree" : null,
630-5       "MidPoint" : 205,
            "RightTree" : null,
            "DataHere" : [
                {
                    "Left" : 10,
                    "Right" : 400,
                    "Name" : "2"
                }
            ]
        }
    }
}
```

*FIG. 7B*

```
810-1 {
  812  "Chromosome" : "chr16",
  816  "Stop" : 71320834,
       "Name" : "BRK_chr16_71316475_chr5_115237536",
  820  "Info" : {
           "Chromosome1" : "chr16"
           "Stop2" : 115250206,
           "Stop1" : 71320834,
           "Start2" : 115237536,
           "Start1" : 71316475,
           "Quality" : 73,
           "Name" : "BRK_chr16_71316475_chr5_115237536",
           "Chromosome2" : "chr5",
           "Info" : {
               "SEG_DUP" : ".",
               "NMATES1 : "2",
               "NSPLIT" : "0",
               "BLACK_FRAC" : "nan",
               "BCOV" : "17",
               "BLACK_DIST2" : "10366.0",
               "TYPE" : "UNK",
               "BLACK_DIST1" : "58024.0",
               "NBCS1" : "270",
               "NMATES2" : "1",
               "MATCHES" : ".",
               "NPAIRS" : "0",
               "NBCS2" : "217",
               "RP_LR" : "0.0",
               "ORIGINALQ" : "53"
           },
           "Filters" : [ ]
       },
  814  "Start" : 71316475
  },
```

*FIG. 9*

| Variant call data | | | |
|---|---|---|---|
| Genome range 1 | | | |
| | Position 1 | Data 1 | |
| | ⋮ | | |
| | Position Q | Data Q | |
| Genome range 2 | | | |
| | Position 1 | Data 1 | |
| | ⋮ | | |
| | Position P | Data P | |
| ⋮ | | | |
| Genome range M | | | |

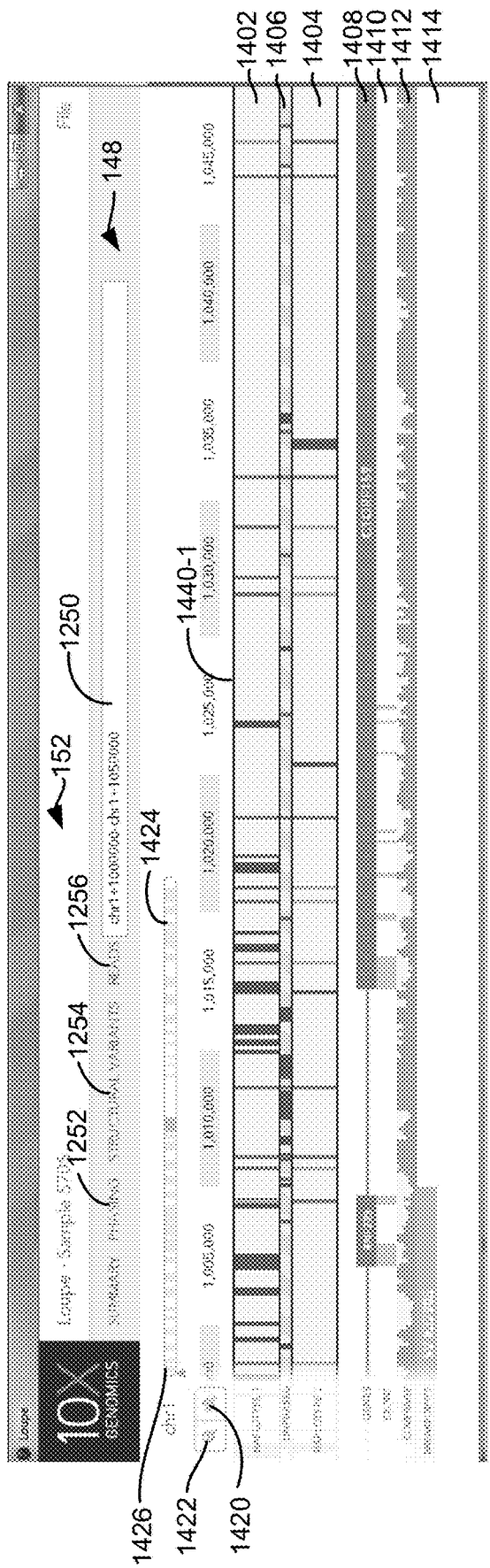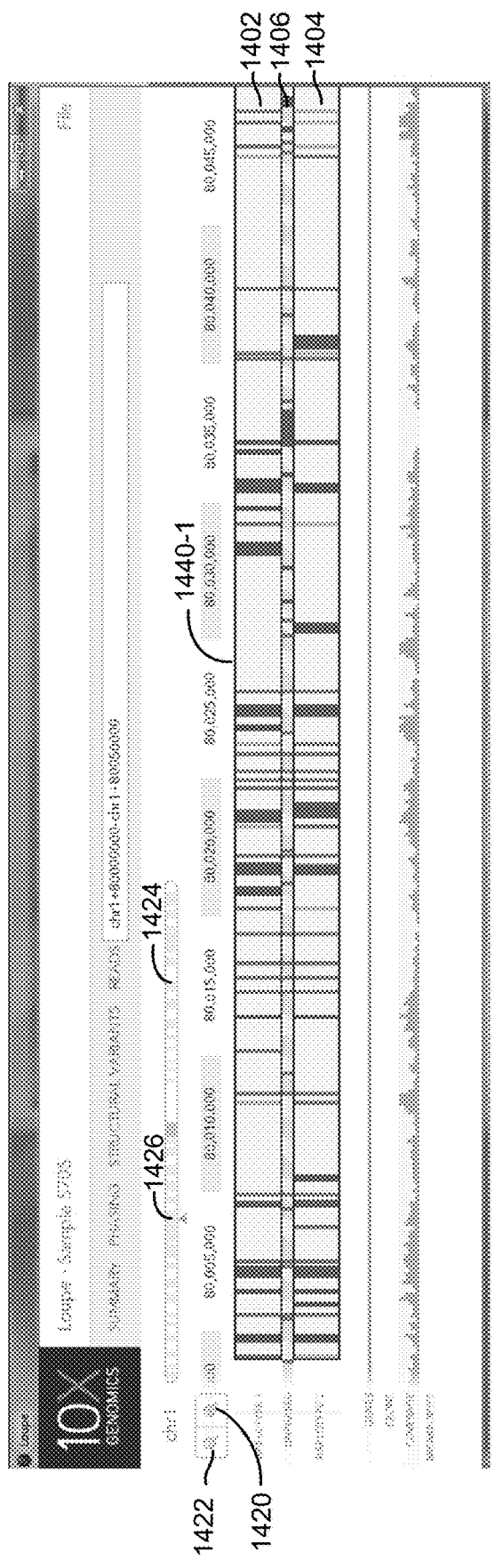
FIG. 14A
FIG. 14B

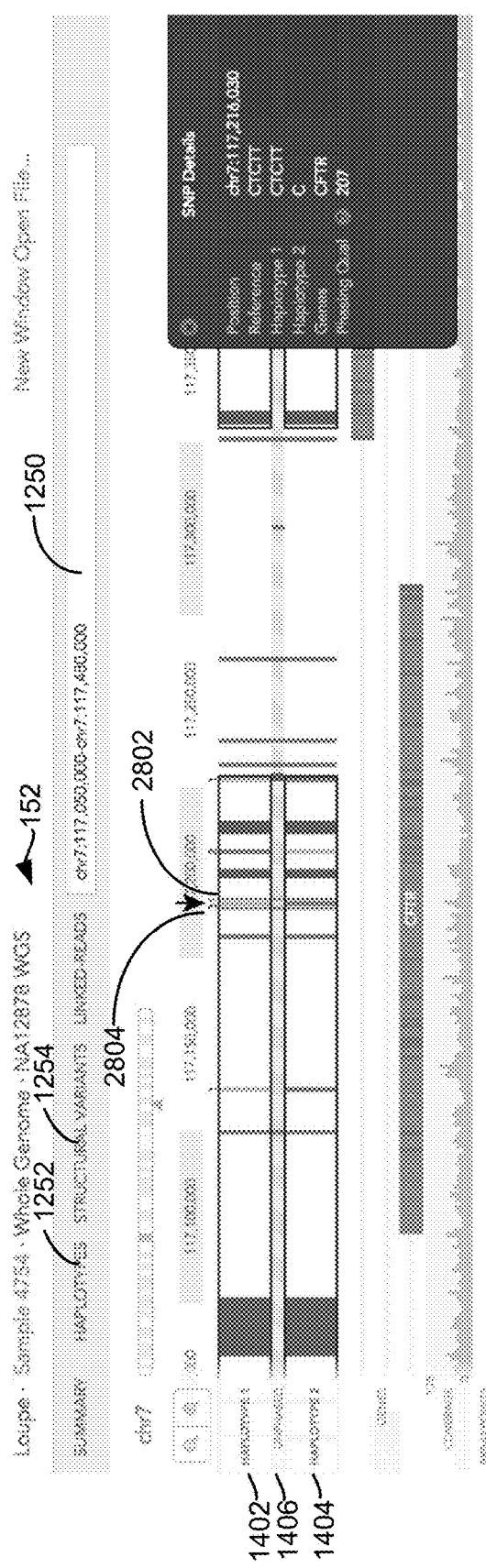
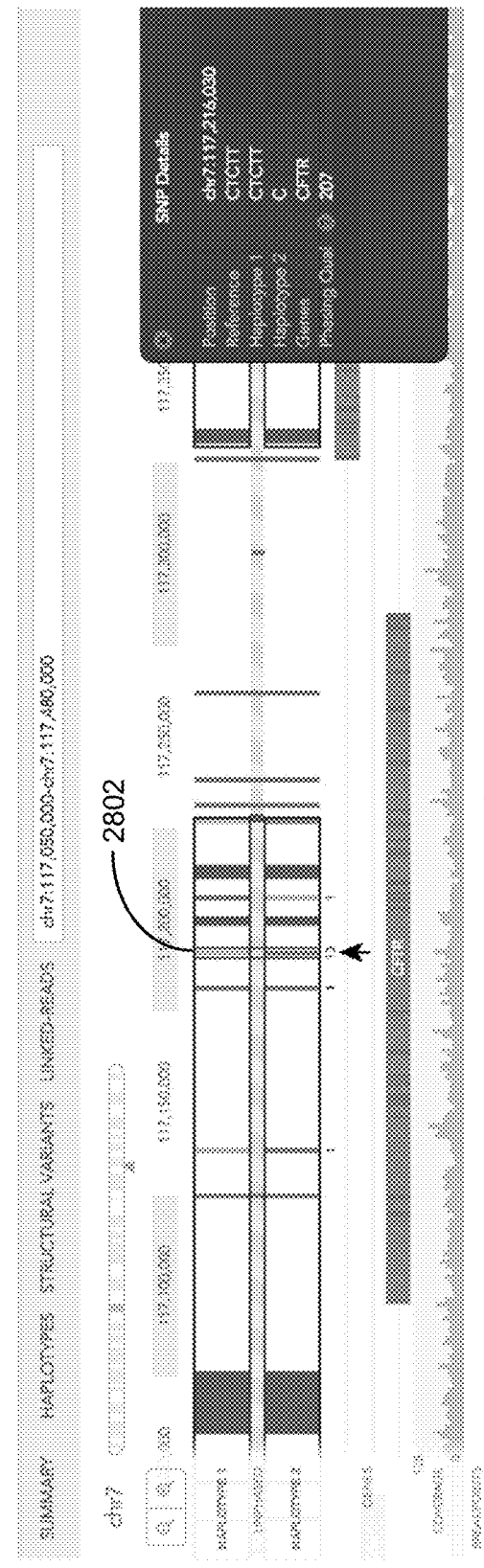
FIG. 28A
FIG. 28B

SYSTEMS AND METHODS FOR VISUALIZING STRUCTURAL VARIATION AND PHASING INFORMATION

RELATED APPLICATIONS

This application is related to U.S. Patent Application No. 62/120,873, entitled "Systems and Methods for Visualizing Structural Variation and Phasing Information," filed Feb. 25, 2015, which is hereby incorporated by reference herein in its entirety.

This application is also related to U.S. Patent Application No. 62/102,926, entitled "Systems and Methods for Visualizing Structural Variation and Phasing Information," filed Jan. 13, 2015, which is hereby incorporated by reference herein in its entirety.

TECHNICAL FIELD

This specification describes technologies relating to visualizing structural variation and phasing information in nucleic acid sequencing data.

BACKGROUND

Haplotype assembly from experimental data obtained from human genomes sequenced using massively parallelized sequencing methodologies has emerged as a prominent source of genetic data. Such data serves as a cost-effective way of implementing genetics based diagnostics as well as human disease study, detection, and personalized treatment.

The long-range information provided by such massively parallelized sequencing methodologies is disclosed, for example, in U.S. Patent Application No. 62/072,214, filed Oct. 29, 2014, entitled "Analysis of Nucleic Acid Sequences." Such techniques greatly facilitate the detection of large-scale structural variations of the genome, such as translocations, large deletions, or gene fusions. Other examples include, but are not limited to the sequencing-by-synthesis platform (ILLUMINA), Bentley et al., 2008, "Accurate whole human genome sequencing using reversible terminator chemistry, Nature 456:53-59; sequencing-by-litigation platforms (POLONATOR; ABI SOLiD), Shendure et al., 2005, "Accurate Multiplex Polony Sequencing of an Evolved bacterial Genome" Science 309:1728-1732; pyrosequencing platforms (ROCHE 454), Margulies et al., 2005, "Genome sequencing in microfabricated high-density picoliter reactors," Nature 437:376-380; and single-molecule sequencing platforms (HELICOS HELISCAPE); Pushkarev et al., 2009, "Single-molecule sequencing of an individual human genome," Nature Biotech 17:847-850, (PACIFIC BIOSCIENCES) Eid et al., "Real-time sequencing form single polymerase molecules," Science 323:133-138, each of which is hereby incorporated by reference in its entirety.

The availability of haplotype data spanning large portions of the human genome, the need has arisen for ways in which to efficiently work with this data in order to advance the above stated objectives of diagnosis, discovery, and treatment, particularly as the cost of whole genome sequencing for a personal genome drops below $1000. To computationally assemble haplotypes from such data, it is necessary to disentangle the reads from the two haplotypes present in the sample and infer a consensus sequence for both haplotypes. Such a problem has been shown to be NP-hard. See Lippert et al., 2002, "Algorithmic strategies for the single nucleotide polymorphism haplotype assembly problem," Brief. Bionform 3:23-31, which is hereby incorporated by reference.

The assembly view Consed supports visualization of reads obtained from the above-identified sequencing methods. See Gordon 1998, "Consed: A graphical tool for sequencing finishing," Genome Research 8:198-202.

Another visualization tool is EagleView. See Huang and Marth, 2008, "EagleView: A genome assembly viewer for next-generation sequencing technologies," Genome Research 18:1538-1543.

Still another such viewer is HapEdit. See Kim et al., "HapEdit: an accuracy assessment viewer for haplotype assembly using massively parallel DNA-sequencing technologies." Nucleic Acids Research, 2011, 1-5. HapEdit provides tools for assessing the accuracy of Haplotype assemblies and permits a user to fit the composition rates of reads sequence by numerous different sequencing technologies.

While the above-disclosed programs are each significant advancements in their own right, they do not adequately address the need in the art for tools for visually assessing structural variants (e.g., deletions, duplications, copy-number variants, insertions, inversions, translocations, long terminal repeats (LTRs), short tandem repeats (STRs), and a variety of other useful characterizations) in sequencing data.

SUMMARY

Technical solutions (e.g., computing systems, methods, and non-transitory computer readable storage mediums) for visually assessing structural variants are provided. With platforms such as those disclosed in U.S. Patent Application No. 62/072,214, filed Oct. 29, 2014, entitled "Analysis of Nucleic Acid Sequences," which is hereby incorporated by reference, the genome is fragmented and partitioned and barcoded prior to the target identification. Therefore the integrity of the barcode information is maintained across the genome. The barcode information is used to identify potential structural variation breakpoints by detecting regions of the genome that show significant barcode overlap. They are also used to obtain phasing information.

The following presents a summary of the invention in order to provide a basic understanding of some of the aspects of the invention. This summary is not an extensive overview of the invention. It is not intended to identify key/critical elements of the invention or to delineate the scope of the invention. Its sole purpose is to present some of the concepts of the invention in a simplified form as a prelude to the more detailed description that is presented later.

One aspect of the present disclosure is a system for providing structural variation or phasing information over a network connection to a remote client computer. The system comprises one or more microprocessors, a persistent memory and a non-persistent memory. The persistent memory (e.g., a hard drive) and the non-persistent memory (e.g., RAM memory) collectively store one or more nucleic acid sequence datasets. Each respective nucleic acid sequencing dataset in the one or more nucleic acid sequence datasets corresponds to at least one target nucleic acid in a respective sample in a plurality of samples. The respective sample is associated with a reference genome of a species that may serve as a benchmark for analysis of the respective sample in some embodiments. For instance, in some embodiments the respective sample is mapped to the reference genome and the reference genome is thereby used as a template (reference) to parse queries to visualize portions of the respective sample. For instance, in some embodiments a sample is from a human subject. In such instance, a human genome (as opposed to a genome from a different species) serves as the reference genome and the respective sample is mapped to the human genome. In this way, requests to visual sequences or sequence variations in certain human chromosomes, or portions thereof from the sample, can be interpreted and handled using the disclosed systems and methods, based on such mapping to the reference genome.

The respective nucleic acid sequencing dataset comprises (i) a header, (ii) a synopsis, and (iii) a data section. The data section comprises a plurality of aligned sequence reads from the sample and information about each variant call made. Advantageously, the data section is extensible and can store additional data. Each respective sequencing read in the plurality of sequencing reads comprises a first portion that corresponds to a subset of at least one target nucleic acid in the respective sample and a second portion that encodes a respective identifier for the respective sequencing read in a plurality of identifiers. Each respective identifier is independent of the sequence of the at least one target nucleic acid. Sequencing reads in the plurality of sequencing reads collectively include the plurality of identifiers.

The persistent memory and the non-persistent memory further collectively store one or more programs that use the one or more microprocessors to provide a haplotype visualization tool to a client for installation on the remote client computer. The system receives a request, sent from the client over a network connection (e.g., Internet), for structural variation or phasing information using a first dataset in the one or more datasets. Responsive to receiving the request, the request is automatically filtered by performing a method comprising loading the header and the synopsis of the first dataset into the non-persistent memory if not already loaded into the non-persistent memory while retaining the data section in persistent memory. In the method, the request is compared (analyzed against) the synopsis of the first dataset thereby identifying one or more portions of the data section of the first dataset. These one or more identified portions of the data section are, in turn, loaded into non-persistent memory. Structural variation or phasing information is formatted for display on the client computer using the first dataset. Then the formatted structural variation or phasing information is transmitted over the network connection to the client device for display on the client device.

In some embodiments, the header delineates a plurality of components in the respective nucleic acid sequencing dataset. In some embodiments the plurality of components comprises two or more components, three or more components, four or more components or five or more components selected from the group consisting of a summary, an index to variant call data, a phase block track, a refseq index track, a gene track, an exon track, an index to read data, a structural variant dataset track, an index to a target dataset, and an index to a fragment dataset.

In some embodiments, the plurality of components comprises the summary and this summary comprises two or more items, three or more items, four or more items, five or more items, or six or more items in the group consisting of: a percentage of known SNPs phased in the respective nucleic acid sequencing dataset, a longest phase block in the respective nucleic acid sequencing dataset, a number of unique barcodes used in the respective nucleic acid sequencing dataset, an average fragment length in the respective nucleic acid sequencing dataset, a mean of the average fragment length in the respective nucleic acid sequencing dataset, a percentage of fragments greater than a lower threshold in the respective nucleic acid sequencing dataset, a fragment length histogram in the respective nucleic acid sequencing dataset, an N50 phase block size in the respective nucleic acid sequencing dataset, a phase block histogram in the respective nucleic acid sequencing dataset, a number of sequence reads represented by respective the nucleic acid sequencing dataset, a median insert size in the respective nucleic acid sequencing dataset, a median depth in the respective nucleic acid sequencing dataset, a percent of the target genome with zero coverage in the respective nucleic acid sequencing dataset, a mapped reads percentage for the respective nucleic acid sequencing dataset, a PCR duplication percentage for the respective nucleic acid sequencing dataset, a coverage histogram for the in the respective nucleic acid sequencing dataset, an identity of a test nucleic acid that forms the basis for the respective nucleic acid sequencing dataset, a genome source for the respective nucleic acid sequencing dataset, a sex of an organism that originated the at least one test nucleic acid of the respective nucleic acid sequencing dataset, a sex of the organism that originate the respective sample of the in the respective nucleic acid sequencing dataset, a dataset file format version of the in the respective nucleic acid sequencing dataset, and a pointer to a plurality of structural variant calls made for the respective nucleic acid sequencing dataset. Advantageously, as this non-limiting example of the list of information indicates, the disclosed nucleic acid sequencing datasets can contain arbitrary bits of metadata (e.g., annotation data) that might be of user interest in along with sequencing data.

In some embodiments, the plurality of components comprises the index to variant call data that provides a correspondence between respective ranges of the genome of the species to offsets in the data section where variant call data for the respective ranges is found.

In some embodiments, the plurality of components comprises the phase block track. The phase block track comprises (i) a dictionary and (ii) a track data section comprising phase information for one or more chromosomes in the genome of the species. In some embodiments, the dictionary comprises a plurality of names, and for each respective name in the plurality of names, an offset into the track data where records for the corresponding name are found. In some embodiments, the track data section comprises a plurality of records and wherein each record in the plurality of records represents a phase block in the target nucleic acid. In some embodiments, the tract data section is in the JSON file format.

In some embodiments, each respective record in the plurality of records specifies (i) a chromosome number corresponding to the respective record, (ii) a position where the phase block starts on the chromosome, (iii) a position where the phase block ends, (iv) a unique name for the record, and (v) phasing information about the phase block.

In some embodiments, each respective record in the plurality of records is represented by a node in a plurality of nodes in a respective interval tree in a plurality of interval trees, and each interval tree in the plurality of interval trees represents a chromosome in a plurality of chromosomes for the species. In some such embodiments, a node in the plurality of nodes of a first interval tree in the plurality of interval trees stores a midpoint of the node, the midpoint of the node is a position of the midpoint, on the corresponding chromosome, of the phase block corresponding to the node, each respective node in the plurality of nodes of the first interval tree has a link to a left child node, which corresponds to the phase block immediately to the left of (i.e., numerically less than) the phase block represented by the respective node in the genome of the species, each respective node in the plurality of nodes of the first interval tree has a link to a right child node, which corresponds to the phase block immediately to the right of (i.e., numerically greater than) the phase block represented by the respective node in the genome of the species, each respective node in the plurality of nodes of the first interval tree has a sorted set of nodes that represent phase blocks that overlap the midpoint of the respective node sorted by left hand position of such phase block, and each respective node in the plurality of nodes of the first interval tree has a sorted set of nodes that represent phase blocks that overlap the midpoint of the respective node sorted by right hand position of such phase blocks. In some such embodiments, each respective node in the plurality of nodes of the first interval tree further includes a name, which is an offset in the track data section to the record in the plurality of records that contains phase information for the phase block corresponding to the respective node.

In some embodiments, the header further comprises the version of the dataset structure used by the nucleic acid sequencing dataset. In some embodiments, the plurality of components comprises the refseq index, and the refseq index comprises an index of a plurality of molecular variation identifiers that are called in the sample. In some such embodiments, each respective molecular variation identifier in the plurality of molecular variation identifiers is dbSNP identifier.

In some embodiments, the plurality of components comprises the gene track. In such embodiments, the gene track comprises a plurality of genes and, for each respective gene in the plurality of genes, a number of single nucleotide polymorphisms in the respective gene.

Another aspect of the present disclosure provides a system for processing program output over a network connection using a local computer, where the local computer comprises one or more microprocessors, and a memory that stores one or more programs. The one or more programs use the one or more microprocessors to execute a method in accordance with a first operating system running on the local computer. In the method a first instance of a first program is invoked. Then, there is obtained through the first instance of the first program from a user, a login and a password to a user account on a remote computer. This is used to log the user into the user account on the remote computer automatically (using the login and the password provided by the first instance of the first program) across a network connection between the local computer and the remote computer. Responsive to successful login on the remote computer, there automatically sent, without human intervention, a second instance of the first program configured to auto-install on the remote computer upon transmission to the remote computer when the remote computer does not already have the first program available in the users account. Next, there is received from the remote computer a request to open a panel within the first instance of the first program. The panel is originated by the second instance of the first program running on the remote computer. The panel solicits input from the user for controlling the second instance of the first program. Responsive to receiving input from the user for controlling the second instance of the first program in the panel on the local computer, the input is sent to the second instance of the first program on the remote computer across the network connection (e.g., wireless or wired connection). Next, there is received, from the remote computer across the network connection, output from the second instance of the first program responsive to the input. This output is displayed at the local computer.

Another aspect of the present disclosure provides a system for viewing nucleic acid sequencing data. The system comprises one or more microprocessors and a memory. The memory stores one or more programs that use the one or more microprocessors to obtain a nucleic acid sequencing dataset corresponding to at least one target nucleic acid in a sample. The nucleic acid sequencing dataset comprises a plurality of sequencing reads from the sample. Each respective sequencing read in the plurality of sequencing reads comprises a first portion that corresponds to a subset of at least one target nucleic acid in the sample and a second portion that encodes a respective identifier (e.g., bar code) for the respective sequencing read in a plurality of identifiers. Each respective identifier is independent of the sequence of the at least one target nucleic acid. The plurality of sequencing reads collectively includes the plurality of identifiers. A visualization tool is displayed. A request is obtained from a user through the visualization tool. The request specifies a genomic region represented by the nucleic acid sequencing dataset. Responsive to obtaining the request, the request is parsed by obtaining a plurality of sequencing reads within the genomic region from the nucleic acid sequencing dataset. A scan window is run against the plurality of sequencing reads thereby creating a plurality of windows, each respective window of the plurality of windows corresponding to a different region of the genomic region and including an identity of each identifier of each sequencing read in the different region of the genomic region in the nucleic acid sequencing dataset. A two dimensional heat map that represents each possible window pair in the plurality of windows is displayed. Each respective window pair is displayed in the two dimensional heat map as a color selected from a color scheme based upon the number of identifiers in common in the respective window pair.

Various embodiments of systems, methods and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the drawings.

FIG. 3 provides an overview of a nucleic acid sequencing dataset in accordance with an embodiment of the present disclosure.

FIG. 5 illustrates an example phase block track in accordance with some embodiments.

FIGS. 7A and 7B illustrate an example gene track in accordance with some embodiments.

FIG. 9 illustrates an example structural variant dataset track in accordance with some embodiments.

FIG. 11 illustrates variant call data within a nucleic acid sequencing dataset in accordance with some embodiments.

FIG. 14A illustrates a screen shot of a phase visualization module in a haplotype visualization tool in accordance with some embodiments.

FIG. 14B illustrates another screen shot of a phase visualization module in a haplotype visualization tool in accordance with some embodiments.

FIG. 28A illustrates another aspect of a phase visualization module in a haplotype visualization tool in accordance with some embodiments.

FIG. 28B illustrates still another aspect of a phase visualization module in a haplotype visualization tool in accordance with some embodiments.

FIG. 34 illustrates a structural variants module in a haplotype visualization tool in accordance with some embodiments in which a sequence read filter is turned on.

DETAILED DESCRIPTION

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event ("or" in response to detecting (the stated condition or event)," depending on the context.

The implementations described herein provide various technical solutions to detect a structural variant (e.g., deletions, duplications, copy-number variants, insertions, inversions, translocations, long terminal repeats (LTRs), short tandem repeats (STRs), and a variety of other useful characterizations) in sequencing data of a test nucleic acid obtained from a biological sample. Details of implementations are now described in relation to the Figures.

Figure 1:
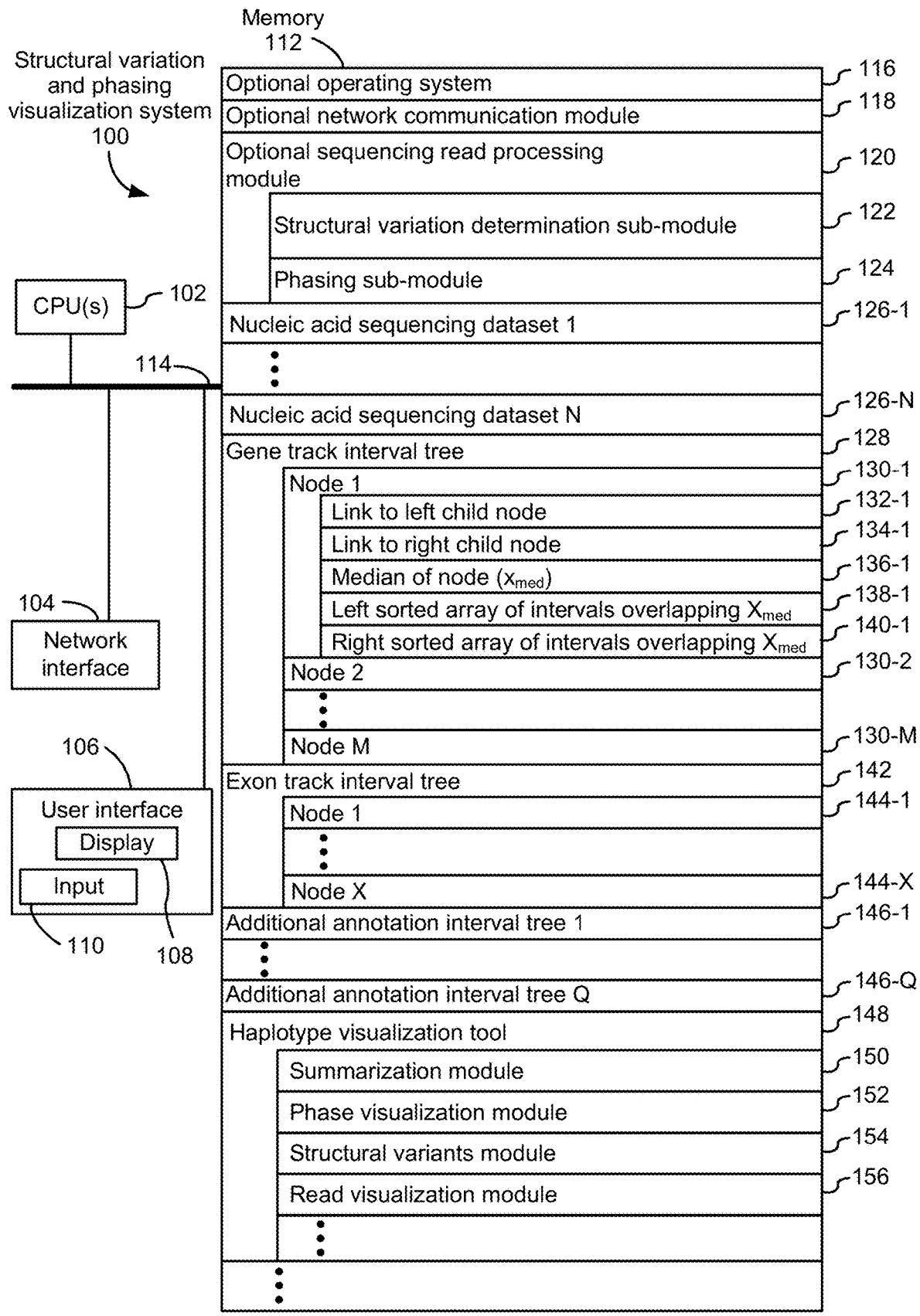
FIG. 1 is an example block diagram illustrating a computing device in accordance with some implementations.

FIG. 1 is a block diagram illustrating a structural variant and phasing visualization system 100 in accordance with some implementations. The device 100 in some implementations includes one or more processing units CPU(s) 102 (also referred to as processors), one or more network interfaces 104, a user interface 106, a memory 112, and one or more communication buses 114 for interconnecting these components. The communication buses 114 optionally include circuitry (sometimes called a chipset) that interconnects and controls communications between system components. The memory 112 typically includes high-speed random access memory, such as DRAM, SRAM, DDR RAM, ROM, EEPROM, flash memory, CD-ROM, digital versatile disks (DVD) or other optical storage, magnetic cassettes, magnetic tape, magnetic disk storage or other magnetic storage devices, other random access solid state memory devices, or any other medium which can be used to store desired information; and optionally includes non-volatile memory, such as one or more magnetic disk storage devices, optical disk storage devices, flash memory devices, or other non-volatile solid state storage devices. The memory 112 optionally includes one or more storage devices remotely located from the CPU(s) 102. The memory 112, or alternatively the non-volatile memory device(s) within the memory 112, comprises a non-transitory computer readable storage medium. In some implementations, the memory 112 or alternatively the non-transitory computer readable storage medium stores the following programs, modules and data structures, or a subset thereof:

- an optional operating system 116, which includes procedures for handling various basic system services and for performing hardware dependent tasks;
- an optional network communication module (or instructions) 118 for connecting the device 100 with other devices, or a communication network;
- an optional sequencing read processing module 120 for processing sequencing reads, including a structural variation determination sub-module 120 for identifying structural variations in a genetic sample from a single organism of a species and a phasing sub-module 124 for identifying the haplotype of each sequencing read of the genetic sample;
- one or more nucleic acid sequencing datasets 126, each such dataset obtained using a genetic sample from a single organism of a species;
- gene annotation data, optionally in the form of a gene track interval tree 128;
- exon annotation data, optionally in the form of an exon track interval tree 142;
- one or more additional sources of annotation data, optionally in the form of interval trees 146;
- a haplotype visualization tool 148 for visualizing structural variation and phasing information in nucleic acid sequencing data, including any combination of one or more of a summarization module 150, a phase visualization module 152, a structural variants (visualization) module 154, and a read visualization module 156.

In some implementations, the user interface 106 includes an input device (e.g., a keyboard, a mouse, a touchpad, a track pad, and/or a touch screen) 100 for a user to interact with the system 100 and a display 108.

In some implementations, one or more of the above identified elements are stored in one or more of the previously mentioned memory devices, and correspond to a set of instructions for performing a function described above. The above identified modules or programs (e.g., sets of instructions) need not be implemented as separate software programs, procedures or modules, and thus various subsets of these modules may be combined or otherwise re-arranged in various implementations. In some implementations, the memory 112 optionally stores a subset of the modules and data structures identified above. Furthermore, in some embodiments, the memory stores additional modules and data structures not described above. In some embodiments, one or more of the above identified elements is stored in a computer system, other than that of system 100, that is addressable by system 100 so that system 100 may retrieve all or a portion of such data when needed.

Although FIG. 1 shows a "structural variation and phasing visualization system 100," the figure is intended more as functional description of the various features which may be present in computer systems than as a structural schematic of the implementations described herein. In practice, and as recognized by those of ordinary skill in the art, items shown separately could be combined and some items could be separated.

Figure 31:
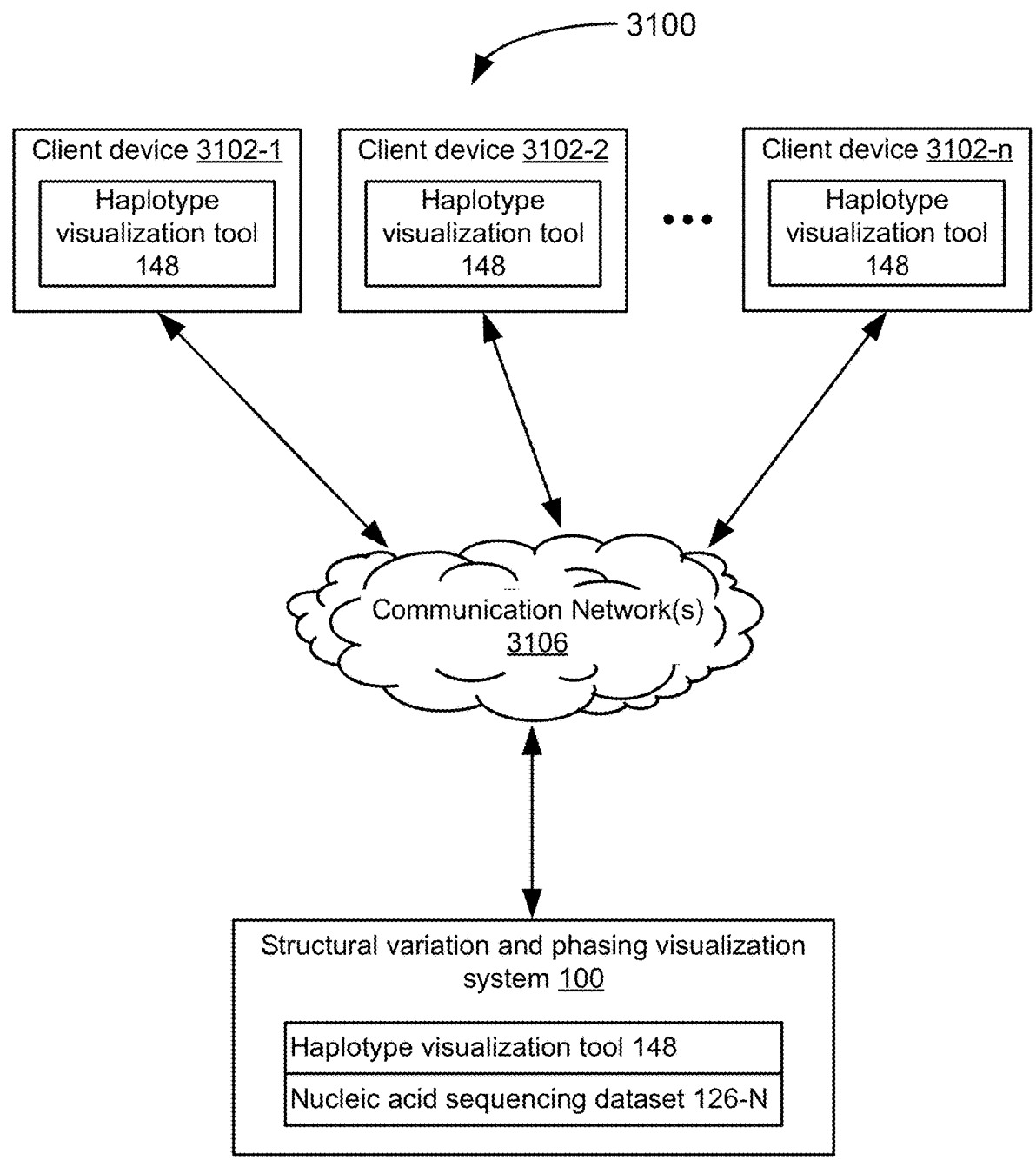
FIG. 31 is an example block diagram illustrating a computing system in accordance with some implementations.

Advantageously, because the nucleic acid sequence datasets 126 are large in typical embodiments (e.g., 1 gigabyte or greater, 5 gigabytes or greater, or 10 gigabytes or greater), in some embodiments the structural variation and phasing visualization system 100 is part of a system that includes one or more client devices 3102 that are in electronic communication with the structural variation and phasing visualization system 100 of FIG. 1 across a communication network 3106. Such a network topology allows scientists and other users to use one of several network based technologies to run the haplotype visualization tool 148 on system 100, which in typical embodiments is a powerful server computer, but view the results on client device 3102, which can be, for example, a laptop computer. Any form of network technology for implementing this network topology is encompassed within the present disclosure. For instance X-windows session forwarding (not shown in FIG. 31) is used in some embodiments. In other embodiments, the Internet (web) is used. In particular, a browser application is run on the client device 3102.

The process of running a program on a remote computer (e.g., in system 3100, the structural variation and phasing visualization system 100 is considered remote) and viewing the results on a client device 3102 (e.g., desktop or laptop) is cumbersome. A user must generally (i) install certain parts of the program on their computer 3102 and other parts on the server 100, (ii) use SSH or firewall software to create a open network port connecting the two computers (system 3102 to client device 100), and (iii) independently start different parts of the program on different systems. For example, a May 17, 2014, Trackets Blog post titled "SSH Tunnel—Local and Remote Port Forwarding Explained With Examples," which is hereby incorporated by reference, explains one way of setting up forwarding. The present disclosure incorporates such techniques. However, advantageously, in some embodiments, the present disclosure affords solutions to the above-disclosed networking techniques, which seeks to automate and improve upon the processes described above. Once a user has installed the haplotype visualization tool 148 on their client device 3102, they only need to provide the tool 148 with their credentials (e.g., user-name and password) for the remote computer (structural variation and phasing visualization system 100) that has the data and computational facilities to run the haplotype visualization tool 148. For instance, in some embodiments, referring to FIG. 32, the user running the haplotype visualization tool 148 on client 3102 will be provided with the challenge 3200 that includes a query for the server name or address 3204, the user's name 3206, an optional SSH key file (to enable encrypted connection) 3208, an optional SSH key password 3210, and a work location 3212 on the server. The instance of the haplotype visualization tool 148 on their client device 3102 then connects to the remote computer 100 and authenticates as the user using the provided credentials. Using that connection, it installs the haplotype visualization tool 148 on the remote computer, starts it, and configures any necessary network port forwarding. Once the haplotype visualization tool has done this, it opens up a new window on the client device 3102 that is "connected" to the haplotype visualization tool running on the remote structural variation and phasing visualization system. Of particular note, in such embodiments, the haplotype visualization tool 148 on the client device 3102 includes in a copy of itself that is intended to run on the structural variation and phasing visualization system 100. In some embodiments, the structural variation and phasing visualization system 100 is running a first operating system and the client device 3102 is running a second operating system. In some embodiments, the first operating system and the second operating system are the same. In some embodiments, the first operating system and the second operating system are different. In some embodiments, the first operating system is one of iOS, DARWIN, RTXC, LINUX, UNIX, OS X, or WINDOWS, and the second operating system is other than the first operating system and one of iOS, DARWIN, RTXC, LINUX, UNIX, OS X, or WINDOWS. In the disclosed embodiment, the haplotype visualization tool 148 running on the client device 3102 copies the archived copy of the haplotype visualization tool 148 to the structural variation and phasing system 100 and installs (if it has not been installed before) during the setup process. It will be appreciated that the system and method disclosed for remote initiation of the haplotype visualization tool 148 on a remote computer is applicable to a broad range of applications that require the computational resources of a remote server with the concomitant visual interface operating on a local computer in order to control such applications and to visualize data and computational results in real time or near real time.

Referring once again to FIGS. 1, 31, and 32, one aspect of the present disclosure provides a system 3100 for processing program output over a network connection 3106 (e.g., wired or wireless) using a local computer 3102. The local computer 3102 comprises one or more microprocessors (not shown), and a memory (not shown) that stores one or more programs (e.g., haplotype visualization tool 148). The one or more programs use the one or more microprocessors to execute a method in accordance with a first operating system running on the local computer. In the method, a first instance of a first program is invoked (e.g., a first instance of the haplotype visualization tool 148 is invoked on a client device 3102). Through the invoked first instance of the first program there is obtained, from a user, a login and a password to a user account on a remote computer (e.g., structural variation and phasing visualization system 100). The user is then logged into the user account on the remote computer automatically, using the login and the password provided by the first instance of the first program, across a network connection between the local computer and the remote computer (e.g., communication network 3106). Responsive to successful login on the remote computer 100, the method continues by automatically sending, without human intervention, a second instance of the first program 148 configured to auto-install on the remote computer 100 upon transmission to the remote computer. In some embodiments, the remote computer already has the second instance of the first program 148 installed and in some such embodiments the second instance of the first program is therefore not transmitted to the remote computer for installation. Once the second instance of the first program is installed on the remote computer 100, there is received from the remote computer a request to open a panel (not shown). This panel is originated by the second instance of the first program running on the remote computer 100. The panel solicits input from the user for controlling the second instance of the first program. For instance, in some embodiments this panel is of the form illustrated in any one of FIG. 12-21. In some embodiments, the panel is simpler, for instance containing a prompt for a dataset name or a search query for searching in a specified dataset. Responsive to receiving input from the user for controlling the second instance of the first program in the panel on the local computer, the input is sent to the second instance of the first program running on the remote computer 100 across the network connection. The remote computer receives across the network connection this input and, subsequently, output from the second instance of the first program responsive to the input is displayed as output on the local computer (e.g. within the first instance of the first program or in a separate web browser).

Figure 2:
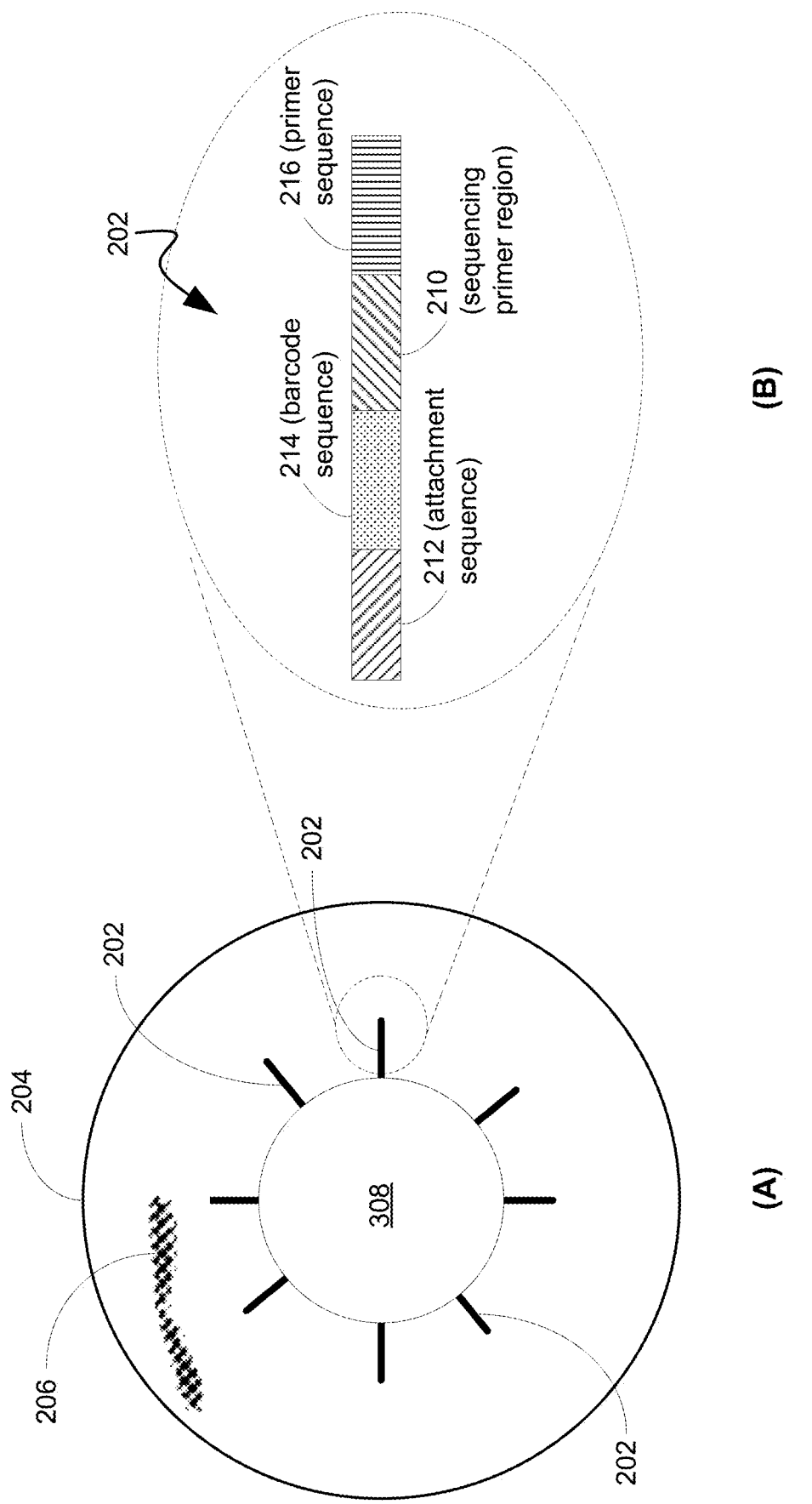
FIG. 2 illustrates exemplary constructs in accordance with an embodiment of the present disclosure.

Referring to FIG. 2, in accordance with the disclosed systems and methods, a plurality of sequencing reads (not shown in its entirety in FIG. 2) is obtained using a test (target) nucleic acid 206 of a biological sample from a subject. In typical embodiments, the test (target) nucleic acid 206 is a fragment of the genome of the biological sample. In some embodiments, there is a single test (target) nucleic acid 206 (fragment) in a partition. In some embodiments, there are two or more test nucleic acids 206 (fragments) in a partition each corresponding to different portions of the genome of the species of the biological sample. In some embodiments, there are five or more nucleic acids 206 (fragments) in a partition each corresponding to different portions of the genome of the species of the biological sample. In some embodiments, there are ten or more nucleic acids 206 in a partition each corresponding to different portions of the genome of the species of the biological sample. In some embodiments, the biological sample is a mixture and includes nucleic data representing the genome of two or more individuals in a species. In some embodiments, the biological sample is a mixture and includes nucleic data representing the genome of two or more species. For instance, in some embodiments the biological sample is infected with a retrovirus. In another example, the biological sample contains metagenomes because the sample was taken from sand or dirt or some other location and the goal is to find all the different genomes that exist in the sample.

The sequencing reads ultimately form the basis of a nucleic acid sequencing dataset 126. Each respective sequencing read 202 in the plurality of sequencing reads comprises a first portion that corresponds to a subset of a test nucleic acid and a second portion that encodes identification information for the respective sequencing read. The identification information is independent of the sequencing data of the test nucleic acid.

In some embodiments, sequencing read lengths have an N50 (where the sum of the sequence read lengths that are greater than the stated N50 number is 50% of the sum of all sequencing read lengths). In typical embodiments, sequencing reads are tens or hundreds of bases in length, which in turn, are aligned to form constructs of at least about 10 kb, at least about 20 kb, or at least about 50 kb. In more preferred aspects, sequencing reads are tens or hundreds of bases in length, which in turn, are aligned to form constructs having at least about 100 kb, at least about 150 kb, at least about 200 kb, and in many cases, at least about 250 kb, at least about 300 kb, at least about 350 kb, at least about 400 kb, and in some cases, at least about 500 kb or more.

In some embodiments, to obtain the plurality of sequencing reads from a biological sample from a subject, a test nucleic acid 206 is fragmented and these fragments are compartmentalized, or partitioned into discrete compartments or partitions (referred to interchangeably herein as partitions). In some embodiments, the test nucleic acid is the genome of a multi-chromosomal organism such as a human. In typical embodiments, multiple sequencing reads are measured from each such compartment or partition with lengths that are tens or hundreds of bases in length. Sequencing reads from the same compartment or partition that have the same bar code can be aligned to form sequence constructs that are at least about 25 kb, at least about 50 kb, 100 kb, at least about 150 kb, at least about 200 kb, and in many cases, at least about 250 kb, at least about 300 kb, at least about 350 kb, at least about 400 kb, and in some cases, at least about 500 kb or more in length.

Each partition maintains separation of its own contents from the contents of other partitions. As used herein, the partitions refer to containers or vessels that may include a variety of different forms, e.g., wells, tubes, micro or nanowells, through holes, or the like. In preferred aspects, however, the partitions are flowable within fluid streams. In some embodiments, these vessels are comprised of, e.g., microcapsules or micro-vesicles that have an outer barrier surrounding an inner fluid center or core, or have a porous matrix that is capable of entraining and/or retaining materials within its matrix. In a preferred aspect, however, these partitions comprise droplets of aqueous fluid within a non-aqueous continuous phase, e.g., an oil phase. A variety of different vessels are described in, for example, U.S. patent application Ser. No. 13/966,150, filed Aug. 13, 2013, which is hereby incorporated by reference herein in its entirety. Likewise, emulsion systems for creating stable droplets in non-aqueous or oil continuous phases are described in detail in, e.g., Published U.S. Patent Application No. 2010-0105112, which is hereby incorporated by reference herein in its entirety. In certain embodiments, microfluidic channel networks are particularly suited for generating partitions as described herein. Examples of such microfluidic devices include those described in detail in Provisional U.S. Patent Application No. 61/977,804, filed Apr. 4, 2014, as well as PCT/US15/025197, the full disclosures of which are incorporated herein by reference in their entirety for all purposes. Alternative mechanisms may also be employed in the partitioning of individual cells, including porous membranes through which aqueous mixtures of cells are extruded into non-aqueous fluids. Such systems are generally available from, e.g., NANOMI, Inc.

In the case of droplets in an emulsion, partitioning of the test nucleic acid fragments into discrete partitions may generally be accomplished by flowing an aqueous, sample containing stream, into a junction into which is also flowing a non-aqueous stream of partitioning fluid, e.g., a fluorinated oil, such that aqueous droplets are created within the flowing stream partitioning fluid, where such droplets include the sample materials. As described below, the partitions, e.g., droplets, also typically include co-partitioned barcode oligonucleotides.

The relative amount of sample materials within any particular partition may be adjusted by controlling a variety of different parameters of the system, including, for example, the concentration of test nucleic acid fragments in the aqueous stream, the flow rate of the aqueous stream and/or the non-aqueous stream, and the like. The partitions described herein are often characterized by having overall volumes that are less than 1000 pL, less than 900 pL, less than 800 pL, less than 700 pL, less than 600 pL, less than 500 pL, less than 400 pL, less than 300 pL, less than 200 pL, less than 100 pL, less than 50 pL, less than 20 pL, less than 10 pL, or even less than 1 pL. Where co-partitioned with beads, it will be appreciated that the sample fluid volume within the partitions may be less than 90% of the above described volumes, less than 80%, less than 70%, less than 60%, less than 50%, less than 40%, less than 30%, less than 20%, or even less than 10% the above described volumes. In some cases, the use of low reaction volume partitions is particularly advantageous in performing reactions with very small amounts of starting reagents, e.g., input test nucleic acid fragments. Methods and systems for analyzing samples with low input nucleic acids are presented in U.S. Provisional Patent Application No. 62/017,580 Jun. 26, 2014, the full disclosure of which is hereby incorporated by reference in its entirety.

Once the test nucleic acid fragments are introduced into their respective partitions, the test nucleic acid fragments within partitions are generally provided with unique identifiers such that, upon characterization of those test nucleic acid fragments, they may be attributed as having been derived from their respective partitions. Such unique identifiers may be previously, subsequently or concurrently delivered to the partitions that hold the compartmentalized or partitioned test nucleic acid fragments, in order to allow for the later attribution of the characteristics, e.g., nucleic acid sequence information, to the sample nucleic acids included within a particular compartment, and particularly to relatively long stretches of contiguous sample nucleic acids that may be originally deposited into the partitions.

Accordingly, the test nucleic acid fragments are typically co-partitioned with the unique identifiers (e.g., barcode sequences). In particularly preferred aspects, the unique identifiers are provided in the form of oligonucleotides that comprise nucleic acid barcode sequences that is attached to test nucleic acid fragments in the partitions. The oligonucleotides are partitioned such that as between oligonucleotides in a given partition, the nucleic acid barcode sequences contained therein are the same, but as between different partitions, the oligonucleotides can, and preferably have differing barcode sequences. In some embodiments, only one nucleic acid barcode sequence is associated with a given partition, although in some embodiments, two or more different barcode sequences are present in a given partition.

The nucleic acid barcode sequences will typically include from 6 to about 20 or more nucleotides within the sequence of the oligonucleotides. These nucleotides may be completely contiguous, i.e., in a single stretch of adjacent nucleotides, or they may be separated into two or more separate subsequences that are separated by one or more nucleotides. Typically, separated subsequences may typically be from about 4 to about 16 nucleotides in length.

The test nucleic acid is typically partitioned such that the nucleic acids are present in the partitions in relatively long fragments or stretches of contiguous nucleic acid molecules. These fragments typically represent a number of overlapping fragments of the overall test nucleic acid to be analyzed, e.g., an entire chromosome, exome, or other large genomic fragment. This test nucleic acid may include whole genomes, individual chromosomes, exomes, amplicons, or any of a variety of different nucleic acids of interest. Typically, the fragments of the test nucleic acid that are partitioned are longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb.

The test nucleic acid is also typically partitioned at a level whereby a given partition has a very low probability of including two overlapping fragments of the starting test nucleic acid. This is typically accomplished by providing the test nucleic acid at a low input amount and/or concentration during the partitioning process. As a result, in preferred cases, a given partition includes a number of long, but non-overlapping fragments of the starting test nucleic acid. The nucleic acid fragments in the different partitions are then associated with unique identifiers, where for any given partition, nucleic acids contained therein possess the same unique identifier, but where different partitions include different unique identifiers. Moreover, because the partitioning step allocates the sample components into very small volume partitions or droplets, it will be appreciated that in order to achieve the desired allocation as set forth above, one need not conduct substantial dilution of the sample, as would be required in higher volume processes, e.g., in tubes, or wells of a multiwell plate. Further, because the systems described herein employ such high levels of barcode diversity, one can allocate diverse barcodes among higher numbers of genomic equivalents, as provided above. In some embodiments, in excess of 10,000, 100,000, 500,000, etc. diverse barcode types are used to achieve genome:(barcode type) ratios that are on the order of 1:50 or less, 1:100 or less, 1:1000 or less, or even smaller ratios, while also allowing for loading higher numbers of genomes (e.g., on the order of greater than 100 genomes per assay, greater than 500 genomes per assay, 1000 genomes per assay, or even more) while still providing for far improved barcode diversity per genome. Here, each such genome is an example of a test nucleic acid.

Referring to FIG. 2, panels A and B, often the above-described partitioning is performed by combining the sample containing the test nucleic acid with a set of oligonucleotide tags (containing the barcodes) that are releasably-attached to beads 308 prior to the partitioning step. The oligonucleotides may comprise at least a primer region 216 and a barcode 214 region. Between oligonucleotides within a given partition, the barcode region 214 is substantially the same barcode sequence, but as between different partitions, the barcode region in most cases is a different barcode sequence. In some embodiments, the primer region 216 is an N-mer (either a random N-mer or an N-mer designed to target a particular sequence) that is used to prime the nucleic acids within the sample within the partitions. In some cases, where the N-mer is designed to target a particular sequence, the primer region 216 is designed to target a particular chromosome (e.g., human chromosome 1, 13, 18, or 21), or region of a chromosome, e.g., an exome or other targeted region. In some cases, the N-mer is designed to target a particular gene or genetic region, such as a gene or region associated with a disease or disorder (e.g., cancer). In some cases, the N-mer is designed to target a particular structural variation. Within the partitions, an amplification reaction is conducted using the primer sequence 216 (e.g. N-mer) to prime the nucleic acid sample at different places along the length of the nucleic acid. As a result of the amplification, each partition contains amplified products of the nucleic acid 202 that are attached to an identical or near-identical barcode, and that represent overlapping, smaller fragments of the nucleic acids in each partition. The barcode 214 therefore serves as a marker that signifies that a set of nucleic acids originated from the same partition, and thus potentially also originated from the same strand of test nucleic acid. Following amplification, the nucleic acids are pooled, sequenced, and aligned using a sequencing algorithm. Because shorter sequence reads may, by virtue of their associated barcode sequences, be aligned and attributed to a single, long fragment of the test nucleic acid, all of the identified variants on that sequence can be attributed to a single originating fragment and single originating chromosome of the test nucleic acid. Further, by aligning multiple co-located variants across multiple long fragments, one can further characterize that chromosomal contribution. Accordingly, conclusions regarding the phasing of particular genetic variants may then be drawn. Such information may be useful for identifying haplotypes, which are generally a specified set of genetic variants that reside on the same nucleic acid strand or on different nucleic acid strands. Moreover, additionally or alternatively, structural variants are identified.

In some embodiments, the co-partitioned oligonucleotides also comprise functional sequences in addition to the barcode region 214 and the primer region 216 region of the nucleic acids within the sample within the partitions. See, for example, the disclosure on co-partitioning of oligonucleotides and associated barcodes and other functional sequences, along with sample materials as described in, for example, U.S. Patent Application Nos. 61/940,318, filed Feb. 7, 2014, 61/991,018, Filed May 9, 2014, and U.S. patent application Ser. No. 14/316,383, filed on Jun. 26, 2014, as well as U.S. patent application Ser. No. 14/175,935, filed Feb. 7, 2014, the full disclosures of which is hereby incorporated by reference in their entireties.

In one exemplary process, beads are provided, where each such bead includes large numbers of the above described oligonucleotides releasably attached to the beads. In such embodiments, all of the oligonucleotides attached to a particular bead include the same nucleic acid barcode sequence, but a large number of diverse barcode sequences are represented across the population of beads used. Typically, the population of beads provides a diverse barcode sequence library that includes at least 1000 different barcode sequences, at least 10,000 different barcode sequences, at least 100,000 different barcode sequences, or in some cases, at least 1,000,000 different barcode sequences. Additionally, each bead typically is provided with large numbers of oligonucleotide molecules attached. In particular, the number of molecules of oligonucleotides including the barcode sequence on an individual bead may be at least about 10,000 oligonucleotides, at least 100,000 oligonucleotide molecules, at least 1,000,000 oligonucleotide molecules, at least 100,000,000 oligonucleotide molecules, and in some cases at least 1 billion oligonucleotide molecules.

In some embodiments, the oligonucleotides are releasable from the beads upon the application of a particular stimulus to the beads. In some cases, the stimulus may be a photo-stimulus, e.g., through cleavage of a photo-labile linkage that may release the oligonucleotides. In some cases, a thermal stimulus may be used, where elevation of the temperature of the beads environment may result in cleavage of a linkage or other release of the oligonucleotides form the beads. In some cases, a chemical stimulus may be used that cleaves a linkage of the oligonucleotides to the beads, or otherwise may result in release of the oligonucleotides from the beads.

In accordance with the methods and systems described herein, the beads including the attached oligonucleotides may be co-partitioned with the individual samples, such that a single bead and a single sample are contained within an individual partition. In some cases, where single bead partitions are desired, it may be desirable to control the relative flow rates of the fluids such that, on average, the partitions contain less than one bead per partition, in order to ensure that those partitions that are occupied, are primarily singly occupied. Likewise, one may wish to control the flow rate to provide that a higher percentage of partitions are occupied, e.g., allowing for only a small percentage of unoccupied partitions. In preferred aspects, the flows and channel architectures are controlled as to ensure a desired number of singly occupied partitions, less than a certain level of unoccupied partitions and less than a certain level of multiply occupied partitions.

Figure 4:
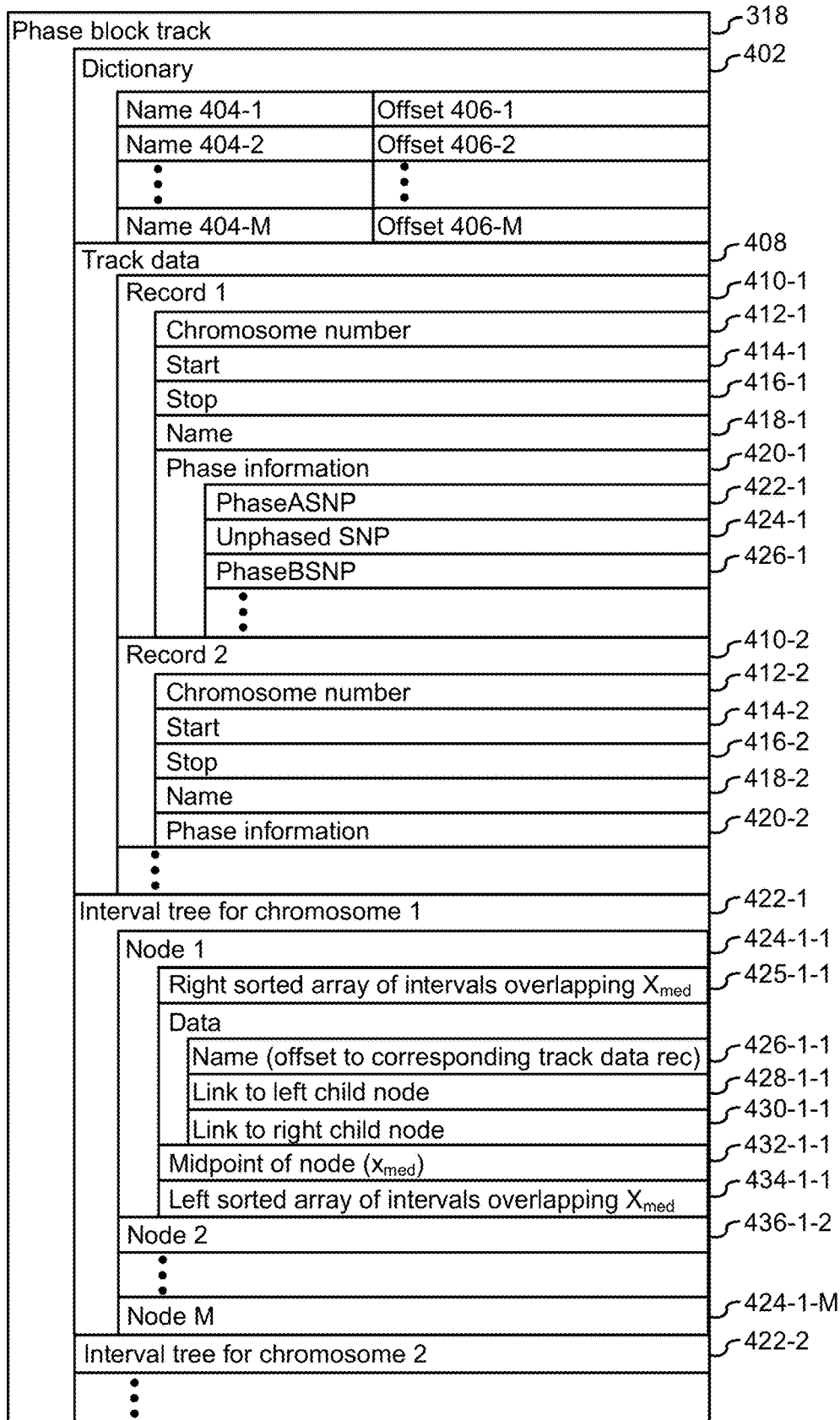
FIG. 4 illustrates the data structure of an example phase block track within a nucleic acid sequencing dataset in accordance with some embodiments.

FIG. 3 of U.S. Patent Application No. 62/072,214, filed Oct. 29, 2014, entitled "Analysis of Nucleic Acid Sequences," which is hereby incorporated by reference and the portions of the specification therein describing FIG. 3 provide a detailed example of one method for barcoding and subsequently sequencing a test nucleic acid (referred to in the reference as a "sample nucleic acid") in accordance with one embodiment of the present disclosure. As noted above, while single bead occupancy may be the most desired state, it will be appreciated that multiply occupied partitions, or unoccupied partitions may often be present. FIG. 4 of U.S. Patent Application No. 62/072,214, filed Oct. 29, 2014, entitled "Analysis of Nucleic Acid Sequences," which is hereby incorporated by reference and the portions of the specification describing FIG. 4 therein provide a detailed example of a microfluidic channel structure for co-partitioning samples and beads comprising barcode oligonucleotides in accordance with one embodiment of the present disclosure.

Once co-partitioned, the oligonucleotides disposed upon the beads may be used to barcode and amplify the partitioned samples. One process for use of these barcode oligonucleotides in amplifying and barcoding samples is described in detail in U.S. Patent Application Nos. 61/940,318, filed Feb. 7, 2014, 61/991,018, Filed May 9, 2014, and U.S. patent application Ser. No. 14/316,383, filed on Jun. 26, 2014, the full disclosures of which are hereby incorporated by reference in their entireties. Briefly, in one aspect, the oligonucleotides present on the beads that are co-partitioned with the samples are released from their beads into the partition with the samples. The oligonucleotides typically include, along with the barcode sequence, a primer sequence at its 5' end. This primer sequence may be a random oligonucleotide sequence intended to randomly prime numerous different regions of the samples, or it may be a specific primer sequence targeted to prime upstream of a specific targeted region of the sample.

Once released, the primer portion of the oligonucleotide can anneal to a complementary region of the sample. Extension reaction reagents, e.g., DNA polymerase, nucleoside triphosphates, co-factors (e.g., $Mg^{2+}$ or $Mn^{2+}$ etc.), that are also co-partitioned with the samples and beads, then extend the primer sequence using the sample as a template, to produce a complementary fragment to the strand of the template to which the primer annealed, with complementary fragment that includes the oligonucleotide and its associated barcode sequence. Annealing and extension of multiple primers to different portions of the sample may result in a large pool of overlapping complementary fragments of the sample, each possessing its own barcode sequence indicative of the partition in which it was created. In some cases, these complementary fragments may themselves be used as a template primed by the oligonucleotides present in the partition to produce a complement of the complement that again, includes the barcode sequence. In some cases, this replication process is configured such that when the first complement is duplicated, it produces two complementary sequences at or near its termini, to allow the formation of a hairpin structure or partial hairpin structure that reduces the ability of the molecule to be the basis for producing further iterative copies. A schematic illustration of one example of this is shown in FIG. 2.

As FIG. 2 shows, oligonucleotides 202 that include a barcode sequence 214 are co-partitioned in, e.g., a droplet 204 in an emulsion, along with a sample test nucleic acid fragment 206. In some embodiments, the oligonucleotides 202 are provided on a bead 208 that is co-partitioned with the test nucleic acid fragment 206, which oligonucleotides are preferably releasable from the bead 208, as shown in FIG. 2, panel (A). As shown in FIG. 2 panel (B), the oligonucleotides 202 includes a barcode sequence 214, in addition to one or more functional sequences, e.g., sequences 212, 214 and 216. For example, oligonucleotide 202 is shown as further comprising sequence 212 that may function as an attachment or immobilization sequence for a given sequencing system, e.g., a P5 sequence used for attachment in flow cells of an ILLUMINA, HISEQ or MISEQ system. In other words, attachment sequence 212 is used to reversibly attach oligonucleotide 202 to a bead 208 in some embodiments. As shown in FIG. 2, panel B, the oligonucleotide 202 also includes a primer sequence 216, which may include a random or targeted N-mer (discussed above) for priming replication of portions of the sample test nucleic acid fragment 206. Also included within exemplary oligonucleotide 202 of FIG. 2, panel B, is a sequence 210 which may provide a sequencing priming region, such as a "read1" or R1 priming region, that is used to prime polymerase mediated, template directed sequencing by synthesis reactions in sequencing systems. In many cases, the barcode sequence 214, immobilization (attachment) sequence 212 and exemplary R1 sequence 214 may be common to all of the oligonucleotides 202 attached to a given bead. The primer sequence 216 may vary for random N-mer primers, or may be common to the oligonucleotides on a given bead for certain targeted applications. FIGS. 3B through 3E and the specification describing these Figures in U.S. Prov. Application No. 62/113,693, entitled "Systems and Methods for Determining Structural Variation," filed Feb. 9, 2014 detail how oligonucleotides 202 form sequencing reads of the sample test nucleic acid, where each such sequencing read includes a first portion that is a sequencing read of the sample test nucleic acid and a second portion that is the oligonucleotide 202. Such sequencing reads, and analysis of such sequencing reads, form the basis of the disclosed nucleic acid sequencing dataset 126.

In some embodiments, the sequencing reads in a nucleic acid sequencing dataset 126 are processed in order to sequence the at least one target nucleic acid. In some embodiments conventional methods are used to process the nucleic acid sequence reads in order to establish a sequence for the at least one target nucleic acid. In some embodiments the novel methods disclosed in PCT application PCT/US2015/038175, entitled "Processes and Systems for Nucleic Acid Sequence Assembly," filed Jun. 26, 2015, which is hereby incorporated by reference, are used to process the nucleic acid sequence reads in order to establish a sequence for the at least one target nucleic acid. In some embodiments, such sequencing involves mapping the sequencing reads to a reference genome, such as the genome of the species from which the sample is taken. In some embodiments, the sample is expected, or suspected, of containing multiple genomes (e.g., the case in which a sample, such as a human sample, infected with a retrovirus). In such cases, multiple reference genomes, from different species may be concurrently used.

In some embodiments, the sequencing reads are processed by phasing them and by looking for structural variations. In some embodiments, conventional phasing methods and structural variation methods are used. In some embodiments, novel phasing methods and structural variation methods, such as those disclosed in U.S. Provisional Application No. 62/238,077, entitled "Systems and Method for Determining Structural Variation Using Probabilistic Models," filed Oct. 6, 2015, which is hereby incorporated by reference, are used. Although not disclosed in this reference, in some embodiments the teachings of the reference are extended to incorporate multiple reference genomes in instances where the sample potential contains nucleic acid from multiple reference genomes. For instance, in the case where the sample is human but it is possible that the sample is infected with a retrovirus, the genome of the retrovirus is treated as an additional chromosome. In this way, it is possible to extend the visualization methods disclosed in the present disclosure to identify insertion of nucleic acid constructs, such as retroviruses, into the genome of the sample under study.

So, for example, the disclosed techniques can use the bar codes to distinguish the following two scenarios. One is a human sample with HPV virus free floating in the sample but the virus hasn't been inserted into the human DNA. They are a free floating molecule—separate molecules, separate virus, separate human DNA. In that case, the measured sequence reads are going to include reads that map to HPV as well as the human genome but there will not be bar codes in common with the HPV and the human genome meaning that the human genome and the HPV are distinct. On the other hand, if the HPV molecule has been inserted into a human chromosome or two, what will be measured are sequence reads that map to both a human chromosome and the HPV at the same time and share the same bar codes meaning that they exist in the same molecule as opposed to separate molecules (e.g., the HPV has been incorporated into a human chromosome). Moreover, the bar codes can be used to localize the precise location(s) of the HPV insertion into the human chromosome.

FIG. 3 illustrates the data that is obtained from a biological sample of a subject (e.g., a particular human). This data is summarized in the form of a nucleic acid sequence dataset 126. In some instances, a full-genome run of the type described above produces 30-40 gigabytes worth of data. In accordance with some aspects of the present disclosure, such raw data is condensed into a nucleic acid sequence dataset 126 that is a fraction of the size of the raw data. In some embodiments, although the raw data is condensed to form the nucleic acid sequence dataset 126, the dataset 126 is still too large to load into the RAM of typical computers. For instance, in some embodiments, nucleic acid sequence dataset 126 is five gigabytes or larger, ten gigabytes or larger, or fifteen gigabytes or larger.

As illustrated in FIG. 3, the exemplary nucleic acid sequencing dataset 126 is organized into three parts, a header 302, a synopsis 308, and a data section 340. The purpose of the header 302 is to delineate the components 304 of the dataset 126 as well as, optionally, provide the version 306 of the dataset 126 structure, e.g., version 1.7. In some embodiments, the header 302 is formatted as a JSON structure to facilitate loading using web based applications such as a web browser. For instance, in some embodiments, the header is formatted as a JSON object: beginning with { (left brace) and ending with} (right brace), with each name is followed by : (colon) and the name/value pairs are separated by, (comma). In one exemplary embodiment, the header 302 that specifies that the sequencing dataset has 126 has the components: fragment tracks (e.g., the length, position, barcode, and phase of all the fragments in the dataset), targets track (the regions of the genome selected by the capture protocol used during processing), structural variation track (lists of all the structural variants called in the sample), an index to a target dataset, vcf_index (an index that relates ranges of the genome to a position in the dataset 126 file), marker, phase block summary (a description of the various phase blocks in the test nucleic acid 206), genetrack (a description of all human genes, tagged with the number of SNPs in each gene), BAM data (associates ranges of the genome to the position in the file containing read information for that range), summary (high level metrics extracted from the sequencing data), and refseq index (an index that contains a list of dbSNP identifiers (RSIDs) of SNPs that are called in the sample, thereby associating the RSID with its position in the genome).

The synopsis section 308 contains data that is read by haplotype visualization tool 148 into volatile (e.g., random access) memory, typically in its entirety, when the dataset 126 is accessed. This data consists of indexes into the data section 340 as well as other data that is referenced frequently by visualization tool 148. As illustrated in FIG. 3, the synopsis section 308 is split up into several components which correspond to the "index" array (e.g., component list 302) in the header section 302.

Summary 310 provides high level metrics extracted from the data. In some embodiments, summary 310 is used by summarization module 150 to provide summary data such as that illustrated in FIGS. 12 and 13. This includes the percentage of known SNPs (e.g., human SNPs) phased 1202, the longest phase block 1204, the effective barcode count 1206 (e.g., the number of unique barcodes used in the dataset 126), average fragment length 1208, mean of average fragment length 1210, percentage of fragments greater than a lower threshold (e.g., 20 kb) 1212, fragment length histogram or other form of fragment length metric 1214, N50 phase block size 1216, phase block length histogram or other form of phase block length metric 1218, number of sequence reads represented by the dataset 1220, median insert size 1222, median depth 1224, percent of the target genome with zero coverage 1226, mapped reads percentage 1228, PCR duplication percentage 1230, on target bases (percent) 1232, coverage histogram or other form of coverage metric 1234, source of dataset in memory 112 (1234), identity of test nucleic acid (1236), genome source (1238), sex of donating organism (1240), dataset file format version 1242, and pointer to structural variant calls 1244 made for dataset 126 (1244).

Index to variant call data 312 is an example of an index found in the summary and it relates respective ranges 214 of the genome of the target nucleic acid to offsets 316 in the corresponding data section 340 where variant call data for the respective ranges is found.

In some embodiments, the phase block track 318 is stored in the synopsis section 308 of the nucleic acid sequencing dataset 126. More details of the architecture of an exemplary phase block track 318 are found in FIG. 4. Referring to FIG. 4, in some embodiments, the phase block track 318 includes a dictionary section 402 and a track data section 408. the track data section comprises a plurality of records 410. In some embodiments, each record in the plurality of records comprises phase information for a corresponding chromosome. In some embodiments, each of the one or more data sections stores phase information for one or more corresponding chromosomes. In some embodiments, each of the one or more data sections stores phase information in an interval tree 422 format for a corresponding chromosome.

The dictionary 402 of the phase block track 318 comprises a plurality of names 404, and for each name 404, an offset 406 into the track data 408 where records for the corresponding name 404 are found. In some embodiments, the dictionary 402 for the phase block track 318 contains a single name, e.g., "phase data".

In some embodiments, the track data 408 is in JSON format. In some embodiments, each record 410 represents a phase block in the target nucleic acid. As such, in some embodiments, each record 410 specifies a chromosome number 412 that the phase block is on as well as the position where the phase block starts 414 on the chromosome 412 and a position where the phase block ends 416 on the chromosome 412. Moreover, there is a unique name 418 for each record and phasing information 420 about the phase block. In some embodiments, the purpose for the information 420 is to provide details of phasing information of the phase block. In some embodiments, a phase block includes information about two haplotypes corresponding to the two parents (e.g., respectively denoted haplotype "A" and haplotype "B"). Accordingly, in some embodiments, the phase information comprises PhaseASNP 422 (the number of counted single nucleotide polymorphisms on haplotype "A" in the phase block), Unphased SNP 424 (the number of counted single nucleotide polymorphisms of unknown haplotype in the phase block) and PhaseBSNP (the number of counted single nucleotide polymorphisms on haplotype "B" in the phase block). As such, the track data 408 holds certain phase block data (e.g., SNP counts) for the nucleic acid sequencing dataset 126. Techniques for phasing genomic data and phase blocks are described in Browning and Browning, "Haplotype phasing: Existing methods and new developments," Nat Rev Genet.; 12(10): 703-714. doi: 10.1038/nrg3054, which is hereby incorporated by reference in its entirety.

In some embodiments, the track data 408 is put into context by corresponding interval trees 422. As such, each record 410 is represented by a node 424 in an interval tree 422. Each such interval tree 422 is a ternary tree with each node 424 of the tree storing a midpoint of the node $x_{med}$ 432. This midpoint 432 is the position of the midpoint, on the corresponding chromosome, of the phase block corresponding to the node. Each respective node 424 has a link to a left child node 428, which corresponds to the phase block immediately to the left of the phase block represented by the respective node 424 in the genome of the species of the target (genetic source) organism. Each respective node 424 has a link to a right child node 430, which corresponds to the phase block immediately to the right of the phase block represented by the respective node 424. Each respective node 424 has a sorted set of nodes 425 that represent phase blocks that overlap the $x_{med}$ 432 of the respective node 424 sorted by left hand position of such phase block. Each respective node 424 has a sorted set of nodes 436 that represent phase blocks that overlap the $x_{med}$ 432 of the respective node 424 sorted by right hand position of such phase blocks. In some embodiments, sorted sets 425 and 436 are represented in a node 424 by arrays or linked lists. Each respective node 424 further includes a name 426, which is an offset in track data 410 to the record 410 that contains phase information 420 for the phase block corresponding to the respective node 424.

As illustrated in FIG. 4, in some embodiments, there is a separate interval tree 422 for each chromosome in the phase block track. Such interval trees advantageously provide a quick way of identifying all records 410 pertaining to a user specified region of the of the target genome. An example of a phase block track 318 is found in FIG. 5. In FIG. 5, exemplary elements that correspond to the data structure of FIG. 4 are illustrated.

Referring to FIG. 3, in some embodiments, the synopsis 308 further comprises a refseq index 319, which is an index that contains the molecular variation (e.g., SNP) identifiers that are called in the sample corresponding to the nucleic acid sequencing dataset. The refseq index 319 associates each such identifier with its position in the genome of the target organism. In some embodiments, the refseq index 319 is stored as a JSON data structure. In some embodiments, each polymorphism identifier in the refseq index 319 is a dbSNP identifier found in the National Center for Biotechnology Information (NCBI) database. See Wheeler et al., 2007, "Database resources of the National Center for Biotechnology Information," Nucleic Acids Res. 35 (Database issue): D5-12, which is hereby incorporated by reference. Such dbSNP identifiers are termed reference SNP cluster IDs (RSIDs).

Figure 6:
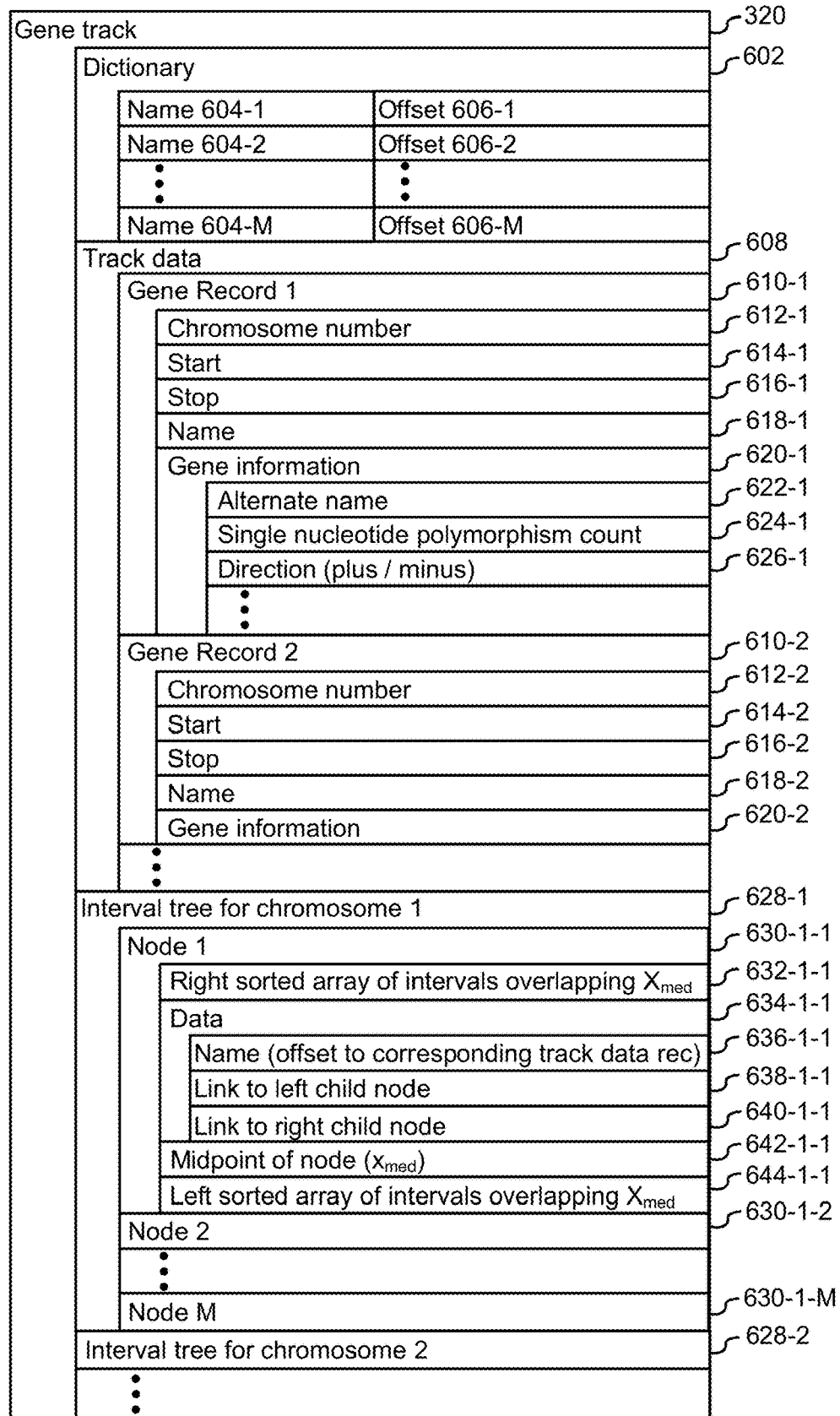
FIG. 6 illustrates the data structure of an example gene track in accordance with some embodiments.

In some embodiments, the synopsis 308 further comprises a gene track 320, which provides a reference of human genes tagged with the number of SNPs found in each gene. More details of the architecture of an exemplary gene track 320 are found in FIG. 6. Referring to FIG. 6, in some embodiments, the gene track 320 includes a dictionary section 602, a track data section 608, and one or more data sections 628. In some embodiments, each of the one or more data sections stores gene information for a corresponding chromosome. In some embodiments, each of the one or more data sections stores gene information for one or more corresponding chromosomes. In some embodiments, each of the one or more data sections stores gene information in an interval tree 628 format for a corresponding chromosome.

The dictionary 602 of the gene track 320 comprises a plurality of names 604, and for each name 604, an offset 606 into the track data 608 where records for the corresponding name 604 are found. In some embodiments, each name 604 in dictionary 602 is the name of a chromosome in the target genome.

In some embodiments, the track data 608 for gene track 320 comprises a plurality of gene records 610. In some embodiments, the track data 608 is in JSON format. In some embodiments, each gene record 610 represents a gene in the species of the target nucleic acid. As such, in some embodiments, each gene record 610 specifies a chromosome number 612 the corresponding gene is on, the position where the gene starts 614 on the chromosome 612 and a position where the gene ends 616 on the chromosome 612. Moreover, there is a unique name 618 for each gene record and gene information 620 about the gene. In some embodiments, the purpose for the information 620 is to provide genetic information about the gene, such as, for example, an alternative name 622 for the gene, a count of single nucleotide polymorphisms 624 on the gene, and a direction (e.g., plus or minus) 626 of the gene.

In some embodiments, the track data 608 is put into context by the corresponding interval trees 628. Each gene record 610 forms a node 630 in an interval tree 628. Each interval tree 628 is a ternary tree with each node 630 storing a midpoint of the node $x_{med}$ 642. This midpoint 642 is the position of the midpoint, on the corresponding chromosome, of the gene corresponding to the node. Each respective node 630 has a link to a left child node 638, which corresponds to the gene immediately to the left (lesser position on the chromosome) of the gene represented by the respective node 630 in the species of the target organism. Each respective node 630 has a link to a right child node 640, which corresponds to the gene immediately to the right of the gene (greater position on the chromosome) represented by the respective node 630 in the species of the target organism. Each respective node 620 has a sorted set of nodes 632 that respectively represent genes that overlap $x_{med}$ 632 of the respective node 620 sorted by left hand position. Each respective node 630 has a sorted set of nodes 630 that respectively represent genes that overlap the $x_{med}$ 642 of the respective node 630 sorted by right hand position. In some embodiments, sorted sets 632 and 644 are represented in a node 630 by arrays or linked lists. Each respective node 630 further includes a name 636, which is an offset in track data 608 to the gene record 610 that contains genetic information 620 for the gene corresponding to the respective node 630.

As illustrated in FIG. 6, in some embodiments, there is a separate interval tree 628 for each chromosome in the gene track 320. Such interval trees advantageously provide a quick way of identifying all records 610 pertaining to a user specified region of the of the target genome. An example of a gene track 320 is found in FIG. 7. In FIG. 7, exemplary elements that correspond to the data structure of FIG. 6 are illustrated.

In some embodiments, the synopsis 308 further comprises an exon track 322. In some embodiments, the exon track 322 has the same architecture as the gene track 320, the exception being that whereas the gene track 320 represents genetic information for genes in the species of the target organism, the exon track 320 provides genetic information for exons in the species of the target organism.

In some embodiments, the synopsis 308 further comprises an index to read data 324. This index 324 provides an index into sequence/read data 1048 in the data section 340 of the nucleic acid sequencing set, which is described in more detail below with reference to FIG. 10. Referring to FIG. 3, the index 324 comprises a database which associates identifiers to the barcodes used in the dataset (not shown). The database (lookup table) which associates identifiers to the barcodes used in the dataset is a useful way to compress the size of read data 1048, because identifiers can be used instead of the longer actual barcodes. This is because not all theoretically possible bar codes, for a given degree of information content, are used in a given dataset 126.

Figure 10:
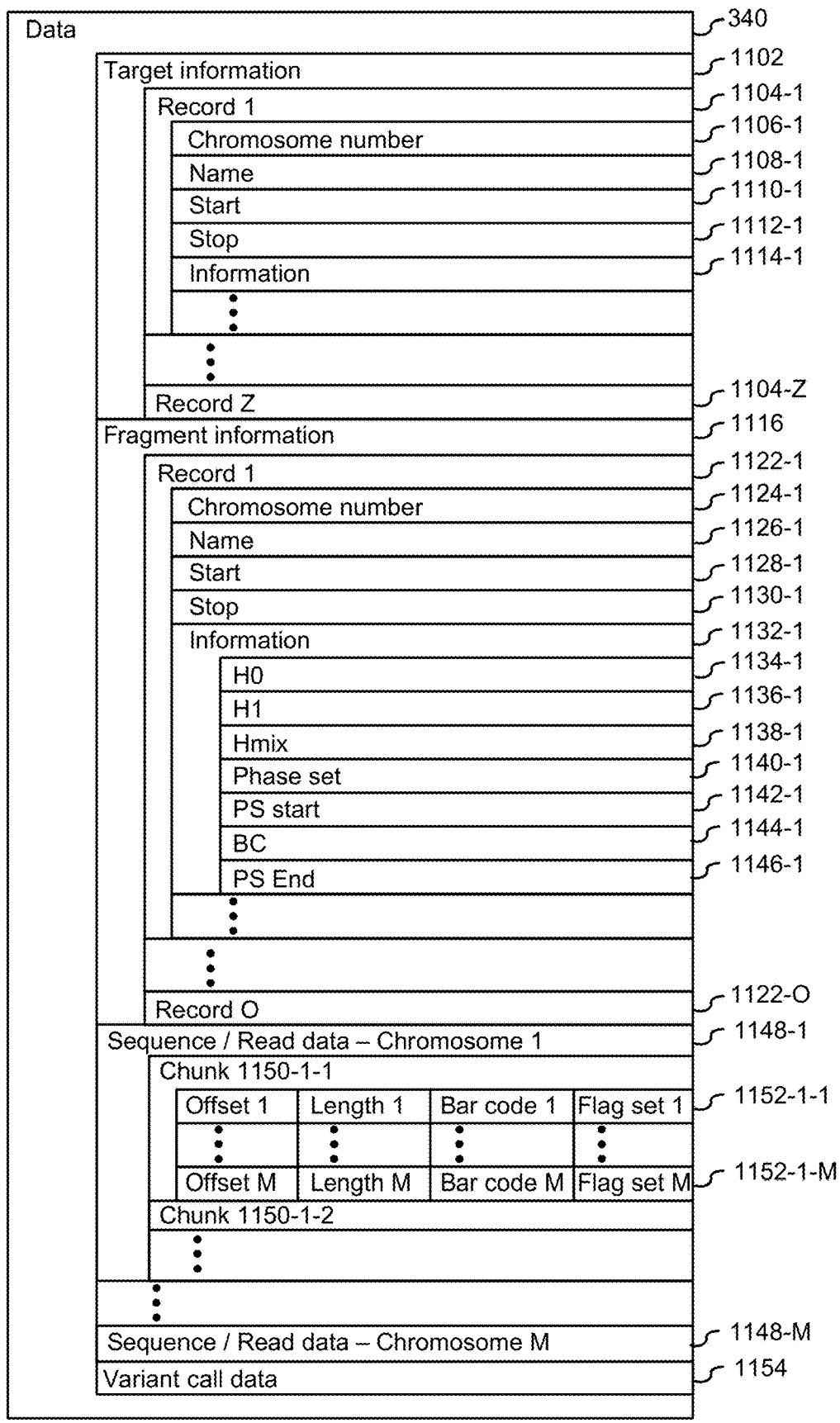
FIG. 10 illustrates target, fragment and sequence read data within a nucleic acid sequencing dataset in accordance with some embodiments.

The index 324 further comprises a per chromosome array of chromosome-offset→file-offset associations 328 into read data 1048 as well as a length of each such data element which allow lookup of the corresponding data for a specific genomic range. In some embodiments the read data is stored as a blocked index, and each record 328 is a fixed bit record for each entry in a BAM file that was incorporated into the dataset 126. Each such entry in the BAM file is organized into chunks within the data section 340 of the file. The index 324 in the synopsis 308 helps to find the correct chunk within the data section 340 to read. Referring to FIG. 10, the corresponding architecture of the sequence/read data 1048 indexed by index 324 is disclosed. For each chromosome, read data 1048 is stored in chunks 1050. In some embodiments, each data chunk 1050 is an array of 64-bit structures 1052 in the following format:

```
           6         5         4         3         2         1         0
[3210987654321098765432109876543210987654321098765432109876543210]
[0XLRIIIIIIIIIIIIIIIIIIIIIIIIIEEEEEEEEEEEEEEEESSSSSSSSSSSSSSSSSSSS]
``` where O is always O, X indicates the read quality is below a threshold value (e.g., below 60), L indicates the read is from parental haplotype A, R indicates the read is from parental haplotype B, I is a numerical identifier corresponding to the barcode in the read, E is the 'end' length of the read, and S is the 'start' position of this read, relative to the start of the chunk 1050. More generally, referring to FIG. 10, each structure 1052 corresponds to a single read from the target nucleic acid for the single organism of a species and comprises a start (offset), a length, an indicator to a bar code and some flags. In some embodiments the start within structure 1052 is the real position on the chromosome minus the start value stored for the chunk 1050 in the chromosome offset field of record 328 of index 324. Advantageously, this allows for avoidance of larger repetition of genomic coordinates in the structures 1052. Such coordinates can be in the billions and thus would required 30 bits to store. Advantageously, by chunking, as disclosed in sequence/read data 1048, each chunk covers up to about one million base pairs and thus each start (offset) in each structure 1052 in a chunk only needs 20 bits, since the range for any given chunk is specified by the chromosome offset/length portions of the corresponding record 328 in the index 324 stored in the synopsis 308. Similarly, as outlined above, in preferred embodiments, the barcode field in structure 1052 doesn't store the actual barcode. In some embodiments, the barcode indicator in structure 1052 is a 24-bit index into a barcode table that is stored in the index 324. So, when the actual barcode associated with a particular read is needed, the structure 1052 corresponding to the read is accessed, and the 24-bit bar code indicator in the structure 1052 is queried against the barcode table in the index 324 to obtain the bar code. In this way, 30 bit bar codes in the structures 1052 are avoided. In some embodiments, the bar code is greater than 30 bits (e.g., 32 bits, 34 bits, 36 bits or larger) and the indicator to the bar code in structure 1052 is greater than 20 bits (e.g., 22 bits, 24 bits, 26 bits or larger). In some embodiments, the bar code is less than 30 bits (e.g., 28 bits, 26 bits, 24 bits or smaller) and the indicator to the bar code in structure 1052 is less than 20 bits (e.g., 18 bits, 16 bit, 14 bits or smaller). In some embodiments, each data chunk 1050 is an array of structures 1052 having the same predetermined size (e.g., 128 bits, 64 bits, 32 bits, or some other fixed bit size).

Figure 8:
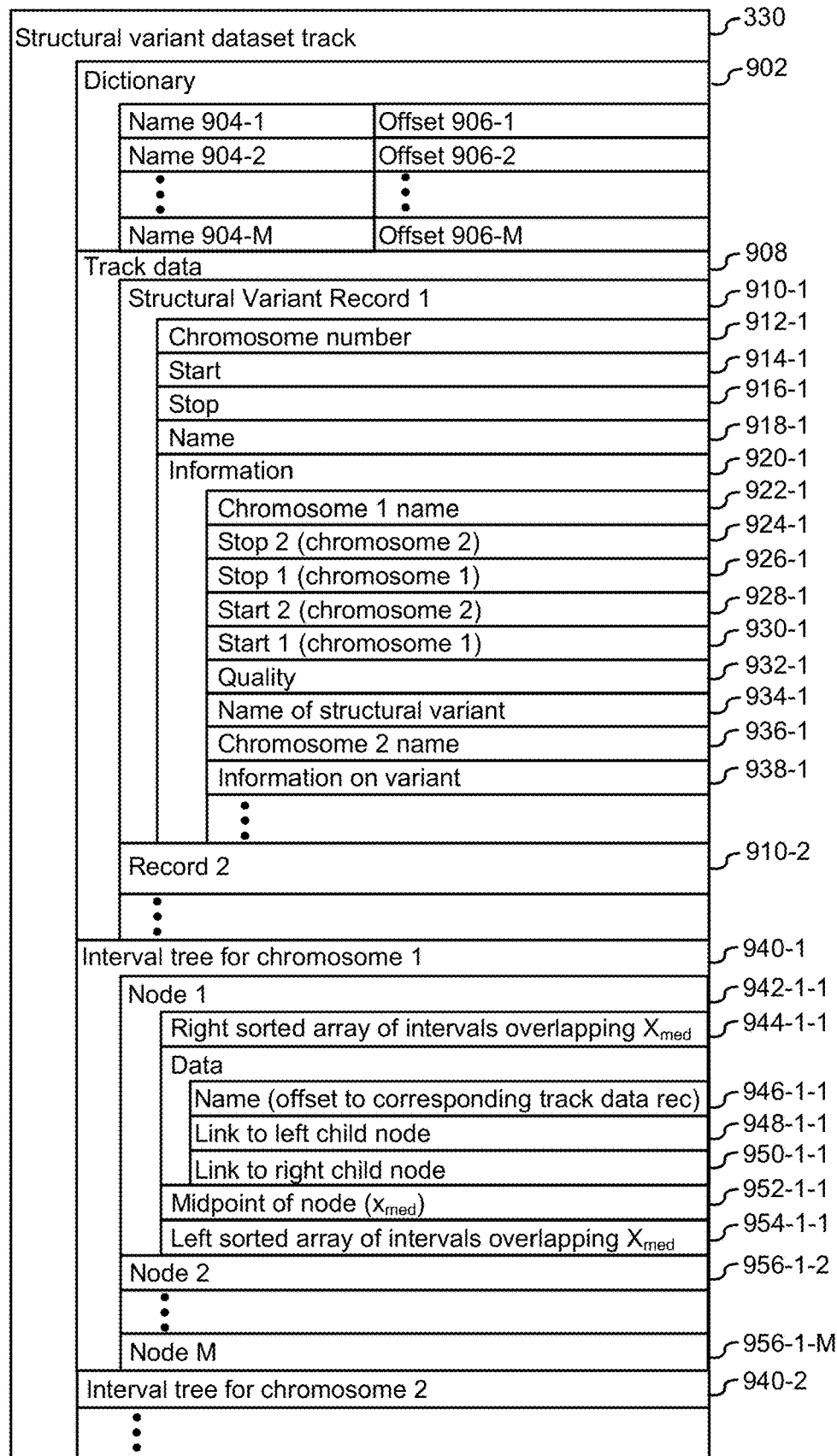
FIG. 8 illustrates the data structure of an example structural variant dataset track within a nucleic acid sequencing dataset in accordance with some embodiments.

In some embodiments, the synopsis 308 further comprises a structural variant dataset track 330. In some embodiments, the structural variants dataset track 330 comprises a listing of the called structural variants in the sample represented by the dataset 126. More details of the architecture of an exemplary structural variant dataset track 330 are found in FIG. 8. Referring to FIG. 8, in some embodiments, the structural variant dataset 330 includes a dictionary section 802, a track data section 808, and one or more data sections 840. In some embodiments, each of the one or more data sections 840 stores structural variant call information for a corresponding chromosome. In some embodiments, each of the one or more data sections 840 stores structural variant call information for one or more corresponding chromosomes. In some embodiments, each of the one or more data sections 840 stores gene information in an interval tree format for a corresponding chromosome.

The dictionary 802 of the structural variant dataset track 330 comprises a plurality of names 804, and for each name 804, an offset 606 into the track data 808 where records for the corresponding name 804 are found. In some embodiments, each name 804 in dictionary 802 is the name of a chromosome in the target genome.

In some embodiments, the track data 808 for structural variant dataset track 330 comprises a plurality of structural variant records 810. In some embodiments, the track data 808 is in JSON format. In some embodiments, each structural variant record 810 represents a structural variant call made for the target nucleic acid of the single organism represented by the dataset 126. As such, in some embodiments, each structural variant record 810 specifies a chromosome number 812, a start position 814 represented by the structural variation, a stop position 816 represented by the structural variation on the chromosome 812, a unique name 818 for the structural variation, and information 820 about the structural variation. In some embodiments, the structural variant dataset track 330 includes information analogous, corresponding to, or in a BEDPE format to advantageously concisely describe disjoint genome features, such as structural variations or paired-end sequence alignments. Accordingly, in some embodiments, the information section 820 in each structural variant record 810 includes a chromosome 1 name 822, which is the name of the chromosome on which the first end of the feature exists. In some embodiments chromosome 1 name 822 is in string format, for example, "chr1", "III", "myChrom", or "contig1112.23."

In some embodiments, the information section 820 in each record 810 further comprises a start 1 position 830, which is a zero-based starting position of the first end of the feature on chromosome 1 name 822.

In some embodiments, the information section 820 in each record 810 further comprises stop 1 (end 1) position 826, which is the one-based ending position of the first end of the feature (e.g., structural variation) represented by record 810 on chromosome 1 name 822.

In some embodiments, the information section 820 in each record 810 further comprises chromosome 2 name 836, which is the name of the chromosome on which the second end of the feature represented by record 810 exists. In some embodiments chromosome 2 name 836 is in string format, for example, "chr1", "III", "myChrom", or "contig1112.23."

In some embodiments, the information section 820 in each record 810 further comprises a start 2 position 828, which is the zero-based starting position of the second end of the feature represented by record 810 on chromosome 2 name 836.

In some embodiments, the information section 820 in each record 810 further comprises a stop 2 (end 2) position 824, which is the one-based ending position of the second end of the feature (e.g., structural variation) represented by record 810 on chromosome 2 name 836.

In some embodiments, the information section 820 in each record 810 further comprises a name of the structural variant field 834, which is the name of the feature (e.g., structural variation) represented by record 810. In some embodiments, the name of the structural variant 834 is in string format, for example, "LINE", "Exon3", "HWIEAS_0001:3:1:0:266#0/1", or "my_Feature".

In some embodiments, the information section 820 in each record 810 further comprises a quality (score) field 832, which is any metric the scores the quality of the feature (e.g., structural variation) represented by record 810. In some embodiments, quality 832 is in string format thereby permitting the expression of quality of the feature in any scientific metric, e.g., p-values, mean enrichment values, etc.

In some embodiments, the information section 820 in each record 810 further comprises further information 838 on the feature represented by the record 81, such as edit distance for each end of an alignment, or "deletion", "inversion", etc.).

Continuing to refer to FIG. 8, in some embodiments, the track data 808 is put into context by the corresponding interval trees 840. Each record 810 forms a node 842 in an interval tree 840. Each interval tree 840 is a ternary tree with each node 842 storing a midpoint of the node $x_{med}$ 852. This midpoint 852 is the position of the midpoint, on the corresponding chromosome, of the feature (e.g., structural variant) corresponding to the node and represented by the corresponding record 810. Each respective node 842 has a link to a left child node 848, which corresponds to the feature (e.g., structural variant) immediately to the left (lesser position on the chromosome) of the feature represented by the respective node 842 in the dataset 126. Each respective node 842 has a link to a right child node 850, which corresponds to the feature (e.g., structural variant) immediately to the right (greater position on the chromosome) of the feature represented by the respective node 842 in the dataset 126. Each respective node 842 has a sorted set of nodes 854 that respectively represent features (e.g., structural variant) that overlap $x_{med}$ 852 of the respective node 842 sorted by left hand position. Each respective node 842 has a sorted set of nodes 844 that respectively represent features that overlap the $x_{med}$ 852 of the respective node 842 sorted by right hand position. In some embodiments, sorted sets 844 and 854 are represented in a node 840 by arrays or linked lists. Each respective node 840 further includes a name 846, which is an offset in track data 808 to the record 810 that contains information 820 for the feature (e.g., structural variation) corresponding to the respective node 840.

As illustrated in FIG. 8, in some embodiments, there is a separate interval tree 840 for each chromosome in the structural variant dataset track 330. Such interval trees advantageously provide a quick way of identifying all records 810 pertaining to a user specified region of the of the target genome. An example of a portion of a structural variant dataset track 330 is found in FIG. 9. In FIG. 9, exemplary elements that correspond to the data structure of FIG. 8 are illustrated.

Referring to FIG. 3, in some embodiments, the synopsis 308 further comprises an index 332 to the target dataset 342. The target dataset 342 comprises the regions of the at least one target nucleic acid in the sample that were selected for sequencing in the nucleic acid sequencing dataset. In some embodiments index 332 and target dataset 342 are stored in a blocked JSON index. The blocked JSON index includes a single JSON object in the synopsis section (the index 332) and multiple JSON objects in the data section (the target dataset 342). The index 332 is used to calculate which data components must be read to fulfill a particular query. In some embodiments, the index 332 is split up by chromosome. For each chromosome, the index 332 stores an array (record) 334 associating ranges on that chromosome with the offset at which specific data for that range may be found in the target dataset. In some embodiments, the target dataset 342 contains many independent arrays. Each array contains all of the ranges (and associated data) for one contiguous range of the genome. Each array in the target dataset 342 corresponds to a single array (entry) 334 in the index 332. In some embodiments, each such array in the target dataset is sized to contain about 1,000 entries. Because it is possible for a specific range to overlap multiple "chunks", the same data may be written into multiple consecutive arrays. Referring to FIG. 3, in some embodiments, the synopsis 308 further comprises an index 336 to the fragment dataset 344. The fragment dataset 344 comprises the length, position, barcode, and phase of all the fragments in the nucleic acid sequencing dataset. A fragment is the nucleic acid from a single partition, as described above. In some embodiments index 336 and fragment dataset 344 are stored in a blocked JSON index. The blocked JSON index includes a single JSON object in the synopsis section (the index 336) and multiple JSON objects in the data section (the fragment dataset 344). The index 336 is used to calculate which data components must be read to fulfill a particular query. In some embodiments, the index 336 of is split up by chromosome. For each chromosome, the index 336 stores an array 338 associating ranges on that chromosome with the offset at which specific data for that range may be found in the fragment dataset 344. An example of a data chunk in the fragment dataset 344 is:

```
{
    "Chromosome" : "chr1",
    "Name" : "19002" ,
    "Info" : {
        "h0" : "0.100000017888" ,
        "h1" : "0.899999982112",
        "hmix" : "0.0\n",
        "phsae_set" : "107163622",
        "ps_start" : "7163622",
        "be" : "CGTICCGTGGTATA-1",
        "ps_end" : "7276533"
        "Stop" : 7235518,
        "Start" : 7213929
}
```

Thus, as the above provides, the disclosed nucleic acid sequencing datasets 126 of the present disclosure provide a streamlined file format that combines several forms of data that is conventionally found in separate files along with data that is of only secondary value. Advantageously, the nucleic acid sequencing dataset 126 file format is self-contained and has all the data required to support the features of haplotype visualization tool 148.

Figure 12A:
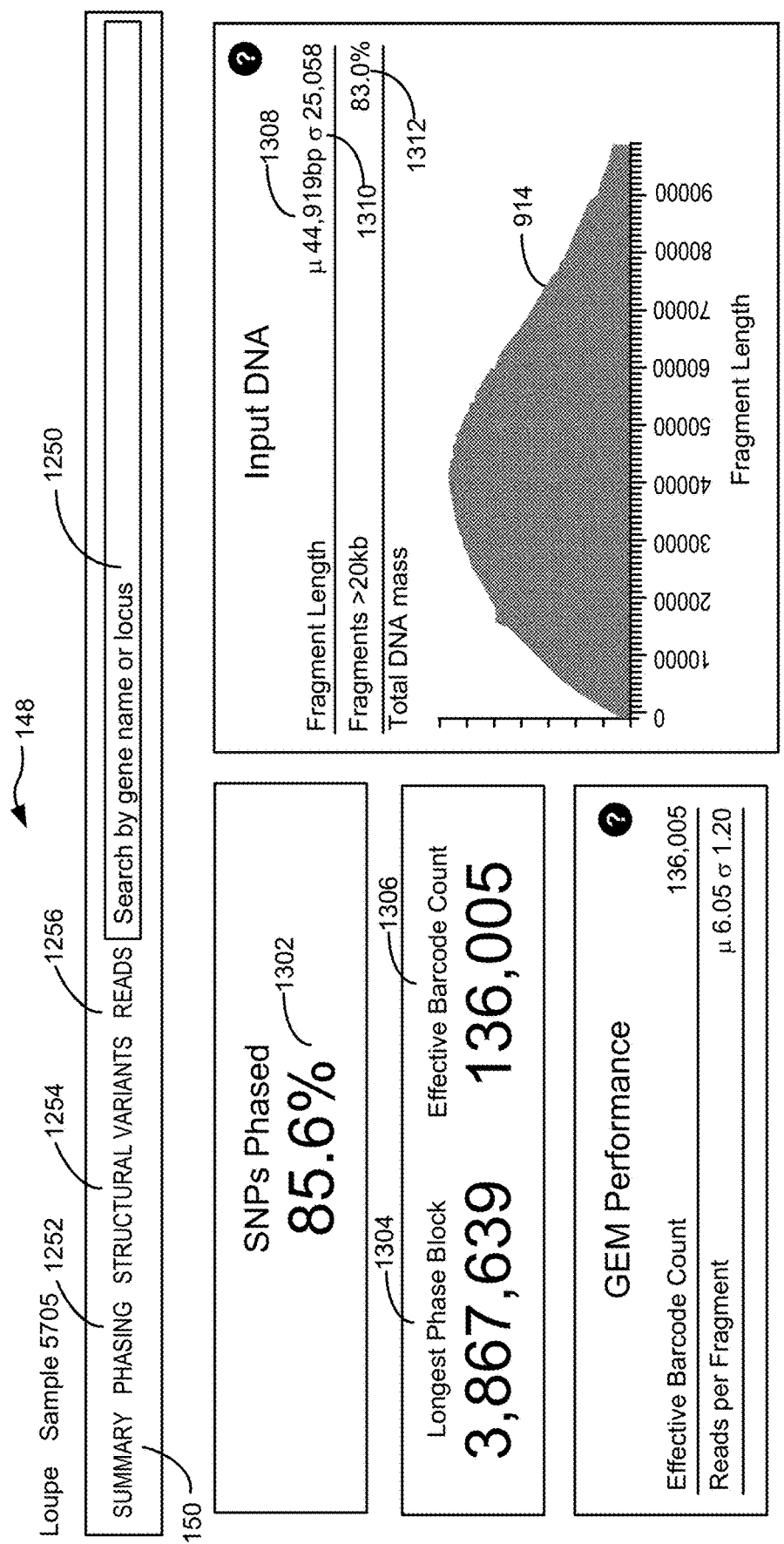
FIGS. 12A and 12B illustrate a summarization module in a haplotype visualization tool in accordance with some embodiments.
Figure 12B:
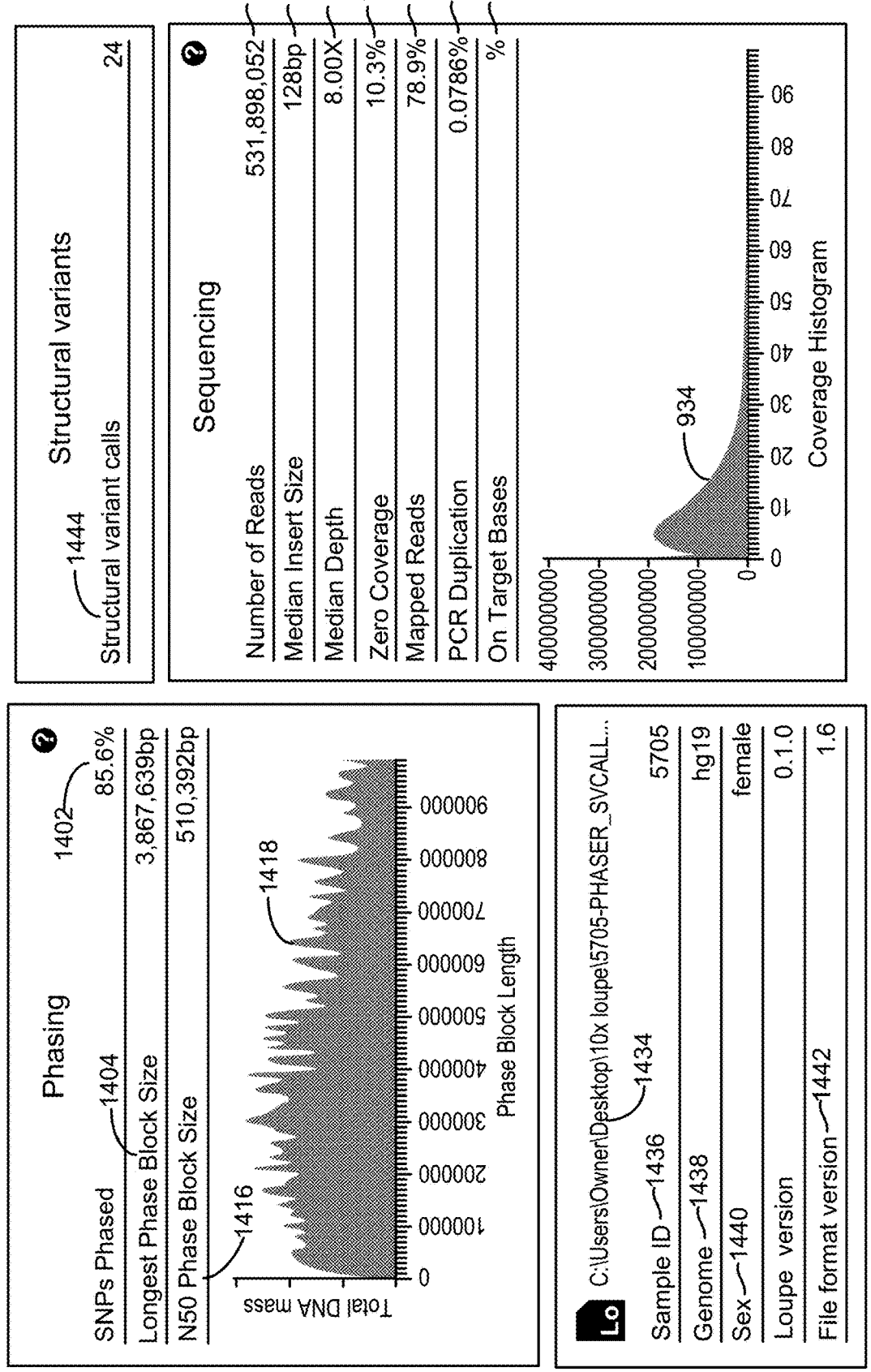
Figure 13A:
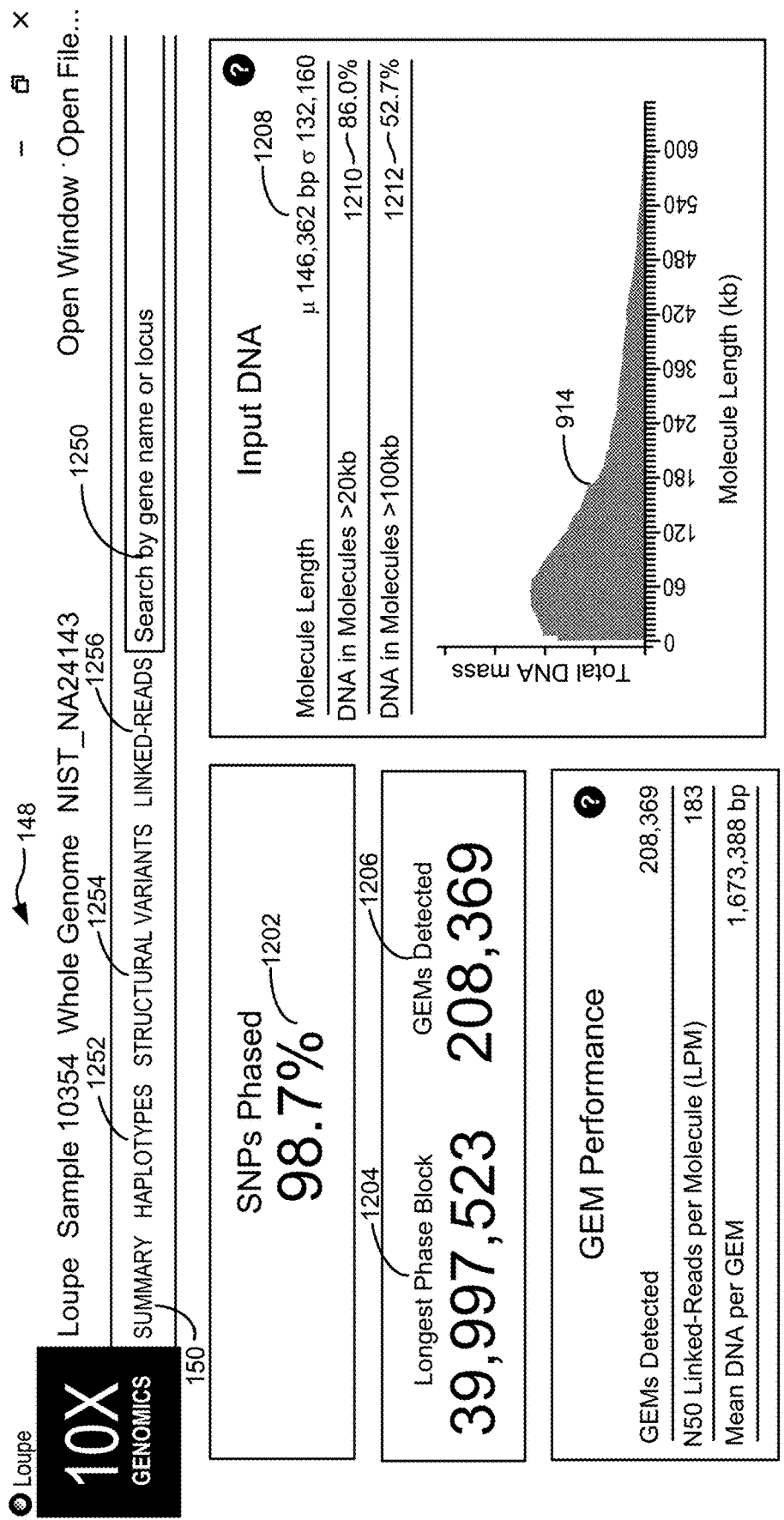
FIGS. 13A and 13B illustrate a summarization module in a haplotype visualization tool in accordance with some embodiments.
Figure 13B:
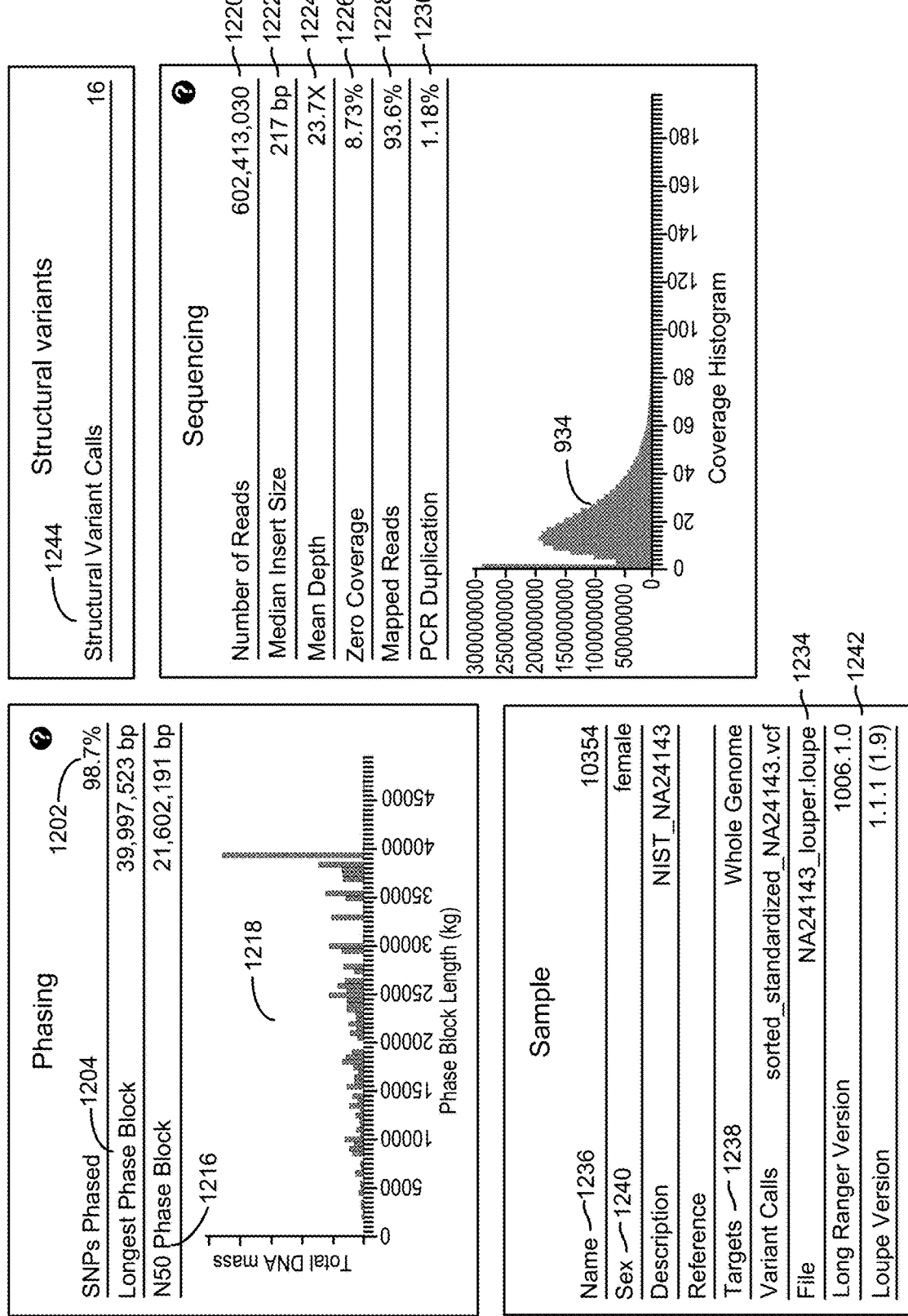

FIGS. 12-30 illustrate an embodiment of the haplotype visualization tool 148 that reads nucleic acid sequencing datasets 126. In some embodiments, the haplotype visualization tool 148 is a variant oriented and haplotype aware genome browser. To produce such views, the haplotype visualization tool 148 overlays data from several sources as tracks into a single unified nucleic acid sequencing dataset 126 for display that can be scrolled and zoomed. In some embodiments, the tracks that are stored includes phased variant calls, phase blocks, genes, exons, structural variant breakpoints and read count (coverage) as tracks. One such embodiment for how such information is stored is disclosed in FIG. 3 and described above. Advantageously the disparate information in the nucleic acid sequencing set can be displayed in a single display. The haplotype visualization tool 148 is distinguished from other genome browsers by its ability to show phasing information. Referring to FIGS. 12 and 13, from the summarization module displayed in FIGS. 12 and 13, a user can advantageously use the search prompt 1250 to select regions of the nucleic acid sequencing dataset for further analysis. In some embodiments, through search prompt 1250, the haplotype visualization tool 148 supports a broad range of valid search syntaxes such as chr1:1000000 (select the first million nucleotides of chromosome 1), chr1:1000000-2000000 (select the second million nucleotides of chromosome 1), BRCA1, BRCA2 (select BRCA1 and BRCA2), and chr1:1000000-2000000, chr2:5000000-6000000 (select the second million nucleotides of chromosome 1 and the fifth million nucleotides of chromosome 2). In some embodiments, the user provides a symbolic name of a gene and the haplotype visualization tool 148 converts this symbolic name to the appropriate genomic coordinates by using one or more lookup tables that convert symbolic names to genomic coordinates. Advantageously, a user can provide in a single search a mix of absolute coordinate ranges and gene names. In some embodiments, a user provides a single search query that includes multiple loci. Responsive to such a query, the haplotype visualization tool 148 parses the multiple loci and provides results for each such query. In some embodiments, the user provides a search query of syntax is $X_1:N_1-N_2$, where $X_1$ is an identity of a selected first chromosome or a selected first contig sequence, $N_1$ is a selected start position within the first chromosome or the selected first contig sequence, and $N_2$ is a selected end position within the first chromosome or the selected first contig sequence. As used in this context, the term "contig" means any "contig" from a reference genome which could correspond to an isolated molecule of interest that isn't a chromosome or an incompletely assembled part of a chromosome. In some embodiments, the user provides a search query of syntax $X_1:N_1-N_2$, where $X_1$ is an identity within a selected first chromosome or a selected first contig sequence, $N_1$ is a selected start position within the first chromosome or the selected first contig sequence, and $N_2$ is a selected end position within the first chromosome or the selected first contig sequence. In some embodiments, the user provides a search query of syntax $X_1:N_1$, where $X_1$ is an identity of a selected first chromosome or a selected first contig sequence, and $N_1$ is a number of nucleotides, beginning at the origin of the first chromosome or the selected first contig sequence.

In some embodiments, a user provides a search query of syntax $Y_1, Y_2, \ldots, Y_N$, where each $Y_i$ in $Y_1, Y_2, \ldots, Y_N$ is either an alphanumeric identification of a selected gene, a selection of a chromosomal region, or selection of a region of a contig sequence. In some such embodiments, a first $Y_i$ in $Y_1, Y_2, \ldots, Y_N$ is an identity of a first chromosome or a first contig sequence having the syntax $X_1:N_1-N_2$, where $X_1$ is an identity of the first chromosome or the first contig sequence, $N_1$ is a selected start position within the first chromosome or the first contig sequence, and $N_2$ is a selected end position within the first chromosome or the first contig sequence, and a second $Y_i$ in $Y_1, Y_2, \ldots, Y_N$ is an alphanumeric identification of a selected gene. In other such embodiments, a first $Y_i$ in $Y_1, Y_2, \ldots, Y_N$ is an identity of a first chromosome or a first contig sequence having the syntax $X_1:N_1-N_2$, where $X_1$ is an identity of the first chromosome or the first contig sequence, $N_1$ is a selected start position within the first chromosome or the first contig sequence, and $N_2$ is a selected end position within the first chromosome or the first contig sequence, and a second $Y_i$ in $Y_1, Y_2, \ldots, Y_N$ is an alphanumeric identification of a selected gene. In some embodiments, the request is converted, without human intervention, to genomic coordinates by comparison of the request against one or more lookup tables that match alphanumeric entries of genes to genomic coordinates. In some embodiments, the request comprises one or more gene names, one or more genomic coordinates, or a combination thereof.

Figure 32:
FIG. 32 is an example of a credential challenge for remote initiation of an instance of a haplotype visualization tool in accordance with the disclosed embodiments.

Advantageously, the haplotype visualization tool 148 can be invoked in a variety of different system topologies. For instance, referring to FIG. 31, in some embodiments, the haplotype visualization tool 148 operates on a client computer 3102 and accesses the nucleic acid sequence dataset remotely across a network connection. For instance, referring to FIG. 31, in some embodiments, the haplotype visualization tool 148 tool is on a client computer system 3102 that communicates with the structural variation and phasing visualization system 100 across a network connection 3106. One such embodiment of the present disclosure provides a system 3100 for providing structural variation or phasing information 3100 over a network connection to a remote client computer 3102. Referring to FIGS. 1 and 32, the system 3100 comprises a server 100 having one or more microprocessors 102, a persistent memory (e.g., hard drive) and a non-persistent memory (e.g., random access memory). One of skill in the art will appreciate that persistent memory is memory that stores information even when system 100 is powered down whereas non-persistent memory is not able to store information when system 100 is powered down. Moreover, one of skill in the art will appreciate that access times to data stored in persistent memory is slower than access times to data stored in non-persistent memory. Further still, non-persistent memory is more expensive than persistent memory. As such, the disclosed nucleic acid datasets 126, which are large, are typically relegated to storage in persistent memory. In some embodiments, a nucleic acid sequencing dataset is 1 gigabyte or larger, 5 gigabytes or larger, or 10 gigabytes or larger.

In some embodiments, the persistent memory and the non-persistent memory, collectively referenced as memory 112 in FIG. 1, store one or more nucleic acid sequence datasets 126. Each respective nucleic acid sequencing dataset 126 in the one or more nucleic acid sequence datasets corresponds to at least one target nucleic acid in a respective sample in a plurality of samples. The respective sample is associated with a genome of a species. Referring to FIG. 3, the respective nucleic acid sequencing dataset 126 comprises (i) a header 302, (ii) a synopsis 308, and (iii) a data section 340.

The data section 340 comprises a plurality of sequencing reads and is the largest component of the dataset 126. Each respective sequencing read in the plurality of sequencing reads comprises a first portion that corresponds to a subset of at least one target nucleic acid in the respective sample and a second portion that encodes a respective identifier for the respective sequencing read in a plurality of identifiers. Each respective identifier is independent of the sequence of the at least one target nucleic acid. The plurality of sequencing reads collectively includes the plurality of identifiers.

The persistent memory and the non-persistent memory further collectively store one or more programs that use the one or more microprocessors 102 to provide a haplotype visualization tool 148 to the client for installation on the remote client computer. In turn, a request, sent from the client over the network connection, is received for structural variation or phasing information using a first dataset 126 in the one or more datasets. Responsive to receiving the request, the request is automatically filtered by loading the header 302 and the synopsis 308 of the first dataset into the non-persistent memory if not already loaded into the non-persistent memory while retaining the data section 340 in persistent memory. In this way, the amount of non-persistent memory is minimized. The request is compared to the synopsis 308 of the first dataset thereby identifying one or more portions of the data section of the first dataset. In particular, the various components of the synopsis 308, as described in further detail below, are used to identify which portions of the data 340 are needed to fulfill the request. In some embodiments, the request identifies a particular dataset 126 and a region of a genome. In some embodiments, the request identifies a particular dataset 126 and one or more genes. In some embodiments, the request identifies a particular dataset 126 and one or more exons. Once the portions of the data section that are needed to fulfill the request are identified, they are loaded into non-persistent memory and the requested structural variation or phasing information is formatted for display on the client computer 3102 using the first dataset. This formatted structural variation or phasing information is then sent over the network connection 3106 to the client device for display on the client device. In some embodiments, as disclosed in FIG. 1, a client computer is not used and the haplotype visualization tool is resident on the structural variation and phasing visualization system 100.

Figure 15:
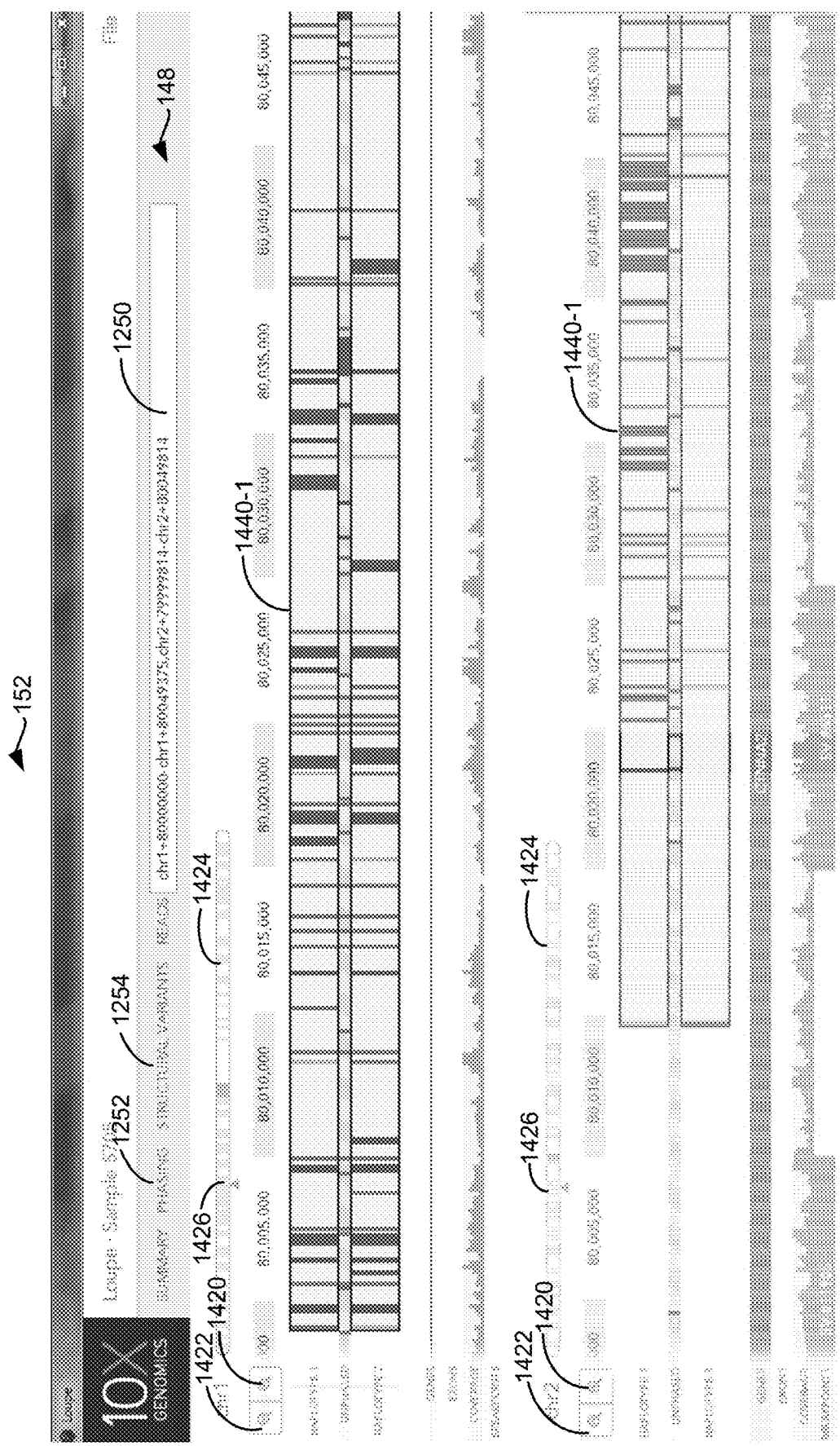
FIG. 15 illustrates another screen shot of a phase visualization module in a haplotype visualization tool in accordance with some embodiments.
Figure 16:
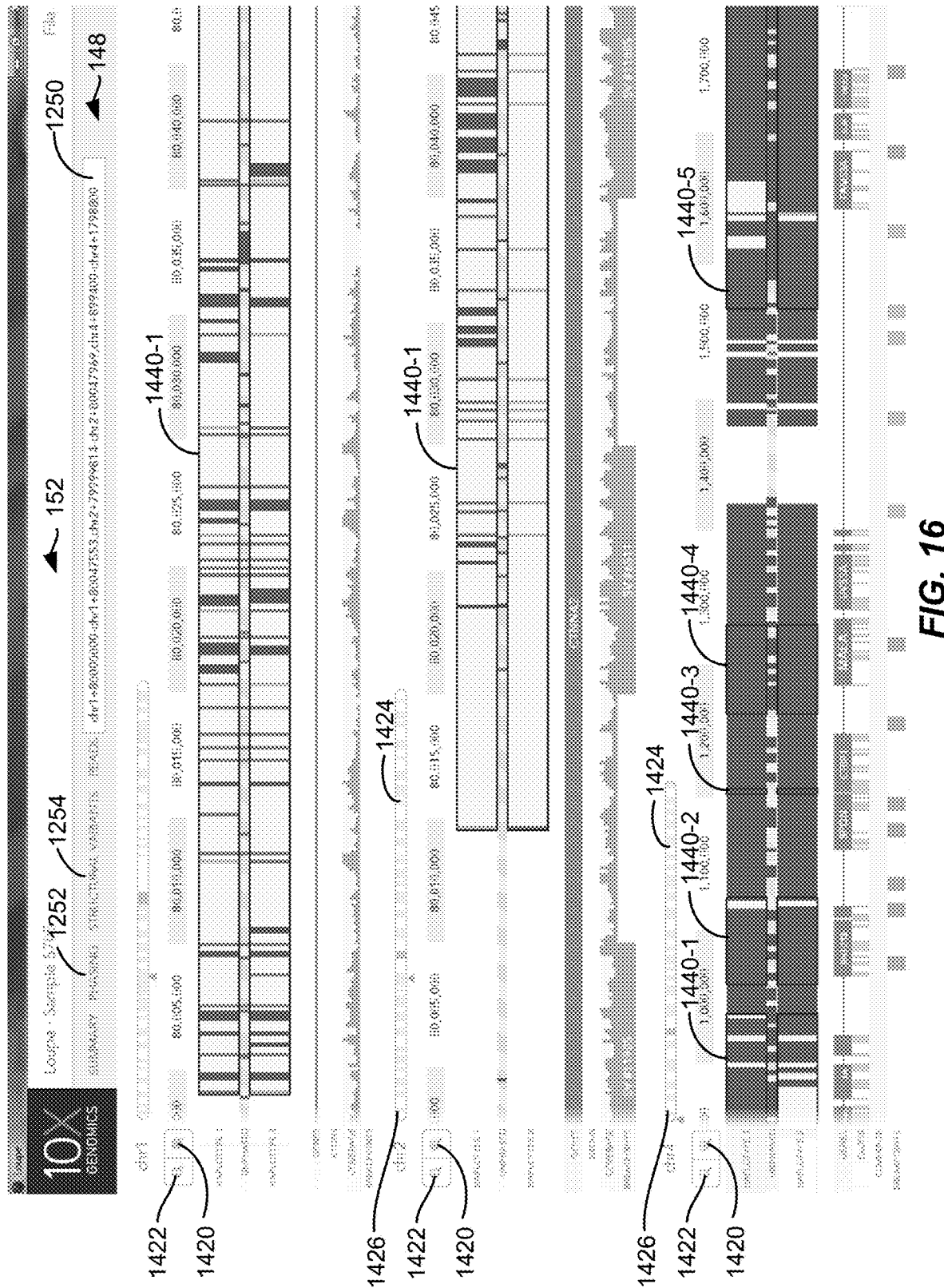
FIG. 16 illustrates another screen shot of a phase visualization module in a haplotype visualization tool in accordance with some embodiments.

Now that advantages of splitting up the nucleic acid sequence dataset 126 have been explained, graphical user interface features of the haplotype visualization tool 148, and its component modules (e.g., summarization module 150, phase visualization module 152, structural variations module 154, etc.) will be described in further detail. Turning to FIG. 12, once a user has entered a query in panel 1250 phase visualization module 152 may be used to view the phase of the query as illustrated in FIGS. 14 through 16. For instance, upon entering the query chr1+10000000-chr1+10500000 (or chr1:10000000-chr1:10500000), the selected region is illustrated in the genome browser (phase visualization module 152) illustrated in FIG. 14A. Here, the selected region of the genome is advantageously shown in a way that reflects the actual physical structure of the selected region: there are two copies of the genome, and this is reflected by showing two tracks, one for each haplotype— haplotype 1 (1402) and haplotype 2 (1404), and a middle area 1406 where the parental haplotype has not been determined. Small insertions and deletions are mapped to each haplotype based on phasing algorithms. Portions of the selected region that have been phased to the first haplotype are shown as bars in the corresponding portion of the first haplotype 1 region 1402, portions of the selected region that have been phased to the second haplotype are shown as bars in the corresponding portion of the second haplotype 1 region 1404, and portions of the selected region that have not been phased to a haplotype are shown as bars in the middle area 1406.

In the haplotype view, phased portions of the selected region are enclosed in black rectangular boxes 1440. The entire region illustrated in FIG. 14A is in a single phase block 1440-1. This also the case for FIG. 14B, FIG. 15, and chromosomes 1 and 2 of FIG. 16. However, the displayed region of chromosome 4 in FIG. 16 includes five different phase blocks, each demarked by a black rectangular box. These boxes demarcate phased blocks, a contiguous phased region of the chromosome as determined by phasing algorithms.

Vertical bars in the haplotype 1 (1402), haplotype 2 (1404), and middle area 1406 represent single nucleotide polymorphisms, small insertions and deletions. In some embodiments, these bars are color coded with a first color (e.g. grey) representing the reference genotype, and a second color (e.g., green) representing the alternative genotype.

A homozygous SNP will have a vertical bar spanning the two haplotype tracks and the middle area (unphased track) since homozygous variants cannot be phased. This is illustrated as element 2602 in FIG. 26.

Phased heterozygous SNPs are placed on the haplotype tracks 1402/1404. This is illustrated as element 2604 in FIG. 26.

Heterozygous SNPs are placed in the middle area 1405 (unphased track) sandwiched in between the haplotype tracks 1402/1404 when they are not phased. This is illustrated as element 2606 in FIG. 26.

Finally, if both phased single nucleotide polymorphisms are of alternative genotype, two vertical bars of the second color (e.g., green) will be displayed in the haplotype tracks 1402/1404, one for each track. This is illustrated as element 2608 in FIG. 26.

Figure 27:
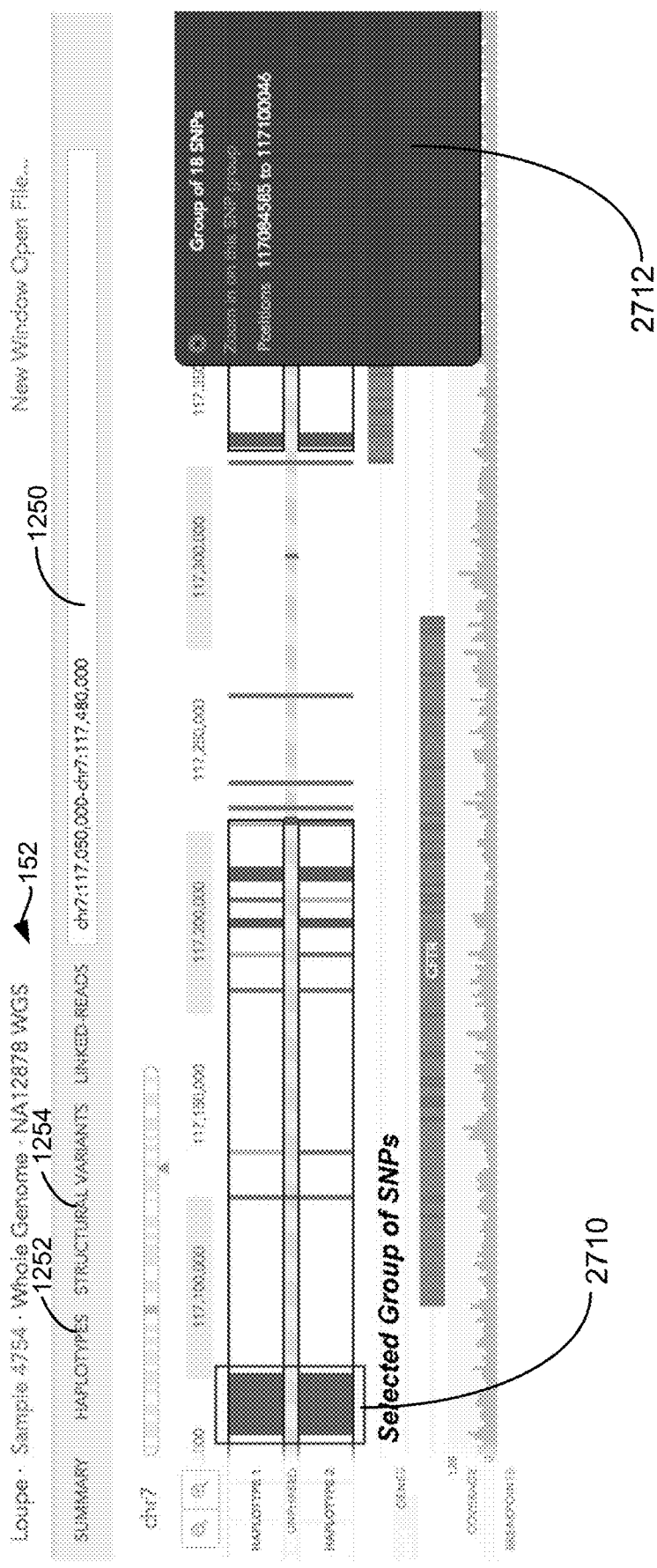
FIG. 27 illustrates another aspect of a phase visualization module in a haplotype visualization tool in accordance with some embodiments.

Dark regions, such as region 2710 of FIG. 27, of the haplotype track represent areas with high SNP density. Clicking on a region 2710 zooms into individual SNPs within the region 2710. Furthermore, in some embodiments, when this is done, a pop-up box 2712 will appear with a link allowing the user to zoom in on the SNP group. In general, the box 2712 provides additional information on the SNP, such as position, the reference genotype, observed genotypes of haplotype 1 and 2 in the sample, the gene where SNP is found (if associated with a gene), phasing quality, and allele counts of the two observed genotypes. The box 2712 can be dismissed by clicking on an X on a corner of the box. In some embodiments, the phasing quality provided for the SNP is a Phred-like score used to quantify the phasing quality of a SNP.

Referring to FIG. 28A, when a user clicks on one of the alleles for a variant, a rectangular box (e.g., rectangular box 2802) highlights that variant. The number 2804 displayed next to the highlighted variant represents the number of barcodes that are associated with the selected allele for that variant. For instance, in FIG. 28A, the number "31" is displayed next to box 2802 indicating that the number of barcodes that are associated with the selected allele for that variant is 31. There are also numbers displayed on the top and/or bottom of variants adjacent to box 2802. Each such number represents the number of barcodes that overlap between the selected allele and one of the two alleles of the adjacent variants. Numbers displayed in a first color (e.g., black) agree with the phasing call of the variant 2802, while numbers displayed in a second color (e.g., red) disagree with the call. The greater the barcode overlap there is between neighboring variants, the more confidence there is in the phasing of the variant. As an example, for the reference call at Chr7: 117,216,030 of FIG. 28A, there is a 31 (2804) on the top of the haplotype 1 panel 1402, indicating there are 31 barcodes associated with the reference allele at that position. Referring to FIG. 28B, when the variant SNV at the same position 2802 is selected, 13 barcodes support the phasing and the labeled neighboring SNVs change as seen in FIG. 28B.

In some embodiments the genome browser further provides a chromosome map 1424 and the location 1426 on the chromosome that is being displayed. Referring to FIG. 14A, at the top of the browser, a miniature chromosome 1424 with the centromere marked by a dark rectangle is shown with chromosome bands marked by light rectangles. A triangle 1426 indicates the location currently in zoom, giving the user an overall view of the region selected using search bar 1250 with respect to the rest of the chromosome.

Figure 26:
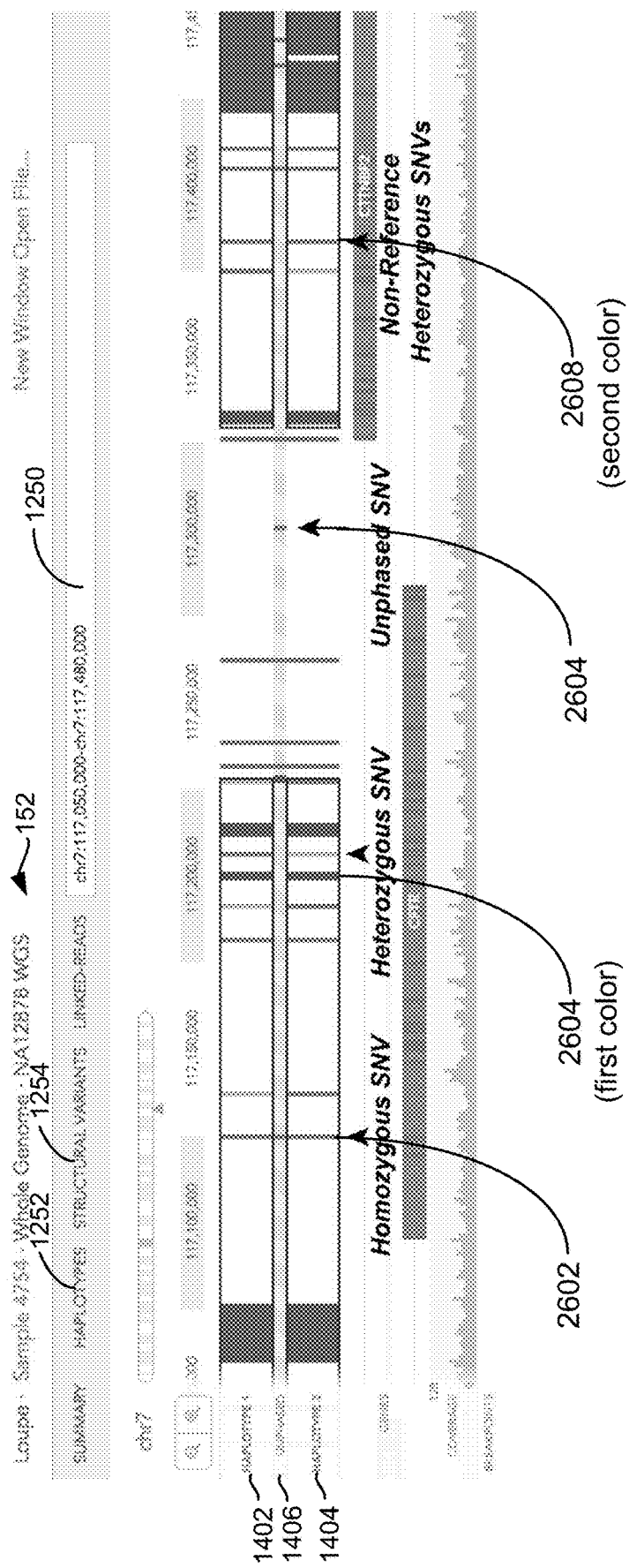
FIG. 26 illustrates a phase visualization module in a haplotype visualization tool in accordance with some embodiments.

The disclosed genome browser further provides a graphic representation 1408 of each gene that is in the displayed genomic region. This genes track 1408 displays annotated reference genes. Multiple genes can be displayed using the search bar 1250 by entering the genes of interest. The direction of each gene is indicated with arrows. Although not illustrated in FIG. 14A, exons are highlighted with dark shades. This feature is illustrated in FIGS. 26-28. In some embodiments, overlapping genes are shown on a maximum of three tracks in the genes track 1408 but many genes may be displayed using the search bar.

The disclosed genome browser further provides a graphic representation 1410 of exons that are in the displayed genomic region.

The disclosed genome browser further provides a coverage track 1412 for the coverage in the displayed genomic region. Aligned sequence reads are shown on the coverage track. Each vertical bar in the coverage track 1412 shows the average coverage-per-base for the area of the genome under the bar. The height is scaled such that maximum height is four times the median coverage. In some embodiments, when a user clicks on a portion of the coverage track 1412, the mean reads per base pair and total number of reads is displayed in a coverage details pop-up black box for that portion of the coverage track.

Figure 29:
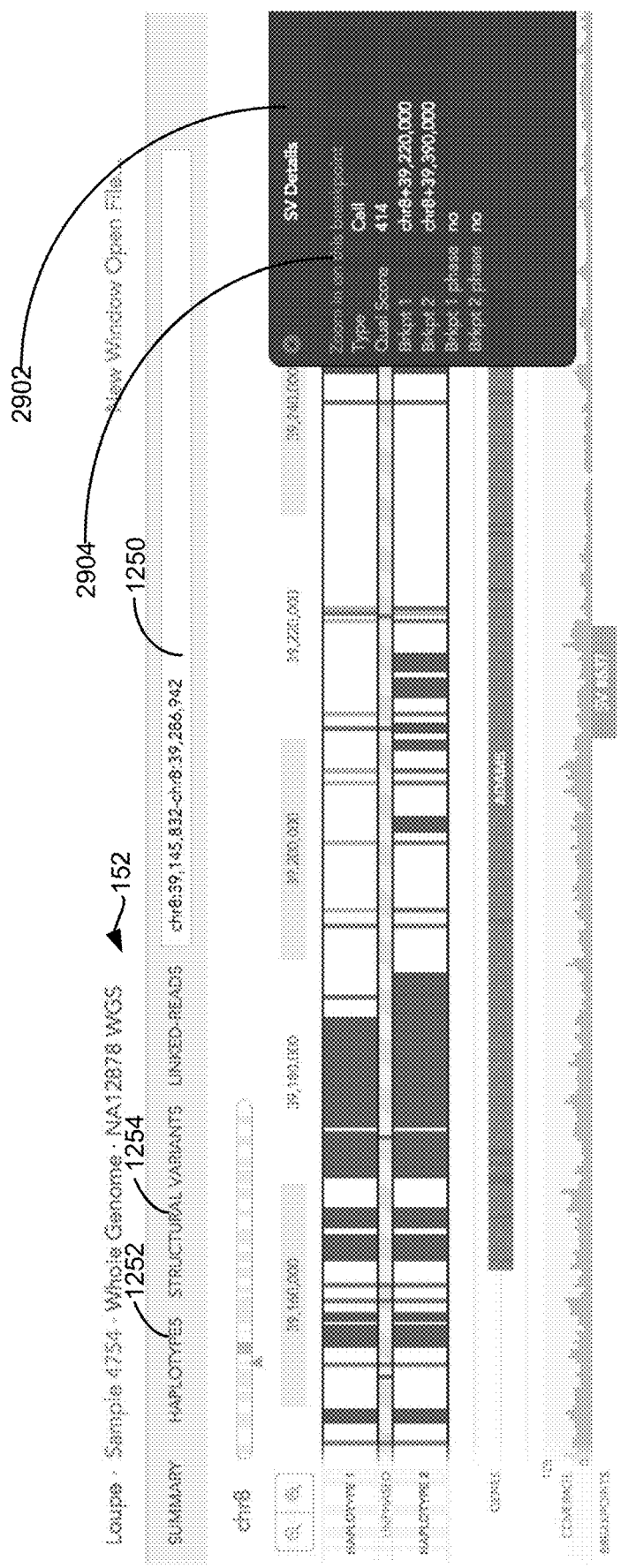
FIG. 29 illustrates another aspect of a phase visualization module in a haplotype visualization tool in accordance with some embodiments.
Figure 30:
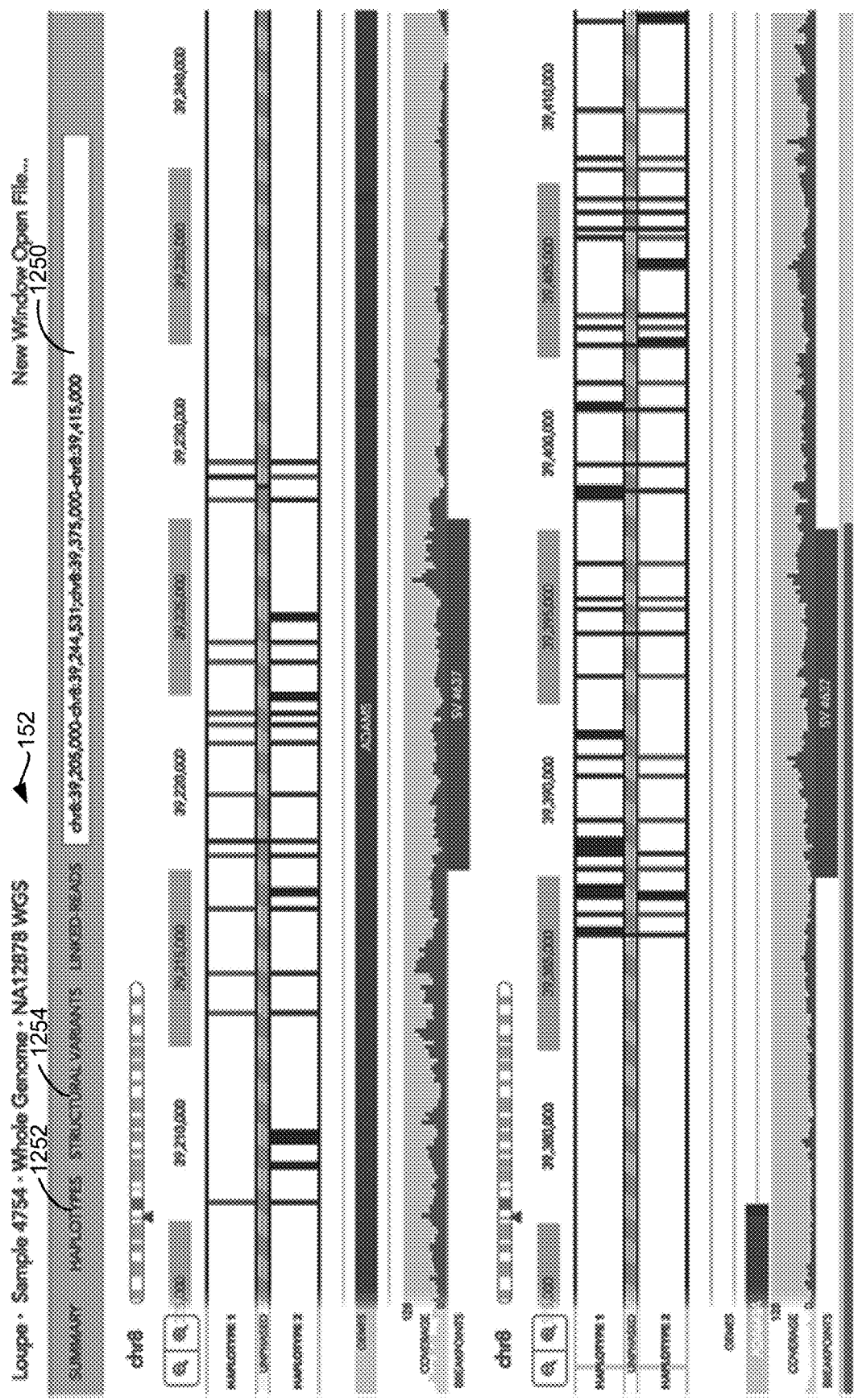
FIG. 30 illustrates another aspect of a phase visualization module in a haplotype visualization tool in accordance with some embodiments.

The disclosed genome browser further provides a breakpoints track 1414 in the displayed region. Structural variants including inter-chromosomal translocations, gene fusions, inversions and deletions are highlighted in the breakpoints track 1414. Structural variants are arbitrarily numbered in the display. Structural variant call are indicated in a first color (e.g., orange) in the breakpoints track 1414 and structural variant candidate are specified in a second color (e.g., grey) in the breakpoints track 1414. To display structural variant breakpoint pairs, a user can click on the structural variant displayed for the gene, as illustrated in FIG. 29. The structural variant is displayed in the details box 2902. By selecting "Zoom in on this breakpoint" 2094 in details box 2902, the other side of the breakpoint is brought up as an additional haplotype track, zoomed to the breakpoints, as illustrated in FIG. 30.

Advantageously, what is not shown in some embodiments of the display mode of the disclosed genome browser, illustrated in FIG. 14A, are base calls, error rates, specific reads, and alignments. Rather, the disclosed genome browser operate at a higher level in order to provide a more conceptual indication of what is going on in the selected region and to provide this information in a way that is easy to understand. For this reason, some embodiments of the disclosed browser provide a display mode, such as the display mode illustrated in FIG. 14A, in which all of the sequence read data is not shown.

Referring to FIG. 14A, zoom affordance 1420 can be used zoom into a subset of the region identified by search bar 1250 and zoom affordance 1422 can be used to zoom out of the region. In addition, a user can zoom in to a specific gene by clicking on the icon in region 1408 representing the specific gene.

In some embodiments, the search bar 1250 of the disclosed genome browser provides intelligent auto complete features. For instance, when a user starts typing a gene name in the search bar 1250, the genome browser auto completes on the genes. In some embodiments, the genome browser accomplishes this by comparing partial search queries that the user enters against genomic information stored in the nucleic acid sequencing dataset such as the names of genes in the gene track. Advantageously, in such embodiments the search bar 1250 auto completes on gene names. For instance, referring to FIG. 17, when a user enters the expression "atp" into the search bar, several possible matches 1702-1 through 1702-10 found within the nucleic acid sequence dataset 126 are displayed.

As illustrated in FIGS. 12 through 30, the haplotype visualization tool 148 provides structural variation or phasing (e.g. haplotype) information for a nucleic acid sequence dataset.

In particular, referring to FIGS. 12 and 13, selection of the phasing/haplotypes toggle 1252 of the haplotype visualization tool 148 invokes the phase visualization module 152 as illustrated in FIGS. 14-17 and FIGS. 26-30. As illustrated in FIGS. 14-17 and FIGS. 26-30, visually separated tracks for haplotypes as well as a virtual track for variants that could not be assigned to either haplotype is provided. Phased variants can have a wide number of classifications including: unphased, homozygous, and/or heterozygous-with-no-reference-reads, heterozygous-with-reference-reads. The haplotype visualization tool 148 applies visually distinct stylings to these different configurations so that a user can quickly tell them apart. The haplotype visualization tool 148 can display the amount of barcode evidence used in assigning a variant to a particular phase block. In some embodiments, when the user "clicks" on a variant, every other visible variant is decorated with the count of barcodes that overlapped with the selected variant. Data that contradicts the called haplotype is highlighted. The haplotype visualization tool 148 also allows the user to view multiple regions at once. This is displayed as separate haplotype in different areas of the screen. In this mode "counts" are shared between each displayed region allowing the user to view barcodes overlaps between distant regions of the genome.

Again referring to FIGS. 12 and 13, selection of the structural variants toggle 1254 of the haplotype visualization tool 148 invokes the structural variants module 154 as illustrated in FIGS. 23-25 and 33-34. The matrix view provided by the structural variants module 154 encompasses a method for visualizing candidate structural variants. The visualization works by quantifying two (possibly overlapping) regions of the genome (test nucleic acid data) into chunks of between 100 and 10,000 base pairs per chunk. The number of shared barcodes between the reads in every pair of chunks is computed. The resulting matrix (with the chunks from one region as the rows and the other region as the columns) can be displayed as a two dimensional image (heat map), as illustrated in FIGS. 23-25 and 33-34. In some embodiments, the color of a pixel corresponds to number of distinct overlapping barcodes between a specific chunk (e.g. window) of each region. For example, consider two regions with consecutive chunks with the following barcodes:

| (1) | AAA, ACA | ACA, AGT | GTG |
| (2) | GTG, AAA | CCC | ACA, AAA |

There are nine pairs of chunks between region (1) and region (2) which can be placed in a matrix such as the one set forth below in Table 1.

TABLE 1 matrix of pairs of chunks between region (1) and region (2).

| | (1) | | |
|---|---|---|---|
| (2) | AAA, ACA vs GTG, AAA | AAA, ACA vs CCC | AAA, ACA vs ACA, AAA |
| | ACA, AGT vs GTG, AAA | ACA, AGT vs CCC | ACA, AGT vs ACA, AAA |
| | GTG vs GTG, AAA | GTG vs CCC | GTG vs ACA, AAA |

Computing the overlap between the two sets of barcodes in each cell yields the values set forth in Table 2.

TABLE 2 matrix values between region (1) and region (2).

| | (1) | | |
|---|---|---|---|
| (2) | 1 | 0 | 2 |
| | 0 | 0 | 1 |
| | 1 | 0 | 0 |

Table 2 can be displayed by the structural variants module 154 as a heat map which efficiently shows areas of low and high barcode correlation to the user. In some embodiments, the structural variants module 154 provides additional information, such as gene and exon boundaries overlaid with the matrix to allow easy alignment of the data to known places of interest. In some embodiments, the structural variants module 154 also allows a textual copy of the matrix to be downloaded for analysis with other computer programs. In some embodiments, the user may adjust the region of the genome that is visualized in the structural variants module 154 by scrolling or zooming in real time. In some embodiments, the user can adjust the resolution (chunk size/window size) to avoid aliases or overload when looking at very small or very large areas of the genome.

Some embodiments of the present disclosure provide a system 100 for viewing nucleic acid sequencing data (e.g., information obtained from nucleic acid sequencing datasets 126). The system 100 comprises one or more microprocessors 102 and a memory 112. The memory stores a nucleic acid sequence dataset 126 corresponding to at least one target nucleic acid in a sample. The memory further stores one or more programs (e.g., the haplotype visualization tool 148) that use the one or more microprocessors to obtain the nucleic acid sequencing dataset that comprises a plurality of sequencing reads from a sample. Then, a request is obtained from a user (e.g., through search bar 1250 of the haplotype visualization tool 148 illustrated in FIGS. 12 and 13) that specifies a genomic region represented by the nucleic acid sequencing dataset. Advantageously, this request can be in any of the syntaxes disclosed in the present disclosure. In some embodiments, the genomic region in the request is an entire chromosome. In some embodiments, the genomic region in the request is between 100 and 10000 bases of the chromosome. In some embodiments, the genomic region in the request is between 10 and $1 \times 10^5$ bases of the chromosome. In some embodiments, the genomic region in the request is between 10 and $1 \times 10^6$ bases of the chromosome. In some embodiments, the genomic region in the request is between 10 and $1 \times 10^7$ bases of the chromosome. In some embodiments the request is for a gene in the genome of the sample. Responsive to obtaining the request, the request is parsed by obtaining a plurality of sequencing reads 1048 within the genomic region of the request from the nucleic acid sequencing dataset 126. Next, a scan window is run against the plurality of sequencing reads thereby creating a plurality of windows, each respective window of the plurality of windows corresponding to a different region of the genomic region in the request and including an identity of each identifier (e.g., bar code) of each sequencing read in the different region of the genomic region in the nucleic acid sequencing dataset. Further, referring for example to FIG. 34, a two dimensional heat map 3312 that represents each possible window pair in the plurality of windows is displayed. Each respective window pair is displayed in the two dimensional heat map as a color selected from a color scheme based upon the number of identifiers in common in the respective window pair. It will be appreciated that window size will depend on the amount of the genome the user has requested to visualize. In some embodiments, when the user has requested to visualize a small region of the genome, smaller windows sizes are used and when the user has requested to visualize a larger region of the genome, larger window sizes are used.

Figure 33:
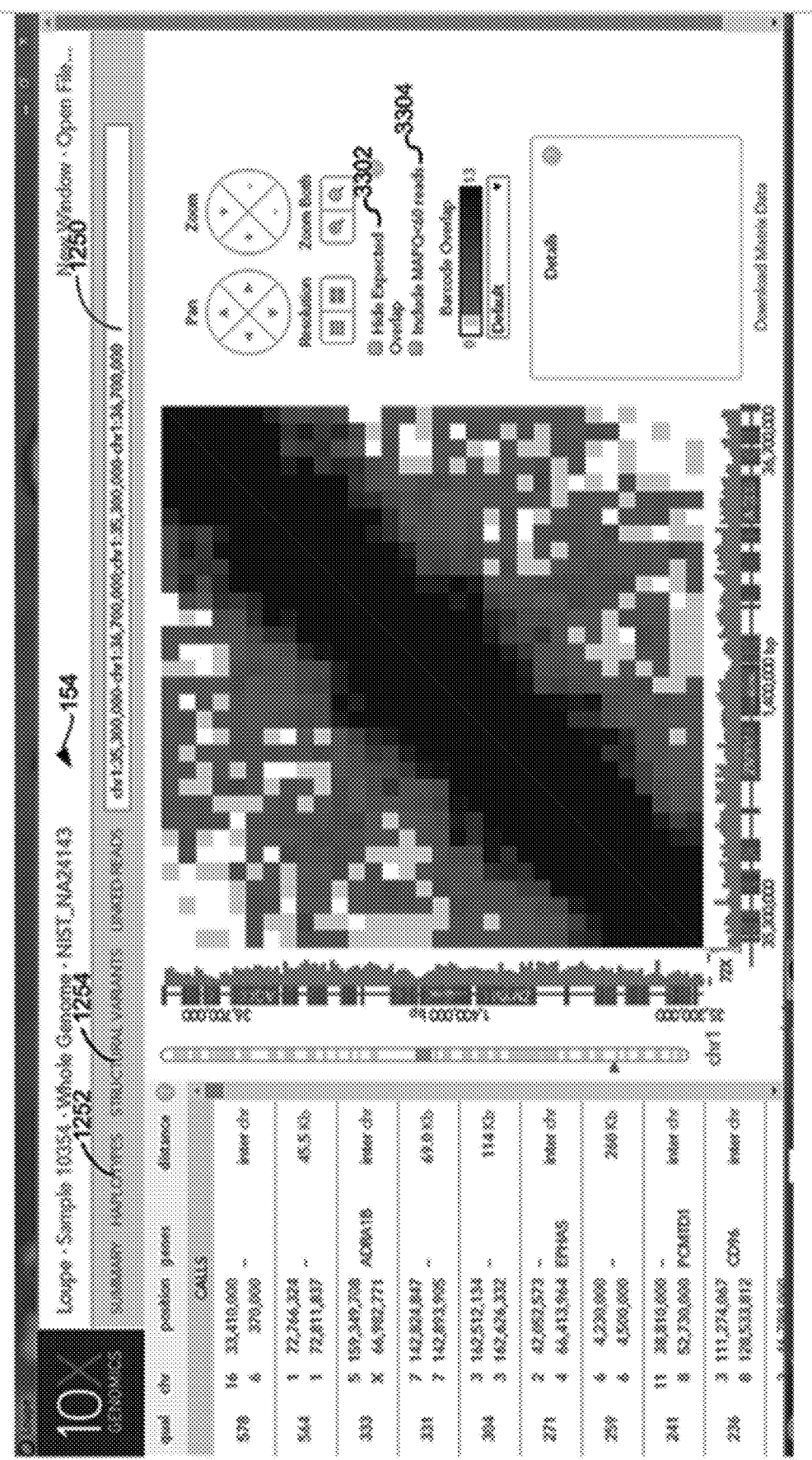
FIG. 33 illustrates a structural variants module in a haplotype visualization tool in accordance with some embodiments in which a sequence read filter is turned off.
Figure 34:
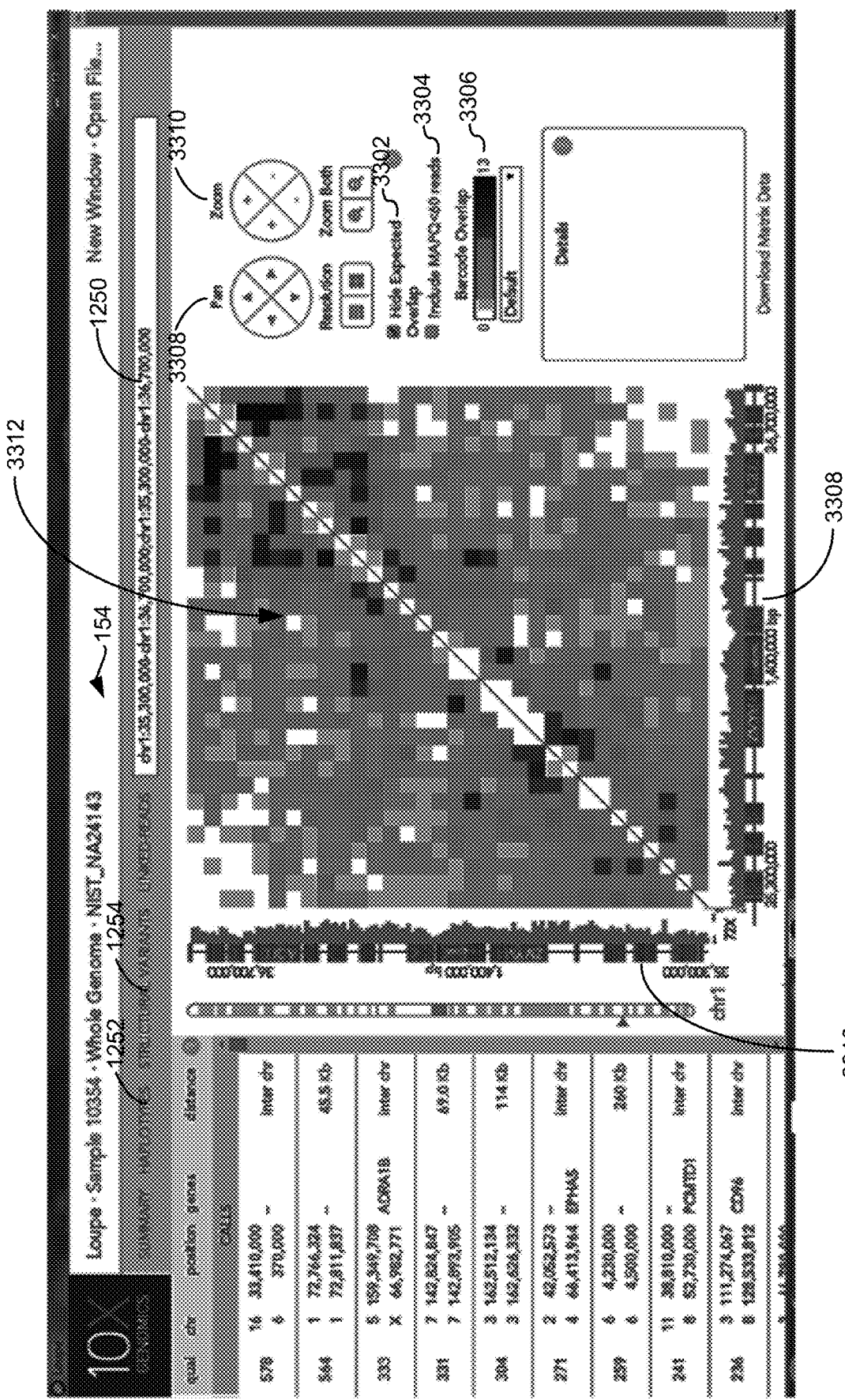

Referring to FIGS. 33 and 34, affordances 3302 and 3304 provide unique tools to clarify the displayed information. First, selection of the "hide expected overlap" affordance 3302 causes the bar code overlap signal that is expected from the genome being in a normal state, where bar codes associated with reads that are next to each other because they are supposed to be, to be hidden. Compare FIG. 33, with affordance 3302 not selected, with FIG. 34, with affordance 3302 selected. The view provided when affordance 3302 is selected is intended to emphasize those parts of the genome that are now touching each other that are unexpected. For instance, this view highlights a structural variation, a trans location from one chromosome to another that, based on the reference genome, you wouldn't expect to be there but suddenly the bar codes now shows the association. As such, affordance 3302 activates a filter that hides the normal signal and highlights the unexpected signals. In other words, the number of identifiers in common in respective window pairs is down-weighted to remove bar code signals arising from bar codes that are expected to be proximate to each other based on the reference genome sequence. In some embodiments, the filter associated with affordance 3302 considers the mean length of the fragments of the target nucleic acid that were sequenced (e.g. 50 kb). Bar codes that are within this threshold distance of the mean length of fragments do not contribute to the heat map when affordance 3302 is activated. In some embodiments, the filter is enabled by taking the entire set of bar codes in the nucleic acid sequencing dataset 126 that have been aligned against a reference genome. Then, only those regions along the reference genome that exhibit a gap that is greater than the mean fragment length displayed. As such, the affordance 3302 filter act to filter out the expected and highlights the differences between the bar code data and a reference genome.

Referring to affordance 3304, each respective sequence read 1048 is mapped to a location on a reference genome with a confidence value that represents a probability that the respective sequence read was correctly mapped. The default is to only show data for sequence reads when this confidence value satisfies a stringent (high) threshold value so that misleading information is not displayed. But sometimes a user still wants to see information for sequence reads that do not satisfy the stringent threshold confidence value. For instance, sometimes, when too much data is filtered out based on the confidence threshold unusual artifacts may appear in the heat map. For instance, regions of the heat map will appear to have no data. In reality, such regions may be just regions where the confidence in the localization of sequence reads 1048 is low (e.g., regions of the genome that exhibit extensive repeats). To determine whether there is actual no data (perhaps indicating an extensive structural variation) affordance 3304 allows the user to remove (or lower) the stringent threshold value and to permit the display of data from sequence reads 1048 that have been mapped to the reference genome with lower confidence values. In this way, the user can determined whether there is in fact a structural variation at sites that were missing data when the stringent threshold value was turned on or whether the genomic region simply represents a region where the confidence values for the sequence reads is low.

In a typical use case scenario associated with affordance 3304, sequence reads 1084 that that do not satisfy a quality threshold are discarded and so are not used to in downstream phasing algorithms and structural variation algorithms. The consequence of discarding such sequence reads is that it can introduce what looks like structure in the heat map plot illustrated in FIGS. 33 and 34. For instance, some regions of the map may lighten up and some lines may be introduced giving rise to the question of whether there something happening in the actual sample that's causing this to change the signal. By selecting affordance 3304, the discarded reads are put back into the phasing and/or structural variation algorithms regardless of their quality score to see if this causes removal of the observed artifacts in the plot. In this way, artifacts of the data can be teased out so that when a region of the plot is missing, before and after applying affordance 3304, confidence that the observed artifact represents an artifact (e.g., structural variation) in the at least one target nucleic acid in a respective sample or an artifact arising from discarding data from sequence reads 1048.

Referring to FIG. 34, the extent of barcode overlap between respective regions of the target nucleic acid is signified on a color scale 3406 by the number of barcodes (from sequence reads localized to the respective regions of the target nucleic acid) that overlap. Thus, in some embodiments, a color scheme is used, with each particular color in the color scheme uniquely representing a certain number of overlapping barcodes. For instance, if a first and second section of the target nucleic acid have in common a first number of barcodes, the color associated with the first number in the color scheme is used to represent the combination of the first and second section of the target nucleic acid. As illustrated in FIG. 34, the X axis 3308 and Y axis 3310 each represent the target nucleic acid and thus the coordinates of the first and second section of the target nucleic acid within the target nucleic acid define an X,Y position in the two dimensional grid, and the color associated with the value of the first number of barcodes is used to color this X,Y position in the two dimensional grid in accordance with the color scheme. In some embodiments, when a first and second section of the target nucleic acid have no barcodes in common, the color scheme dictates that the color used for the X,Y position that represents the combination of the first and second section of the target nucleic acid be white. In some embodiments, when a first and second section of the target nucleic acid have only a few barcodes in common (e.g, in various embodiments, only one barcode in common, only two barcodes in common, only three barcodes in common, only four barcodes in common or only five barcodes in common), the color scheme dictates that the color used for the X,Y position that represents the combination of the first and second section of the target nucleic acid be grey. That is, in such embodiments, the first position in the color scheme is white, meaning no shared barcodes and the second position in the color scheme is grey, meaning a minimal set of barcodes in common. In some embodiments, there are 10 different values in the color scheme corresponding to 10 different values of shared sequence reads. In some embodiments, there are 11 different values in the color scheme corresponding to 11 different values of shared sequence reads. In some embodiments, there are 12 different values in the color scheme corresponding to 12 different values of shared sequence reads. In some embodiments, there are 13 different values in the color scheme corresponding to 13 different values of shared sequence reads. In some embodiments, there are 14 different values in the color scheme corresponding to 14 different values of shared sequence reads. In some embodiments, there are 15 different values in the color scheme corresponding to 15 different values of shared sequence reads. In some embodiments, there are between five and one hundred different values in the color scheme corresponding to between five and one hundred different values of shared sequence reads.

Referring to FIG. 34, affordance 3308 can be used to pan (translational movement of) the view initially selected by search field 1250 so that different regions of the reference genome can be viewed. Referring to FIG. 34, affordance 3310 can be used to zoom the view initially selected by search field 1250 so that different amounts the reference genome can be viewed.

In some embodiments, the different views offered (e.g., haplotype/phase 152, structural variants 154, and reads 156) by the haplotype visualization tool 148 are all linked. For instance, a user may navigate from one view to another to see the same data using an alternate visualization without reentering information using affordances 1252, 1254, and 1256. For instance, the user may toggle between the matrix view of the structural variants module 154 and the haplotype view of the phase visualization module 152.

Figure 17:
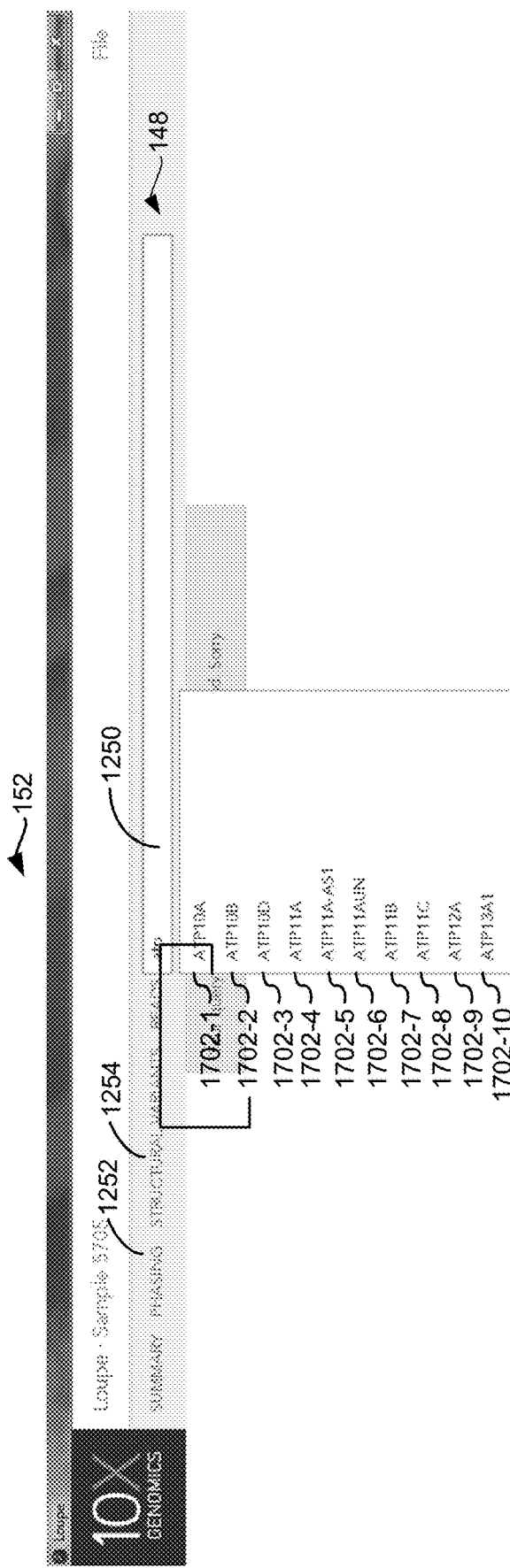
FIG. 17 illustrates search function features of a haplotype visualization tool in accordance with some embodiments.
Figure 18:
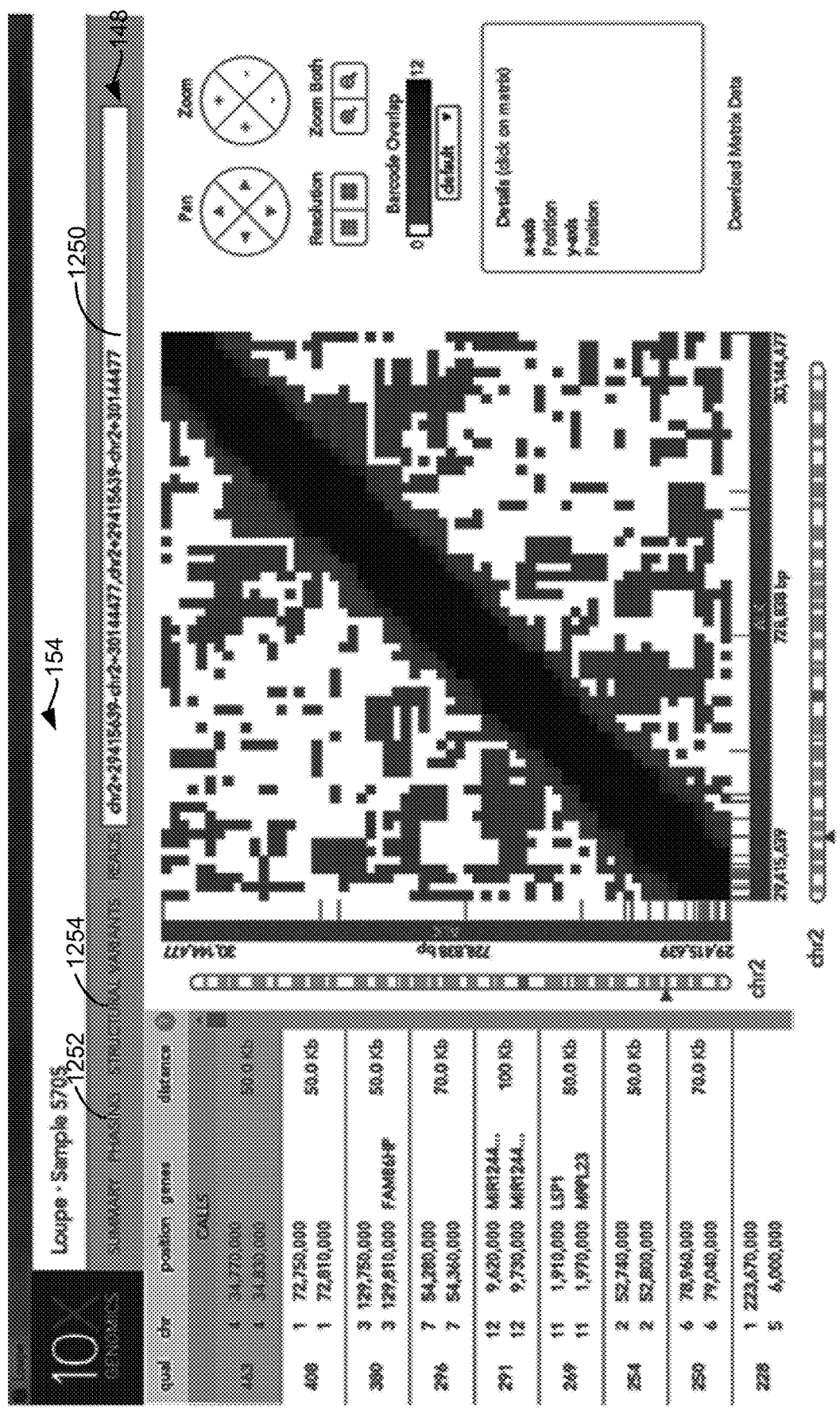
FIG. 18 illustrates a screen shot of a structural variants module in a haplotype visualization tool in accordance with some embodiments.
Figure 19:
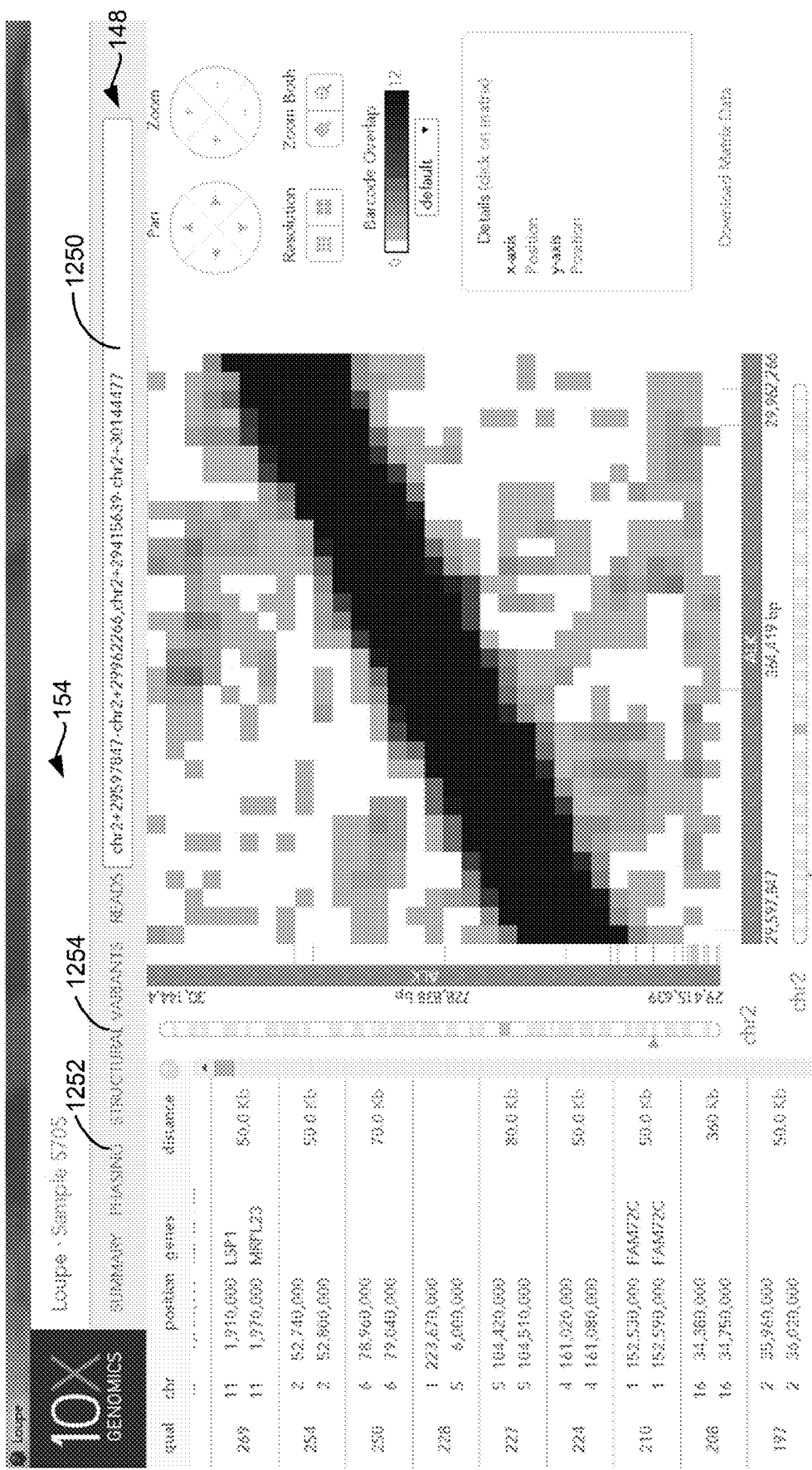
FIG. 19 illustrates another screen shot of a structural variants module in a haplotype visualization tool in accordance with some embodiments.
Figure 20:
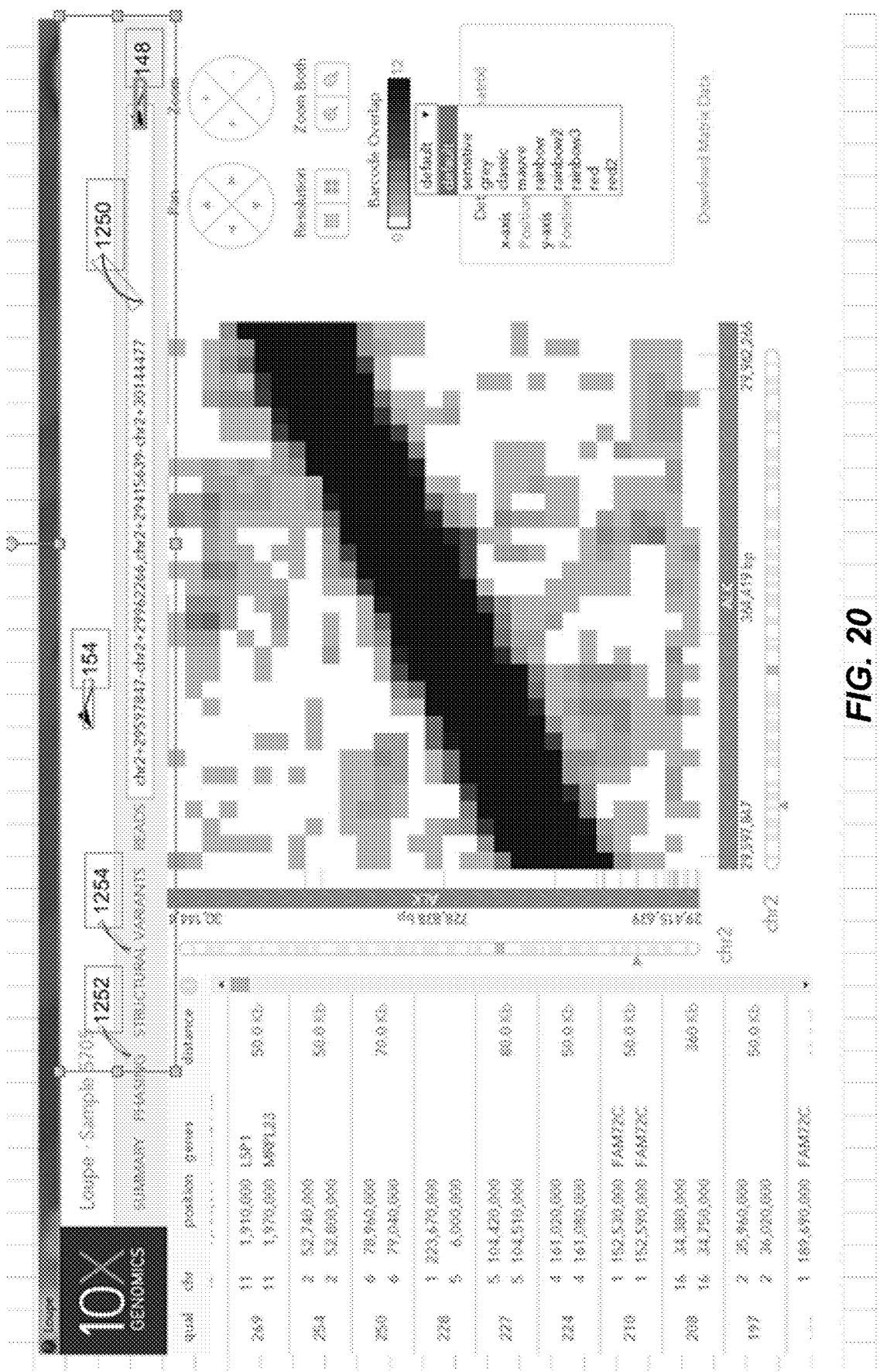
FIG. 20 illustrates still another screen shot of a structural variants module in a haplotype visualization tool in accordance with some embodiments.
Figure 21:
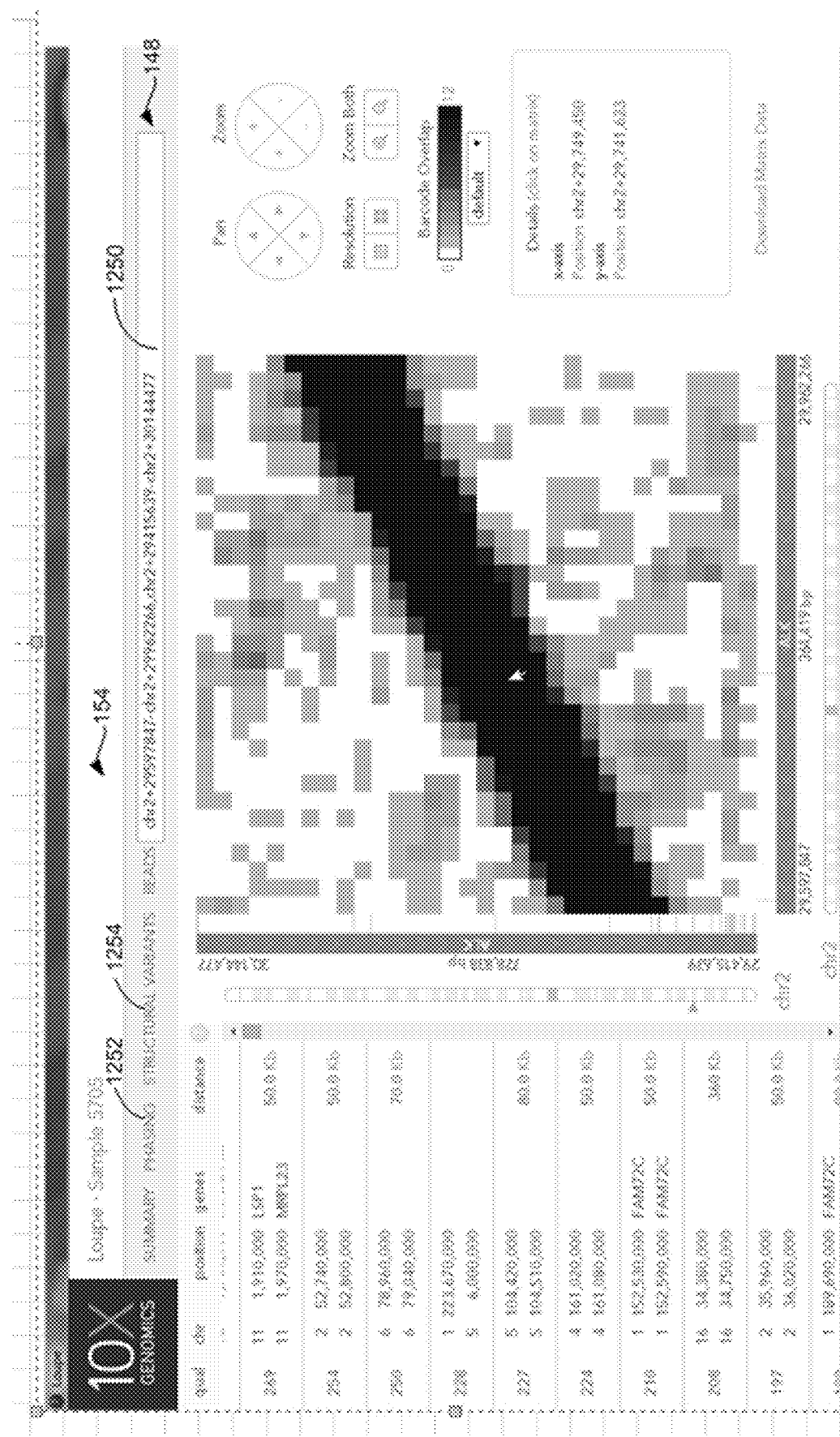
FIG. 21 illustrates still an additional screen shot of a structural variants module in a haplotype visualization tool in accordance with some embodiments.
Figure 22:
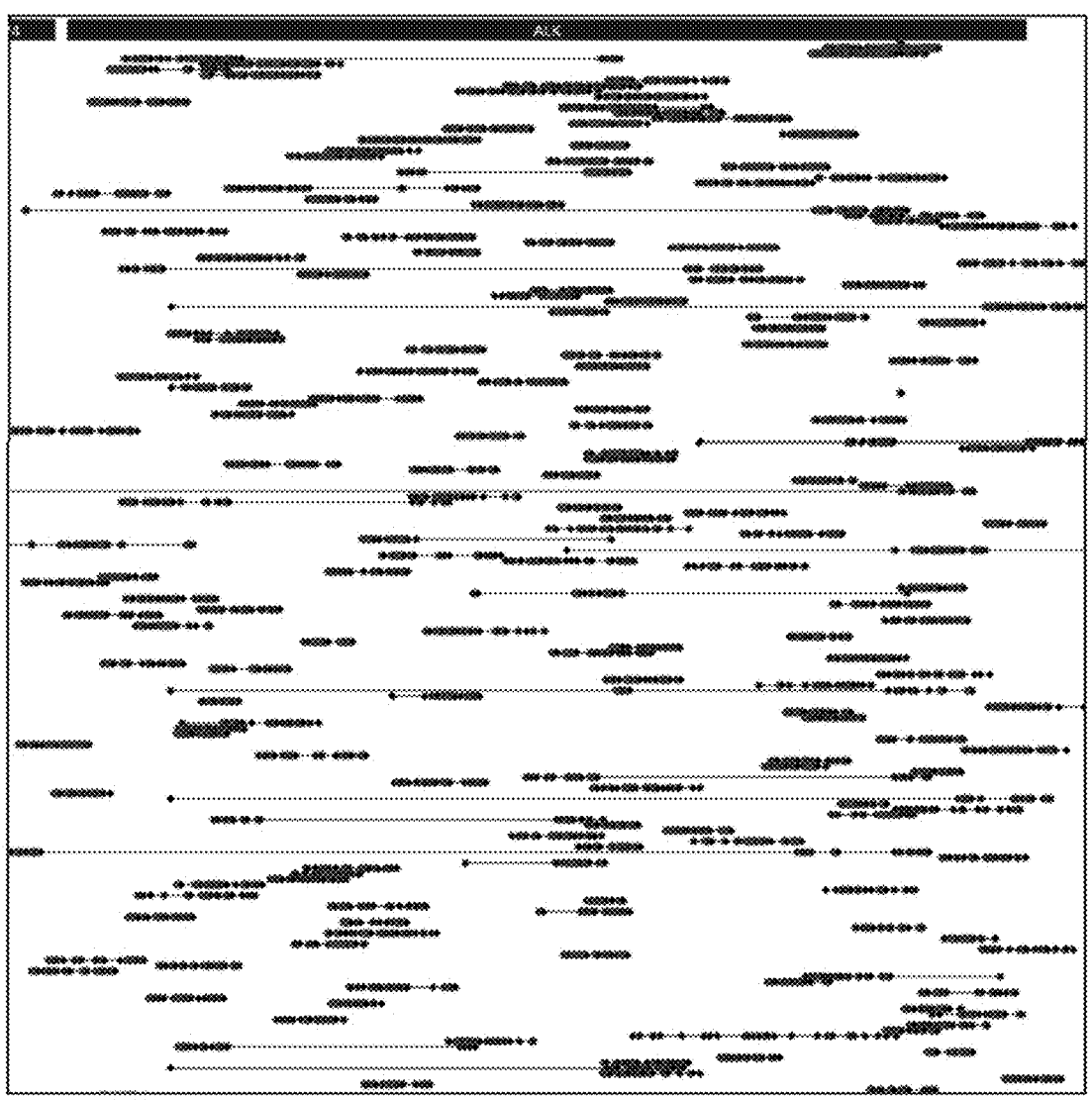
FIG. 22 illustrates a screen shot of a read visualization module in a haplotype visualization tool in accordance with some embodiments.
Figure 23:
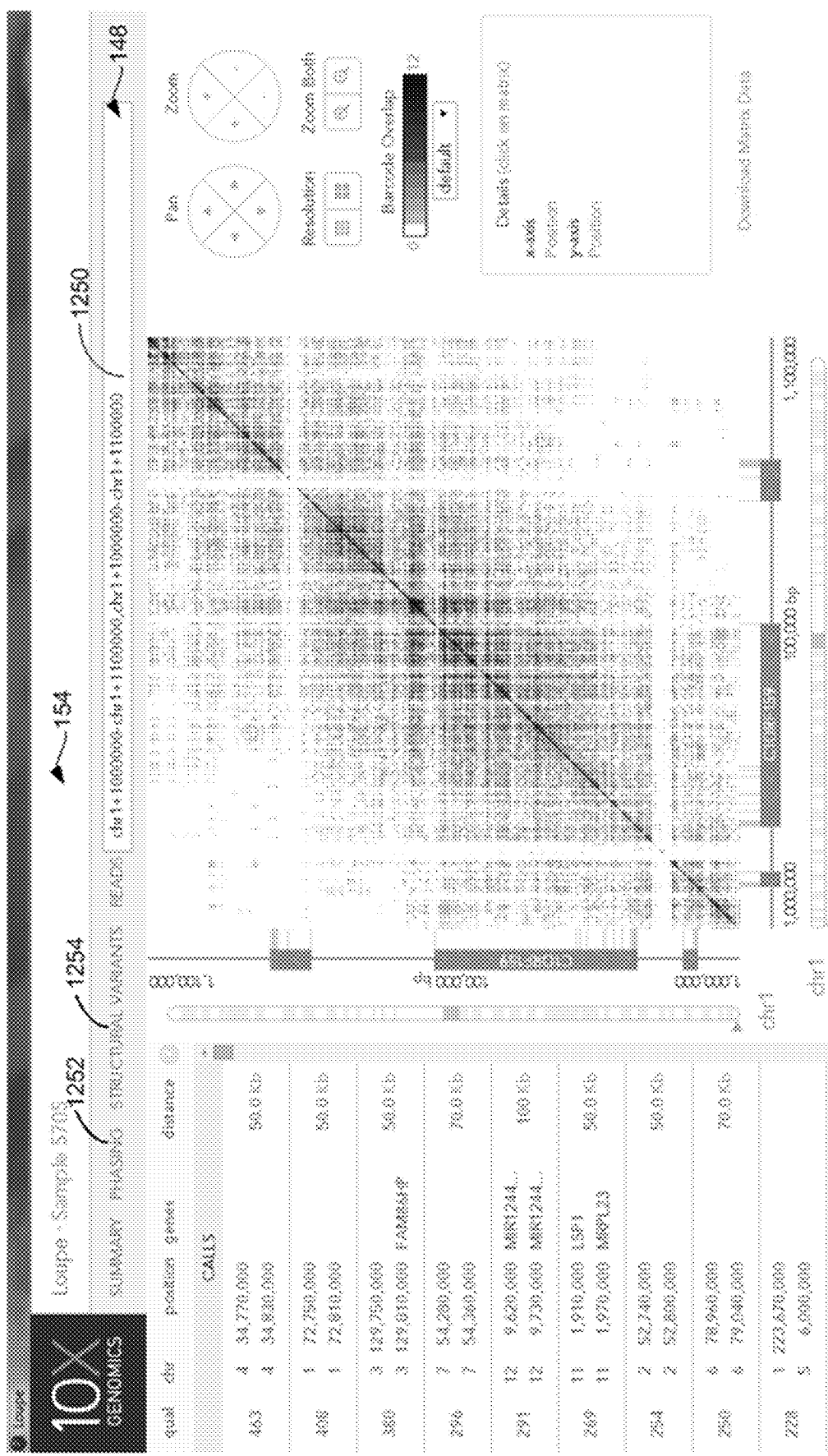
FIG. 23 illustrates another screen shot of a structural variants module in a haplotype visualization tool in accordance with some embodiments.
Figure 24:
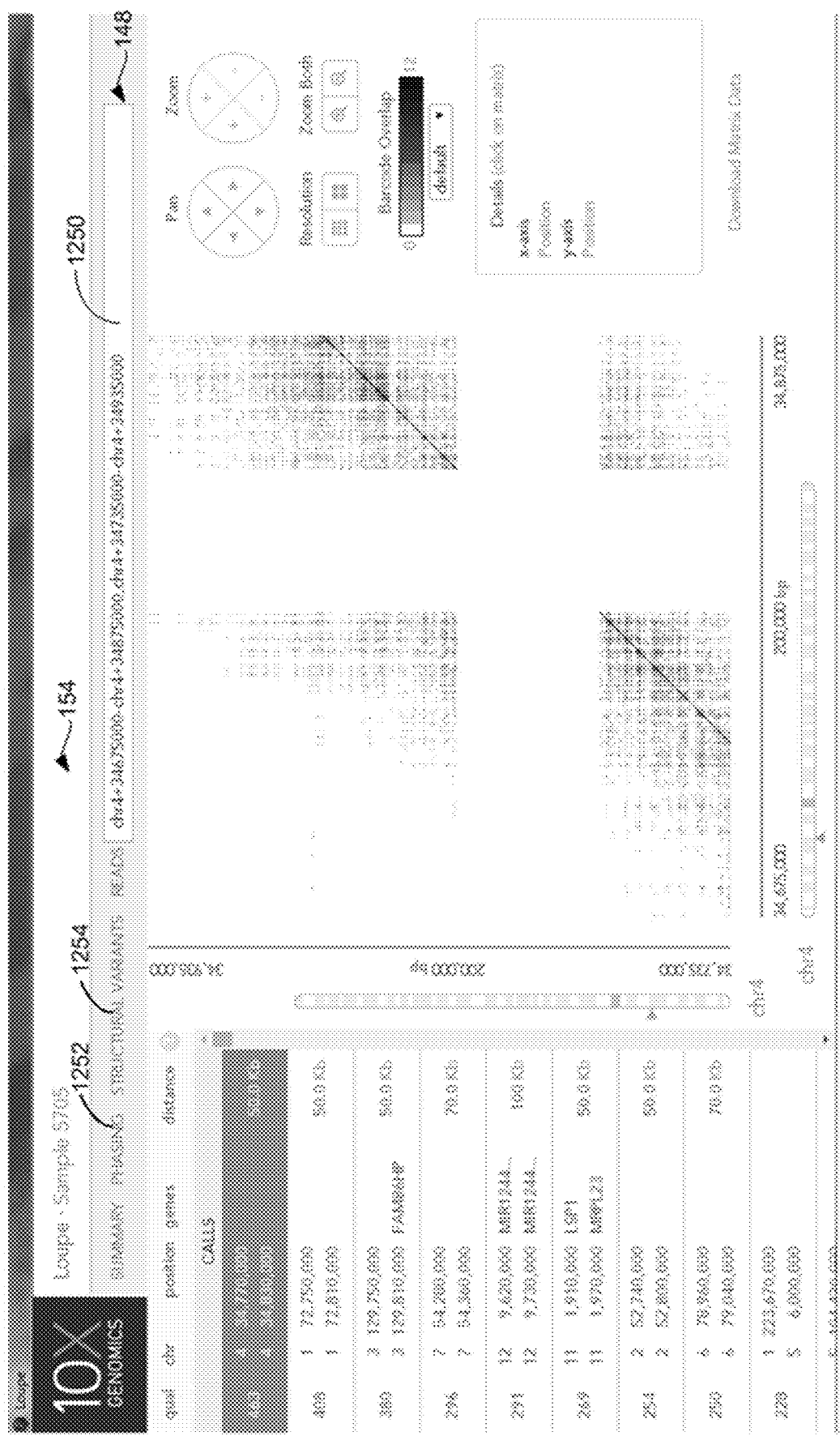
FIG. 24 illustrates another screen shot of a structural variants module in a haplotype visualization tool in accordance with some embodiments.
Figure 25:
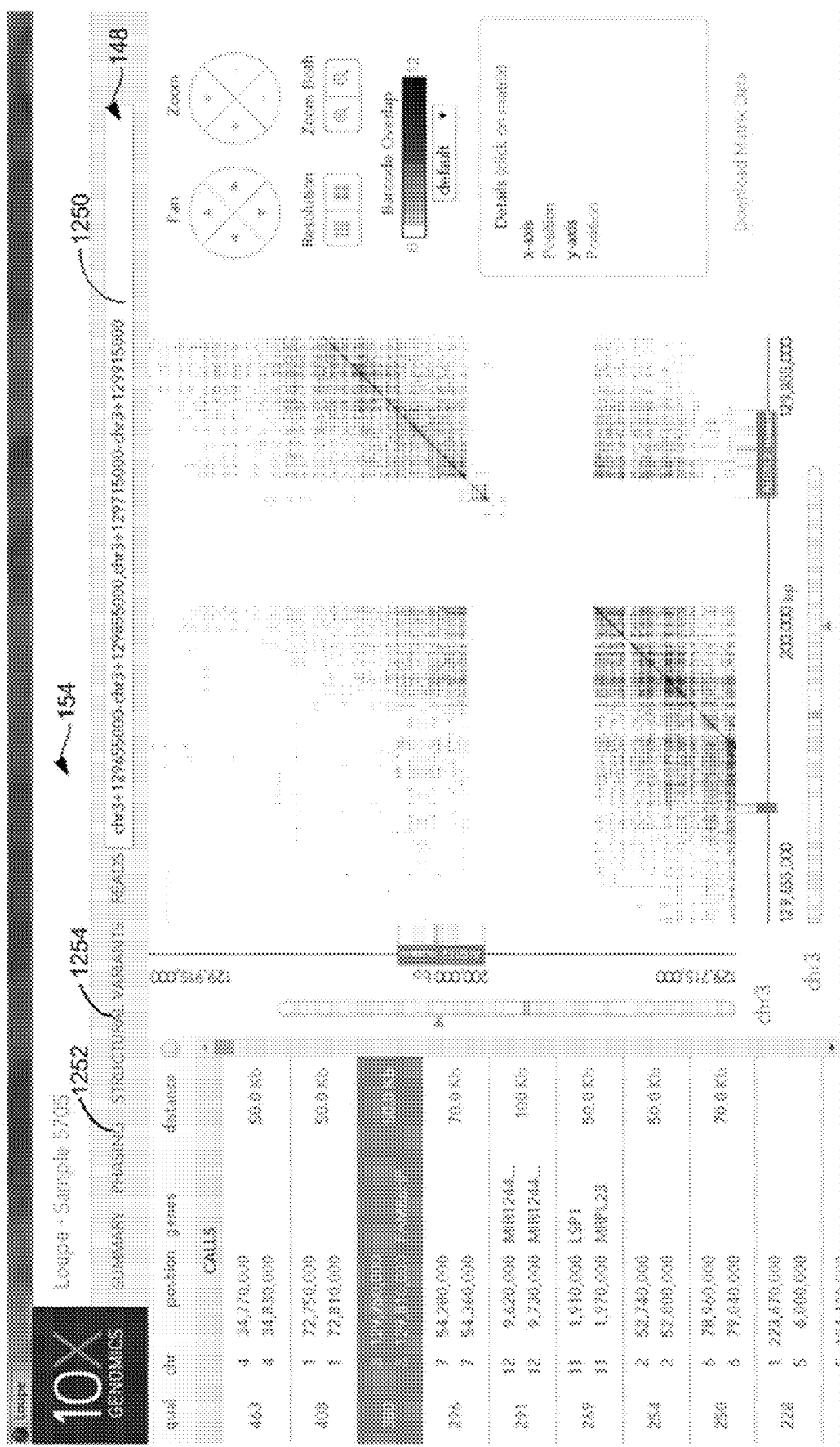
FIG. 25 illustrates another screen shot of a structural variants module in a haplotype visualization tool in accordance with some embodiments.

A "smart" search affordance 1250 is employed in the various views. Referring to FIG. 17, as a user types in the search affordance 1250, the program will attempt to auto-complete the partial query with real gene names or other forms of chromosomal locations in real time. In some embodiments, each time the user enters another character in the search affordance 1250, the partial query in the search affordance 1250 is queried against a lookup table in the subject nucleic acid sequencing dataset 126. In some embodiments, this lookup table is the gene track 320 and/or the exon track 322. Advantageously, in some embodiments, the haplotype visualization tool 148 maintains a history of past user queries. Thus, when a user starts to enter a new query, matches (or partial matches) against former queries are also displayed to the user for selection. This is particularly useful given the complex query syntax that is supported by the search bar 1250 in some embodiments. For example, as discussed above a user may query for multiple regions at once by separating queries with a variety of punctuators. A user may also enter a genomic coordinate directly in a number of formats.

In some embodiments, system 100 stores genomic data to be displayed in a custom file format (e.g., the format of nucleic acid sequencing dataset 126). The file is generated by a "preprocessor" which takes reference data, the VCF file, the BAM, file and the structural variant file as inputs and produces a single output nucleic acid sequencing dataset 126. The nucleic acid sequencing dataset 126 contains all of the information that is required to display a given dataset. The file is organized into several sections. A small synopsis section 308 that is roughly 25 MB and a much larger data section 340 (100 MB to 20 GB). These sections are further subdivided as described above. When the nucleic acid sequencing dataset 126 is loaded, it loads just the index section into memory. System 100 uses that data to find appropriate ranges of the data section to load into memory on-demand. Variant calls and read information is stored in the data section, the rest of the data loupe needs is small enough to store in the index section.

The data section is organized to chunks which are about ~250 KB in some embodiments. When system 100 requires information stored in the data section it consults the relevant index in the synopsis section (e.g., gene track, exon track, etc.) to find the chunk that should have the data and loads the entire chunk into memory. In some embodiments, the chunks for variant data are JSON-encoded structures containing the variant data as well as the supporting barcode information. In some embodiments, the chunks for read data have an array of small (8-byte) data structures in which each structure contains the position, length, and barcode of a single read. In some embodiments, both variant and read data is sorted by genomic position so that in general, system 100 will make only a small number of on-disk reads to acquire all of the data it needs to display a given subset of the data. In some embodiments, the rest of the data that system 100 needs for visualization (such as the location of genes, structural variant breakpoints, etc) is stored in the index (synopsis) section of the nucleic acid sequencing dataset 126 file as an "itree". An itree is an implementation of an interval tree. It is a reusable data structure (usually encoded in JSON) for annotating ranges of the genome. Thus exons, genes, phase blocks, and structural variant breakpoints are all encoded with the same mechanism even though they are displayed differently.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first object could be termed a second object, and, similarly, a second object could be termed a first object, without changing the meaning of the description, so long as all occurrences of the "first object" are renamed consistently and all occurrences of the "second object" are renamed consistently. The first object and the second object are both objects, but they are not the same object.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed:

1. A system for providing structural variation and phasing information over a network connection to a remote client computer, the system comprising one or more microprocessors, a persistent memory and a non-persistent memory, the persistent memory and the non-persistent memory collectively storing one or more nucleic acid sequencing datasets, wherein
   each respective nucleic acid sequencing dataset in the one or more nucleic acid sequencing datasets corresponds to at least one target nucleic acid in a respective sample in a plurality of samples, wherein
   the respective sample is associated with a genome of at least one species,
   the respective nucleic acid sequencing dataset comprises (i) a header, (ii) a synopsis, and (iii) a data section,
   the data section comprises a plurality of sequencing reads,
   each respective sequencing read in the plurality of sequencing reads comprises a nucleic acid sequence comprising a first portion that corresponds to a subset of at least one target nucleic acid in the respective sample and a second portion that encodes a respective identifier for the respective sequencing read in a plurality of identifiers,
   each respective identifier is independent of the sequence of the at least one target nucleic acid, and
   the plurality of sequencing reads collectively include the plurality of identifiers, and wherein
   the persistent memory and the non-persistent memory further collectively store one or more programs that use the one or more microprocessors to:
   provide a visualization tool for installation on the remote client computer;
   obtain a request, received from the remote client computer from a user, over a network connection, for structural variation and phasing information using a first dataset in the one or more datasets; and
   responsive to obtaining the request, automatically parse the request by:
   (i) loading the header and the synopsis of the first dataset into the non-persistent memory if not already loaded into the non-persistent memory while retaining the data section in persistent memory,
   (ii) comparing the request to the synopsis of the first dataset thereby identifying one or more portions of the data section of the first dataset,
   (iii) loading the one or more identified portions of the data section into non-persistent memory, wherein the loading loads less than the entirety of the data section,
   (iv) formatting structural variation and phasing information for display on the client computer using the first dataset, and
   (v) transmitting the formatted structural variation and phasing information over the network connection to the remote client computer for display on the remote client computer.

2. A system for providing structural variation and phasing information, the system comprising one or more microprocessors, a persistent memory and a non-persistent memory, the persistent memory and the non-persistent memory collectively storing one or more nucleic acid sequencing datasets, wherein
  each respective nucleic acid sequencing dataset in the one or more nucleic acid sequencing datasets corresponds to at least one target nucleic acid in a respective sample in a plurality of samples, wherein
    the respective sample is associated with a genome of at least one species,
    the respective nucleic acid sequencing dataset comprises (i) a header, (ii) a synopsis, and (iii) a data section,
    the data section comprises a plurality of sequencing reads,
    each respective sequencing read in the plurality of sequencing reads comprises a nucleic sequence comprising a first portion that corresponds to a subset of at least one target nucleic acid in the respective sample and a second portion that encodes a respective identifier for the respective sequencing read in a plurality of identifiers,
    each respective identifier is independent of the sequence of the at least one target nucleic acid, and
    the plurality of sequencing reads collectively include the plurality of identifiers, and wherein
  the persistent memory and the non-persistent memory further collectively store one or more programs that use the one or more microprocessors to:
  provide a visualization tool;
  obtain a request from a user, through the visualization tool, for structural variation and phasing information using a first dataset in the one or more datasets,
  responsive to obtaining the request, automatically parse the request by:
    (i) loading the header and the synopsis of the first dataset into the non-persistent memory if not already loaded into the non-persistent memory while retaining the data section in persistent memory,
    (ii) comparing the request for sequence information to the synopsis of the first dataset thereby identifying one or more portions of the data section of the first dataset,
    (iii) loading the one or more identified portions of the data section into non-persistent memory, wherein the loading loads less than the entirety of the data section,
    (iv) formatting structural variation and phasing information for display in the visualization tool using the first dataset, and
    (v) displaying the formatted structural variation and phasing information in the visualization tool.

3. A system for obtaining structural variation and phasing information over a network connection from a remote computer, wherein the system comprises one or more microprocessors, and a memory that stores one or more programs, wherein the one or more programs use the one or more microprocessors to execute a method comprising:
  (A) invoking a visualization tool;
  (B) obtaining, through the visualization tool from a user, a request for structural variation and phasing information in a first nucleic acid sequencing dataset from among one or more nucleic acid sequencing datasets stored on the remote computer, wherein each respective nucleic acid sequencing dataset in the one or more nucleic acid sequencing datasets corresponds to at least one target nucleic acid in a respective sample in a plurality of samples, wherein
    the respective sample is associated with a genome of at least one species,
    the respective nucleic acid sequencing dataset comprises (i) a header, (ii) a synopsis, and (iii) a data section,
    the data section comprises a plurality of sequencing reads,
    each respective sequencing read in the plurality of sequencing reads comprises a nucleic acid sequence comprising a first portion that corresponds to a subset of at least one target nucleic acid in the respective sample and a second portion that encodes a respective identifier for the respective sequencing read in a plurality of identifiers,
    each respective identifier is independent of the sequence of the at least one target nucleic acid, and
    the plurality of sequencing reads collectively include the plurality of identifiers;
  (C) sending the request to the remote computer over the network connection, wherein the remote computer has persistent memory and non-persistent memory, thereby causing the remote computer to execute a method comprising:
    (i) loading the header and the synopsis of the first dataset into the non-persistent memory if not already loaded into the non-persistent memory of the remote computer while retaining the data section in persistent memory,
    (ii) comparing the request for sequence information to the synopsis of the first dataset thereby identifying one or more portions of the data section of the first dataset,
    (iii) loading the one or more identified portions of the data section into non-persistent memory, wherein the loading loads less than the entirety of the data section, and
    (iv) formatting structural variation and phasing information; and
  (D) receiving the formatted structural variation and phasing information over the network connection from the remote computer for display in the visualization tool.

4. The system of claim 1, wherein the header delineates a plurality of components in the respective nucleic acid sequencing dataset.

5. The system of claim 4, wherein the plurality of components comprises two or more components selected from the group consisting of a summary, an index to variant call data, a phase block track, a refseq index track, a gene track, an exon track, an index to read data, a structural variant dataset track, an index to a target dataset, and an index to a fragment dataset.

6. The system of claim 5, wherein the plurality of components comprises the summary and wherein the summary comprises two or more items in the group consisting of:
  a percentage of known SNPs phased in the respective nucleic acid sequencing dataset,
  a longest phase block in the respective nucleic acid sequencing dataset,
  a number of unique barcodes used in the respective nucleic acid sequencing dataset,
  an average fragment length in the respective nucleic acid sequencing dataset,
  a mean of the average fragment length in the respective nucleic acid sequencing dataset, a percentage of fragments greater than a lower threshold in the respective nucleic acid sequencing dataset, a fragment length histogram in the respective nucleic acid sequencing dataset, an N50 phase block size in the respective nucleic acid sequencing dataset, a phase block histogram in the respective nucleic acid sequencing dataset, a number of sequence reads represented by respective the nucleic acid sequencing dataset, a median insert size in the respective nucleic acid sequencing dataset, a median depth in the respective nucleic acid sequencing dataset, a percent of the target genome with zero coverage in the respective nucleic acid sequencing dataset, a mapped reads percentage for the respective nucleic acid sequencing dataset, a PCR duplication percentage for the respective nucleic acid sequencing dataset, a coverage histogram for the in the respective nucleic acid sequencing dataset, an identity of a test nucleic acid that forms the basis for the respective nucleic acid sequencing dataset, a genome source for the respective nucleic acid sequencing dataset, a sex of an organism that originated the at least one test nucleic acid of the respective nucleic acid sequencing dataset, a sex of the organism that originate the respective sample of the in the respective nucleic acid sequencing dataset, a dataset file format version of the in the respective nucleic acid sequencing dataset, and a pointer to a plurality of structural variant calls made for the respective nucleic acid sequencing dataset.

7. The system of claim 5, wherein the plurality of components comprises the index to variant call data that provides a correspondence between respective ranges of the genome of the species to offsets in the data section where variant call data for the respective ranges is found.

8. The system of claim 5, wherein the plurality of components comprises the phase block track and wherein the phase block track comprises (i) a dictionary and (ii) a track data section comprising phase information for one or more chromosomes in the genome of the at least one species.

9. The system of claim 5, wherein the plurality of components comprises the refseq index, wherein the refseq index comprises an index of a plurality of molecular variation identifiers that are called in the sample.

10. The system of claim 5, wherein the plurality of components comprises the gene track and wherein the gene track comprises (i) a gene track dictionary and (ii) a gene track data section.

11. The system of claim 5, wherein the plurality of components comprises the index to read data wherein the index to read data comprises a lookup table between a respective identifier in the plurality of identifiers and a shortened version of the respective identifier.

12. The system of claim 5, wherein the plurality of components comprises the structural variant dataset track, and the structural variant dataset track comprises (i) a dictionary and (ii) a track data section comprising structural variant call information identified in the plurality of sequencing reads.

13. The system of claim 12, wherein the dictionary comprises a plurality of names, and for each respective name in the plurality of names, an offset into the track data where records for the corresponding name are found.

14. The system of claim 13, wherein the track data section comprises a plurality of structural variant records, and each structural variant record in the plurality of structural variant records represents a structural variant call made in the at least one target nucleic acid in the sample.

15. The system of claim 14, wherein each respective structural variant record in the plurality of structural variant records is represented by a node in a plurality of nodes in a respective interval tree in a plurality of interval trees, and each interval tree in the plurality of interval trees represents a chromosome in a plurality of chromosomes for the species.

16. The system of claim 5, wherein the plurality of components comprises the index to the target dataset, the target dataset comprises the regions of the at least one target nucleic acid in the sample that were selected for sequencing in the respective nucleic acid sequencing dataset, the target dataset is indexed by a target dataset index stored in the synopsis, and the target dataset is stored in the data section.

17. The system of claim 5, wherein the plurality of components comprises the index to the fragment dataset, the fragment dataset comprises a length, chromosomal position, identifier, and phase of each fragment of the at least one target nucleic acid in the sample, the fragment dataset is indexed by a fragment dataset index stored in the synopsis, and the fragment dataset is stored in the data section.

18. The system of claim 1, wherein the request is for phasing information in a region of the genome and the formatted phasing information includes a graphic representation comprising:

a first haplotype track corresponding to a first parental haplotype of a first species in the at least one species in the region of the genome for the first dataset, a second haplotype track, corresponding to a second parental haplotype of the first species in the region of the genome for the first dataset, an indeterminate track corresponding to regions of the at least one nucleic acid sample that have not been assigned a parental haplotype in the region of the genome for the first dataset.

19. The system of claim 18, wherein the graphic representation further comprises a graphic representation of each gene that is in the region of the genome.

20. The system of claim 18, wherein the graphic representation further comprises a coverage track for the region of the genome, wherein the coverage track comprises a plurality of vertical bars, and wherein each respective vertical bar in the plurality of vertical bars indicates an average coverage-per-base in the first dataset for a corresponding portion of the genome under the bar.

21. The system of claim 1, wherein the request is converted, without human intervention, to genomic coordinates by comparison of the request against one or more lookup tables that match alphanumeric entries of genes to genomic coordinates.

22. The system of claim 1, wherein the respective sample is associated with a genome of a plurality of species and includes at least a portion of the genome of a first species and a portion of the genome of the second species.

* * * * *